US010000511B2

(12) United States Patent
Walensky et al.

(10) Patent No.: US 10,000,511 B2
(45) Date of Patent: Jun. 19, 2018

(54) SMALL MOLECULES FOR THE MODULATION OF MCL-1 AND METHODS OF MODULATING CELL DEATH, CELL DIVISION, CELL DIFFERENTIATION AND METHODS OF TREATING DISORDERS

(71) Applicant: Dana-Farber Cancer Institute, Inc., Boston, MA (US)

(72) Inventors: Loren D. Walensky, Newton Centre, MA (US); Michelle L. Stewart, Brookline, MA (US); Nicole Cohen, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days. days.

(21) Appl. No.: 14/705,764

(22) Filed: May 6, 2015

(65) Prior Publication Data

US 2015/0315211 A1 Nov. 5, 2015

Related U.S. Application Data

(62) Division of application No. 13/576,116, filed as application No. PCT/US2011/023220 on Jan. 31, 2011, now abandoned.

(60) Provisional application No. 61/299,803, filed on Jan. 29, 2010.

(51) Int. Cl.
| | |
|---|---|
| C07D 513/04 | (2006.01) |
| C07D 249/12 | (2006.01) |
| C07D 401/12 | (2006.01) |
| C07D 413/14 | (2006.01) |
| C07D 409/12 | (2006.01) |
| C07C 311/20 | (2006.01) |
| C07D 409/14 | (2006.01) |
| C07D 405/14 | (2006.01) |
| C07D 417/14 | (2006.01) |
| C07D 307/54 | (2006.01) |
| C07D 405/12 | (2006.01) |
| C07D 409/06 | (2006.01) |
| C07D 413/06 | (2006.01) |
| C07D 279/06 | (2006.01) |
| C07D 327/04 | (2006.01) |
| C07D 239/60 | (2006.01) |
| C07D 403/06 | (2006.01) |
| C07D 277/34 | (2006.01) |
| C07D 417/04 | (2006.01) |
| C07C 337/08 | (2006.01) |
| C07C 251/20 | (2006.01) |
| C07C 251/84 | (2006.01) |
| C07C 335/16 | (2006.01) |
| C07D 403/04 | (2006.01) |
| C07D 403/08 | (2006.01) |

(52) U.S. Cl.
CPC .......... *C07D 513/04* (2013.01); *C07C 251/20* (2013.01); *C07C 251/84* (2013.01); *C07C 311/20* (2013.01); *C07C 335/16* (2013.01); *C07C 337/08* (2013.01); *C07D 239/60* (2013.01); *C07D 249/12* (2013.01); *C07D 277/34* (2013.01); *C07D 279/06* (2013.01); *C07D 307/54* (2013.01); *C07D 327/04* (2013.01); *C07D 401/12* (2013.01); *C07D 403/04* (2013.01); *C07D 403/06* (2013.01); *C07D 403/08* (2013.01); *C07D 405/12* (2013.01); *C07D 405/14* (2013.01); *C07D 409/06* (2013.01); *C07D 409/12* (2013.01); *C07D 409/14* (2013.01); *C07D 413/06* (2013.01); *C07D 413/14* (2013.01); *C07D 417/04* (2013.01); *C07D 417/14* (2013.01); *C07C 2602/10* (2017.05)

(58) Field of Classification Search
CPC .. C07D 513/04; C07D 249/12; C07D 401/12; C07D 413/14
USPC ............................................. 514/370; 544/54
See application file for complete search history.

(56) References Cited

U.S. PATENT DOCUMENTS

| | | | |
|---|---|---|---|
| 2004/0002117 | A1 | 1/2004 | Hogan et al. |
| 2004/0157883 | A1 | 8/2004 | Chen et al. |
| 2004/0191328 | A1 | 9/2004 | Warrell, Jr. et al. |
| 2007/0203236 | A1 | 8/2007 | Smith et al. |
| 2009/0054402 | A1 | 2/2009 | Wang et al. |
| 2009/0069324 | A1 | 3/2009 | Reed et al. |
| 2009/0124616 | A1 | 5/2009 | Song et al. |
| 2009/0163545 | A1 | 6/2009 | Goldfarb |
| 2010/0004324 | A1 | 1/2010 | Skaar et al. |
| 2010/0234456 | A1 | 9/2010 | Wendt et al. |
| 2011/0077250 | A1* | 3/2011 | Ryder .................... A61K 31/70 514/236.8 |
| 2012/0142917 | A1 | 6/2012 | Lawrence et al. |

FOREIGN PATENT DOCUMENTS

| | | |
|---|---|---|
| EP | 1475372 | 11/2004 |
| JP | 2004/099518 A | 4/2004 |
| JP | 2006516383 | 7/2006 |
| JP | 2007084494 | 4/2007 |
| WO | WO 2004/069200 A2 | 8/2004 |

(Continued)

OTHER PUBLICATIONS

ZINC15913384, PubChem SID 59797118, PubChem CID: 6848561 (509102-00-5), Available Date: May 28, 2009. http://pubchem.ncbi.nlm.nih.gov/substance/59797118/version/1.*

(Continued)

*Primary Examiner* — Yih-Horng Shiao
(74) *Attorney, Agent, or Firm* — Fish & Richardson P.C.

(57) ABSTRACT

This invention relates to compounds which selectively bind to the survival protein MCL-1 with high affinity and selectivity, pharmaceutical compositions containing such compounds and the use of those compounds or compositions for modulating MCL-1 activity and for treating hyperproliferative disorders, angiogenesis disorders, cell cycle regulation disorders, autophagy regulation disorders, inflammatory disorders, and/or infectious disorders and/or for enhancing cellular engraftment and/or wound repair, as a sole agent or in combination with other active ingredients.

17 Claims, 19 Drawing Sheets

(56) References Cited

FOREIGN PATENT DOCUMENTS

| WO | WO 2008/131000 | 10/2008 |
|---|---|---|
| WO | WO 2008/156676 | 12/2008 |
| WO | WO 2009/023773 | 2/2009 |
| WO | WO 2010/005534 A2 | 1/2010 |
| WO | WO 2010/102286 | 9/2010 |
| WO | WO 2010/151799 A2 | 12/2010 |
| WO | WO 2011-094708 A2 | 8/2011 |

OTHER PUBLICATIONS

STN CAPLUS 2010:1626364/AN WO 2010151799/US 20110077250, Priority date: US 2009-61220988 filed on Jun. 26, 2009.*
MLS000774515, National Center for Biotechnology Information. PubChem Compound Database; CID=5894545, https://pubchem.ncbi.nlm.nih.gov/compound/5894545 (accessed Oct. 21, 2016).*
509102-00-5, National Center for Biotechnology Information. PubChem Compound Database; CID=6848561, https://pubchem.ncbi.nlm.nih.gov/compound/6848561 (accessed Oct. 21, 2016).*
Barret et al., "Preparation of Quinone-Imide Ketals From Amides with Hyper valent Organo-Iodine Compounds", Tetrahedron Letts., 32(19):2133-2134 (1991).
Bukhtoyarova et al., "Synthesis and Spectral Properties of N-Aryl-5-hydroxy-1,4-naphthoquinone 4-Imines", Russian J. Organ. Chem., 39(9):1309-1315 (2003).
Bukhtoyarova et al., "Dependence of Carbon Chemical Shifts in the $^{13}$C NMR Spectra of 5-Hydroxy-1,4-naphthoquinon-4-imines on Position of Tautomeric Equilibrium", Russian J. Organic Chem., 38(6):851-854 (2002).
Ektova et al., "Synthesis and Isomerization of N, N'-Diaryl-2,2'-BI(1,4-Naphtho-Quinone) 4,4'-Diimmes", J. Organ. Chem. of the USSR, 22:748-752 (1986).
Granero et al., "Synthesis of New Isoxazolylnaphthoquinones as Potential Trypanocidal and Antibacterial Agents", J. Chem. Research (S), 2:110-111 (1999).
Johnson et al., "Synthesis and Antibacterial Activity of 1-(Arylamino)-1H-pyrroles and 4-(1H-Pyrrol-1-ylimino)-2,5-cyclohexadienes", J. Med. Chem., 24(11):1314-1319 (Nov. 1981).
Khalil et al., "Synthesis and study of some new 1,3-isoindoledione derivatives as potential antibacterial agents", European J. Med. Chem., 45(4):1552-1559 (2010).
Kung et al., "Photegenerated N-Methyl-N-1-naphthylnitrenium Ion: Laser Flash Photolysis, Trapping Rates, and Product Study"., J. Org. Chem., 70:3127-3132 (2005).
Myung et al., "2D-QSAR and HQSAR of the Inhibition of Calcineurin-NFAT Signaling by Blocking Protein-Protein Interaction with N-(4-oxo-1(4H)-naphthalenylidenebenzenesulfonamide Analogues", Arch Pharm Res, 30(8):976-983 (2007).
Reed et al., "Identification and Characterization of the First Small Molecule Inhibitor of MDMX", J. Biol. Chem., 285(14):10786-10796 (Apr. 2010).
Richter et al., "The Lead Tetraacetate Oxidation of 1- and 2-Benzenesulfonamido- and Benzamido-naphthalenes", J. Organic Chemistry, 27(11):4066-4068 (1962).
Sicardi et al., "Mutagenic activity of isoxazolylnaphthoquinoneimines assayed by micronucleus bone marrow test", Mutation Res., 343:61-66 (1995).
Sperandeo et al., "Synthesis, antiprotozoal and cytotoxic activities of new N-(3,4-dimethyl-5-isoxazolyl)-1,2-naphthoquinone-4-amino derivatives"., IL FARMACO., 59:431-435 (2004).
Wosikowski et al., "Identification of Epidermal Growth Factor Receptor and c-erbB2 Pathway Inhibitors by Correlation With Gene Expression Patterns", J. Natl. Cancer Inst., 89(20):1505-1515 (Jan. 1997).
Pubchem database and ChemCats database search results accompanying EP Office Action dated Sep. 30, 2014.
Database PubChem Compound [Online], NCBI; May 30, 2009, Database accession No. CID 42371696.
Database PubChem Compound [Online], NCBI; May 30, 2009, Database accession No. CID 42504827.
Registry (STN) [online], Dec. 8, 2004, [searching date Oct. 27, 2014], CAS registration No. 794552-61-7.
Registry (STN) [online], Dec. 8, 2004, [searching date Oct. 27, 2014], CAS registration No. 794552-60-6.
Registry (STN) [online], Jan. 22, 2001, [searching date Oct. 27, 2014], CAS registration No. 315698-78-3.
Office Action issued in EP Patent Application No. 11737834.9-1462, dated Sep. 30, 2014.
Office Action issued in JP Patent Application No. 2012-551374, dated Nov. 11, 2014.
European Search Report for Application No. EP 11737834.9-1452 / 2528893, dated Jun. 25, 2013.
Armstrong, S. A., et al., Inhibition of FLT3 in MLL. Validation of a therapeutic target identified by gene expression based classification, Cancer Cell 3(2):173-183 (2003).
Bakhshi, A., et al., Cloning the chromosomal breakpoint oft(14;18) human lymphomas: clustering around JH on chromosome 14 and near a transcriptional unit on 18, Cell 41(3):899-906 (1985).
Bird, G. H., et al., Chapter 22 Synthesis and Biophysical Characterization of Stabilized alpha-Helices ofBCL-2 Domains, Methods Enzymol 446:369-386 (2008).
Boisvert-Adamo, K., et al., Mcl-1 is required for melanoma cell resistance to anoikis, Mol Cancer Res 7(4):549-556 (2009).
Chen, et al., Differential targeting of prosurvival Bcl-2 proteins by their BH3-only ligands allows complementary apoptotic function, Mol Cell, 17(3):393-403 (2005).
Cleary, and Sklar, Nucleotide sequence of a t(14;18) chromosomal breakpoint in follicular lymphoma and demonstration of a breakpoint-cluster region near a transcriptionally active locus on chromosome 18, Proc Natl Acad Sci USA 82(21):7439-7443 (1985).
Danial, N. N., et al., Dual role of proapoptotic BAD in insulin secretion and beta cell survival, Nat Med 14(2):144-153 (2008).
Deng, J., et al., BH3 profiling identifies three distinct classes of apoptotic blocks to predict response to ABT-737 and conventional chemotherapeutic agents, Cancer Cell 12(2):171-185 (2007).
Derenne, S., et al., Antisense strategy shows that Mcl-1 rather than Bcl-2 or Bc1-$x_L$ is an essential survival protein of human myeloma cells, Blood 100(1):194-199 (2002).
Ding, Q., et al., Myeloid Cell Leukemia-lInversely Correlates with Glycogen Synthase Kinase-3 {beta} Activity and Associates with Poor Prognosis in Human Breast Cancer, Cancer Res 67(10):4564-4571 (2007).
Ficarro SB, et al., Improved electrospray ionization efficiency compensates for diminished chromatographic resolution and enables proteomics analysis of tyrosine signaling in embryonic stem cells, Anal Chem. 81(9):3440-7 (2009).
Gavatbiotis, E., et al., BAX activation is initiated at a novel interaction site, Nature 455(7216):1076-1081 (2008).
Kitada, S., et al., Discovery, characterization, and structure-activity relationships studies of proapoptotic polyphenols targeting B-cell lymphocyte/leukemia-2 proteins, J Med Chem 46(20):4259-4264 (2003).
Kline, M. P., et al., ABT-737, an inhibitor of Bcl-2 family proteins, is a potent inducer of apoptosis in multiple myeloma cells, Leukemia 21(7):1549-1560 (2007).
Konopleva, M., et al., Mechanisms of apoptosis sensitivity and resistance to the BH3 mimetic ABT-737 in acute myeloid leukemia, Cancer Cell 10(5), 375-388 (2006).
Lin, X., et al., 'Seed' analysis of off-target siRNAs reveals an essential role of Mcl-1 in resistance to the small-molecule Bcl-2/Bcl-$X_L$ inhibitor ABT-737, Oncogene 26(27):3972-3979 (2007).
MacVicar, G. R., et al., An open-label, multicenter, phase I/II study of AT-101 in combination with docetaxel (D) and prednisone (P) in men with hormone refractory prostate cancer (HRPC), J Clin Oncol 26:16043 (Abstract) (2008).
Muchmore, et al., X-ray and NMR structure of human Bcl-xL, an inhibitor of programmed cell death, Nature, 381(6580):335-341 (1996).
Nguyen, M., et al., Small molecule obatoclax (GX15-070) antagonizes MCL-1 and overcomes MCL-1-mediated resistance to apoptosis, Proc Natl Acad Sci USA 104(49):19512-19517 (2007).

(56) References Cited

OTHER PUBLICATIONS

Oltersdorf, T., et al., *An inhibitor of Bcl-2 family proteins induces regression of solid tumours*, Nature 435(7042):677-681 (2005).
Pitter, K., et al., *Chapter 23 Dissection of the 32. BCL-2 Family Signaling Network with Stabilized alpha-Helices of BCL-2 Domains Methods*, Enzymol 446:387-408 (2008).
Sattler, et al., *Structure of Bcl-xL-Bak peptide complex: recognition between regulators of apoptosis*, Science, 275(5302):983-986 (1997).
Schafineister, C., et al., *An all-hydrocarbon cross-linking system for enhancing the helicity and metabolic stability of peptides*, J Am Chem Soc 122:5891-5892 (2000).
Shuker, S. B., et al., *Discovering high-affinity ligands for proteins: SAR by NMR*, Science 274(5292):1531-1534 (1996).
Taniai, M., et al., *Mcl-1 mediates tumor necrosis factor-related apoptosis-inducing ligand resistance in human cholangiocarcinoma cells*, Cancer Res 64(10):3517-3524 (2004).
Tse, C., et al., *ABT-263: a potent and orally bioavailable Bcl-2 family inhibitor*, Cancer Res 68(9):3421-3428 (2008).
Tsujimoto, et al., *The t(14;18) chromosome translocations involved in B-cell neoplasms result from mistakes in VDJ joining*, Science 229(4720):1390-1393 (1985).
van Delft, M. F., et al., *The BH3 mimetic ABT-737 targets selective Bcl-2 proteins and efficiently induces apoptosis via Bak/Bax if Mcl-1 is neutralized*, Cancer Cell 10(5), 389-399 (2006).
Walensky, L. D., *BCL-2 in the crosshairs: tipping the balance of life and death*, Cell Death Differ 13(8):1339-1350 (2006).
Walensky, L. D., et al., *A stapled BID BH3 helix directly binds and activates BAX*, Mol Cell 24(2):199-210 (2006).
Walensky, L. D., et al., *Activation of apoptosis in vivo by a hydrocarbon-stapled BH3 helix*, Science 305(5689):1466-1470 (2004).
Wang, G., et al., *Structure based design of potent small-molecule inhibitors of anti-apoptotic Bcl-2 proteins*, J Med Chem 49(21): 6139-6142 (2006).
Zhai, et al., *Differential regulation of Bax and Bak by anti-apoptotic Bcl-2 family proteins Bcl-B and Mcl-1*, J Biol Chem, 283(15): 9580-958 (2008).
Zhang, B., et al., *Myeloid cell factor-1 is a critical survival factor for multiple myeloma*, Blood 99(6):1885-1893 (2002).
Aiello et al., *Vascular Endothelial Growth Factor in Ocular Fluid of Patients With Diabetic Retinopathy and Other Retinal Disorders*, New Engl. J. Med., 331(22):1480- (1994).
Berge, et al., *Pharmaceutical Salts*, J. Pharm. Sci., 66(1):1-19 (1977).
Lopez et al., *Transdifferentiated Retinal Pigment Epithelial Cells Are Immunoreactive for Vascular Endothelial Growth Factor in Surgically Excised Age-Related Macular Degeneration Related Choroidal Neovascular Membranes*, Invest. Opththalmol Vis. Sci., 37(5):855-868 (1996).
Pe'er et al., *Hypoxia Induced Expression of Vascular Endothelial Growth Factgor by Retinal Cells is a Common Factor in Neovascularizing Ocular Diseases*, Laboratory Investigation, 72(6):638-645 (1995).
EPO Examination Report for EP App. No. 11737834.9, dated Aug. 26, 2016 (4 pages).
Jensen et al., (2010) *Anodic Oxidation and Organocatalysis: Direct Regio- and Stereoselective Access to meta-Substituted Anilines by alpha-Arylation of Aldehydes*, Angew. Chem. Int. Ed. 49:129-133.
CID 3318217, AC1MOCNT, PubChem Compound Summary, NIH, U.S. Natl Library of Medicine, National Center for Biotechnology Information, Aug. 11, 2016, (11 pages).
CID 5433262, STK215536, NIH, PubChem Compound Summary, U.S. Natl Library of Medicine, National Center for Biotechnology Information, Aug. 11, 2016, (14 pages).
CID 22525618, NIH, PubChem Compound Summary, U.S. Natl Library of Medicine, National Center for Biotechnology Information, Aug. 11, 2016, (11 pages).
CID 7728365, GNF-Pf-1078, PubChem Compound Summary, NIH, U.S. Natl Library of Medicine, National Center for Biotechnology Information, Aug. 11, 2016, (14 pages).
CID 2235899, ZINC02883560, PubChem Compound Summary, NIH, U.S. Natl Library of Medicine, National Center for Biotechnology Information, Aug. 11, 2016, (11 pages).
CID 24319562, STK981930, PubChem Compound Summary, NIH, U.S. Natl Library of Medicine, National Center for Biotechnology Information, Aug. 11, 2016, (11 pages).
CID 9611934, F0808-0868, PubChem Compound Summary, NIH, U.S. Natl Library of Medicine, National Center for Biotechnology Information, Aug. 11, 2016, (11 pages).
CID 9568012, ST50774387, PubChem Compound Summary, NIH, U.S. Natl Library of Medicine, National Center for Biotechnology Information, Aug. 11, 2016, (11 pages).
CID 9567065, AQ-390/12597145, PubChem Compound Summary, NIH, U.S. Natl Library of Medicine, National Center for Biotechnology Information, Aug. 11, 2016, (11 pages).
CAS Registry No. 481682-91-1, which entered STN on Jan. 27, 2003.
CAS Registry No. 485371-82-2, which entered STN on Feb. 4, 2003.
CAS Registry No. 455301-78-7, which entered STN on Sep. 26, 2002.
CAS Registration No. 473428-25-0 Registry(STN) [online] Nov. 13, 2002 [date of search Jan. 26, 2017].
CAS Registration No. 478937-00-7 Registry(STN) [online] Jan. 14, 2003 [date of search Jan. 26, 2017].
CAS Registration No. 481698-76-4 Registry(STN) [online] Jan. 27, 2003 [date of search Jan. 26, 2017].
CAS Registration No. 481711-53-9 Registry(STN) [online] Jan. 27, 2003 [date of search Jan. 26, 2017].
CAS Registration No. 482285-08-5 Registry(STN) [online] Jan. 28, 2003 [date of search Jan. 26, 2017.
CAS Registration No. 482352-04-5 Registry(STN) [online] Jan. 28, 2003 [date of search . Jan. 26, 2017].
CAS Registration No. 502886-05-7 Registry(STN) [online] Apr. 14, 2003 [date of search Jan. 26, 2017].
CAS Registration No. 509102-00-5 Registry(STN) [online] May 2, 2003 [date of search Jan. 26, 2017].
CAS Registration No. 722476-42-8 Registry(STN) [online] Aug. 5, 2004 [date of search Jan. 26, 2017].
CAS Registration No. 728908-54-1 Registry(STN) [online] Aug. 19, 2004 [date of search Jan. 26, 2017].
CAS Registration No. 730256-75-4 Registry(STN) [online] Aug. 22, 2004 [date of search Jan. 26, 2017].
CAS Registration No. 730256-77-6 Registry(STN) [online] Aug. 22, 2004 [date of search Jan. 26, 2017].
CAS Registration No. 732264-56-17 Registry(STN) [online] Aug. 25, 2004 [date of search Jan. 26, 2017].
JPO Official Action for JP Pat. App. No. 2016-097054, dated Apr. 13, 2017 (9 pages) [with English Translation].
Lesyk et al., *New thiazolidones-4 with pyrazolone-5 substituent as the potential NSAIDs*, Bollettino Chimico Farmaceutico, 137(6):210-217 (1998).
Sakamoto et al., *Studies on Effects of Drugs upon Protoscoleces of Echinococcus granulosus in Vitro*, Memoirs of Faculty of Agriculture Kagoshima University, 15:125-30 (1979).
AU Patent Examination Report No. 1 for Application No. AU2013235425 dated Sep. 29, 2016 (13 pages).
Bernal, F. et al., "A stapled p53 helix overcomes HDMX-mediated suppression of p53", Cancer Cell 18(5):411-422 (2010).
Beroukhim, R. et al., "The landscape of somatic copy-number alteration across human cancers", Nature 463(7283):899-905 (2010).
Bilinski et al., Condensation of 4-R-thiosemicarbazones of Pyridine Aldehydes with α-halogenketone. I. Condensation of Nicotinaldehyde 4-R-thiosemicarbazones with Chloroacetone and ω-chloracetophenone, Annales Universitatis Mariae Curie-Sklodowska. Lublin, PL, 23(16)AA:107-115, Jan. 1, 1968 [With English Summary—See p. 9].

(56) References Cited

OTHER PUBLICATIONS

Bilinski, et al., *Condensation of 4-R-thiosemicarbazones of Pyridine Aldehydes with α-nalogen-ketones. II. Condensation of Isonicotinaldehyde 4-R-thiosemicarbazone with Chloroacetone and ω-chloroacetophenone*, Annales Universitatis Mariae Curie Skoldowska, Medi, Uniwersytet Marii Curie-Skodowskiej. Akademia Medyzna, Lublin, PL, 25(49)D:541-547, Jan. 1, 1970 [With English Summary—see p. 7].
CAS Registration No. 315698-78-3 Registry (STN) [online], Jan. 22, 2001, [searching date Oct. 27, 2014].
CAS Registration No. 794552-60-6 Registry (STN) [online], Dec. 8, 2004, [searching date Oct. 27, 2014].
CAS Registration No. 794552-61-7 Registry (STN) [online], Dec. 8, 2004,[searching date Oct. 27, 2014].
CAS Registry No. 473233-06-6, Reaxys Registry No. 23958590, which entered STN on Nov. 12, 2002.
CAS Registry No. 1013591-26-8; STN Entry Date Apr. 10, 2008; 5-[2-(cyclopropylimino)-2,3-dihydro-3-[[(2,3,4-trimethoxyphenyl)methylene]amino]-4-thiazolyl]-2-hydroxy-benzamide.
CAS Registry No. 473233-06-6; STN Entry Date Nov. 12, 2002; 4-[[[2-(cyclohexylimino)-4-(2-thienyl)-3(2H)-thiazolyl]imino]methyl]-1,2,3-benzenetriol.
CAS Registry No. 474791-96-3; STN Entry Date Dec. 2, 2002; 3-[[[2-(cyclohexylimino)-4-methyl-3(2H)-thiazolyl]imino]methyl]-1,2-benzenediol.
CAS Registry No. 474914-01-7; STN Entry Date Dec. 3, 2002; 2-(cyclohexylimino)-4-methyl-N-[(2,3,4-trimethoxyphenyl)methylene]-3(2H)-thiazolamine.
CAS Registry No. 479369-50-1 ; STN Entry Date Jan. 17, 2003; 2-(cyclohexylimino)-4-phenyl-N-[(2,4,5-trimethoxyphenyl)methylene]-3(2H)-thiazolamine.
CAS Registry No. 479387-53-6 ; STN Entry Date Jan. 17, 2003; 2-(cyclohexylimino)-N-[(2,4-dimethoxyphenyl)methylene]-4-methyl-3(2H)-thiazolamine.
CAS Registry No. 479700-04-4; STN Entry Date Jan. 22, 2003; 4-[[[2-(cyclohexylimino)-4-phenyl-3(2H)-thiazolyl]imino]methyl]-2,6-dimethoxy-phenol.
CAS Registry No. 491635-11-1; STN Entry Date Feb. 18, 2003; 2-(cyclohexylimino)-4-(2-thienyl)-N-[(3,4,5-trimethoxyphenyl)methylene]-3(2H)-thiazolamine.
CAS Registry No. 491643-99-3; STN Entry Date Feb. 18, 2003; 3-[[[2-(cyclohexylimino)-4-phenyl-3(2H)-thiazolyl]imino]methyl]-1,2-benzenediol.
CAS Registry No. 502565-41-5; STN Entry Date Apr. 10, 2003; 4-[[[2-(cyclohexylimino)-4-methyl-3(2H)-thiazolyl]imino]methyl]-2-methoxy-phenol.
CAS Registry No. 503006-71-1; STN Entry Date Apr. 15, 2003; 2-bromo-4-[[[2-(cyclohexylimino)-4-methyl-3(2H)-thiazolyl]imino]methyl]-6-methoxy-phenol.
CAS Registry No. 503290-13-9 ; STN Entry Date Apr. 17, 2003; 2-(cyclohexylimino)-4-methyl-N-[(2,4,5-trimethoxyphenyl)methylene]-3(2H)-thiazolamine.
CAS Registry No. 733042-52-9; STN Entry Date Aug. 26, 2004; 2-(cyclopropylimino)-4-[(4-methoxyphenyl)methylene]-3(2H)-thiazolamine.
CAS Registry No. 746606-31-5; STN Entry Date Sep. 17, 2004; 4-(5-bromo-2-thienyl)-2-(cyclopropylimino)-N-[(2,3,4-trimethoxyphenyl)methylene]-3(2H)-thiazolamine.
Chou, T.C., "Theoretical basis, experimental design, and computerized simulation of synergism and antagonism in drug combination studies", Pharmacol. Rev. 58(3):621-681 (2006).
Cohen et al., "A Competitive Stapled Peptide Screen Identifies a Selective Small Molecule that Overcomes MCL-1-Dependent Leukemia Cell Survival", Chem Biol., 19(9):1175-1186 (Sep. 2012).
Degterev, A. et al., "Identification of small-molecule inhibitors of interaction between the BH3 domain and Bcl-$x_L$", Nat Cell Biol 3:173-182 (2001).

Delaglio, F. et al., "NMRPipe: a multidimensional spectral processing system based on UNIX pipes", J Biomol NMR 6:277-293 (1995).
Enyedy, I.J. et al., "Discovery of small-molecule inhibitors of Bcl-2 through structure-based computer screening", J Med Chem 44:4313-4324 (2001).
EPO, Extended European Search Report for EP Application No. 16192483.2, dated Jan. 23, 2017 (11 pages).
EPO Extended European Search Report for EP App. No. 13763682.5, dated Mar. 10, 2016 (9 pages).
Freireich et al., "Quantitative Comparison of Toxicity of Anticancer Agents in Mouse, Rat, Hamster, Dog, Monkey, and Man", Cancer Chemother. Rep., 50(4):219 (1966).
Frenzel, A., et al., "Bcl2 family proteins in carcinogenesis and the treatment of cancer", Apoptosis 14(4):584-596 (2009).
Gandhi, L. et al., "Phase I study of Navitoclax (ABT-263), a novel Bcl-2 family inhibitor, in patients with small-cell lung cancer and other solid tumors", J Clin Oncol 29(7):909-916 (2011).
Gavathiotis et al., "Direct and selective small-molecule activation of proapoptotic BAX", Nat Chem Biol,, 8:639-645 (May 2012).
Grzesiek, S. et al., "The importance of not saturating water in protein NMR: application to sensitivity enhancement and NOE measurements", J Am Chem Soc 115:12593-12594 (1993).
Hünig et al., Umlagerungen in der Thiazolreihe, Journal Fuer Praktische Chemie (Leipzig), 8(5-6):264-278, Jun. 1, 1959 [With English translation of Abstract].
International Search Report and Written Opinion for PCT/US2013/031705, dated Jun. 25, 2013 (15 pages).
Johnson, B.A., "Using NMRView to visualize and analyze the NMR spectra of macromolecules", Methods Mol Biol., 278:313-352 (2004).
JPO Office Action for Japanese Patent App. No. 2012-551374, dated Jun. 2, 2015 (with English translation) (9 pages).
JPO Office Action issued in JP Patent Application No. 2012-551374, dated Nov. 11, 2014 with English Translation (13 pages).
Kang, M.H. et al., "Bcl-2 inhibitors: targeting mitochondrial apoptotic pathways in cancer therapy", Clin Cancer Res 15(4):1126-1132 (2009).
Kleinrok et al., Some Pharmacological characteristics of new derivatives of pyridine aldehyde hydrazones, Annales Universitatis Mariae Curie Sklodowska. Medi, Uniwersytet Marii Curie, Akademia Medyzna, Lublin, PL, 26(15)D:127-135, Jan. 1, 1971 [With English Summary—See pp. 8-9)
Llambi, F. et al., "Apoptosis and oncogenesis: give and take in the BCL-2 family", Curr Opin Genet Dev, 21(1):12-20 (2011).
Lovell, J.F. et al., "Membrane binding by tBid initiates an ordered series of events culminating in membrane permeabilization by Bax", Cell 135:1074-1084 (2008).
Marintchev, A., et al., "NMR methods for studying protein-protein interactions involved in translation initiation", Methods Enzymol 430:283-331 (2007).
Negrin et al., "In vivo-in vitro study of biodegradable methadone delivery systems", Biomaterials, 22(6):563-570 (2001).
Oltersdorf, T. et al., "An inhibitor of Bcl-2 family proteins induces regression of solid tumours", Nature 435:677-681 (2005).
Petros, A.M. et al., "Discovery of a potent and selective Bcl-2 inhibitor using SAR by NMR", Bioorg Med Chem Lett 20:6587-6591 (2010).
PubChem Compound [Online] AC1M621Y—Database accession No. CID 2340270, NCBI; Jul. 15, 2005, (12 pages).
PubChem Compound Database—509102-00-5, National Center for Biotechnology Information. CID 6848561, https://pubchem.ncbi.nlm.nih.gov/compound/6848561 (accessed Oct. 21, 2016).
PubChem Compound Database—MLS000774515, National Center for Biotechnology Information. CID 5894545, https://pubchem.ncbi.nlm.nih.gov/compound/5894545 (accessed Oct. 21, 2016).
PubChem Compound Summary—CID 2235899, ZINC02883560, NIH, U.S. Natl Library of Medicine, National Center for Biotechnology Information, Aug. 11, 2016, (11 pages).
PubChem Compound Summary—CID 22525618, NIH, U.S. Natl Library of Medicine, National Center for Biotechnology Information, Aug. 11, 2016, (11 pages).

(56) References Cited

OTHER PUBLICATIONS

PubChem Compound Summary—CID 24319562, STK981930, NIH, U.S. Natl Library of Medicine, National Center for Biotechnology Information, Aug. 11, 2016, (11 pages).
PubChem Compound Summary—CID 3318217, AC1MOCNT, NIH, U.S. Natl Library of Medicine, National Center for Biotechnology Information, Aug. 11, 2016, (11 pages).
PubChem Compound Summary—CID 5433262, STK215536, NIH, U.S. Natl Library of Medicine, National Center for Biotechnology Information, Aug. 11, 2016, (14 pages).
PubChem Compound Summary—CID 7728365, GNF-Pf-1078, NIH, U.S. Natl Library of Medicine, National Center for Biotechnology Information, Aug. 11, 2016, (14 pages).
PubChem Compound Summary—CID 9567065, AQ-390/12597145, NIH, U.S. Natl Library of Medicine, National Center for Biotechnology Information, Aug. 11, 2016, (11 pages).
PubChem Compound Summary—CID 9568012, ST50774387, NIH, U.S. Natl Library of Medicine, National Center for Biotechnology Information, Aug. 11, 2016, (11 pages).
PubChem Compound Summary—CID 9611934, F0808-0868, NIH, U.S. Natl Library of Medicine, National Center for Biotechnology Information, Aug. 11, 2016, (11 pages).
PubChem Database Compound [Online], NCBI; May 30, 2009, Database accession No. CID 42371696.
PubChem Database Compound [Online], NCBI; May 30, 2009, Database accession No. CID 42504827.
PubChem ZINC15913384, PubChem SID 59797118, PubChem CID: 6848561 (509102-00-5), Available Date: May 28, 2009. http://pubchem.ncbi.nlm.nih.gov/substance/59797118/version/1.
Remington's Pharmaceutical Sciences, 17th ed., Mack Publishing Company, Easton, Pa., 1985, p. 1418.
Roberts, A.W. et al., "Substantial susceptibility of chronic lymphocytic leukemia to BCL2 inhibition: Results of Phase 1 study of Navitoclax (ABT-263) in patients with relapsed or refractory disease", J Clin Oncol., 30(5):488-496 (2011).
Shamas-Din, A., et al., "BH3-only proteins: Orchestrators of apoptosis", Biochim Biophys Acta 1813:508-520 (2011).
Souers et al., "ABT-199, a potent and selective BCL-2 inhibitor, achieves antitumor activity while sparing platelets", Nat Med 19:202-208 (2013).
Stewart, M.L., et al., "The MCL-1 BH3 helix is an exclusive MCL-1 inhibitor and apoptosis sensitizer", Nature Chem Biol 6:595-601 (2010).
Suzuki, M., et al., "Structure of Bax: coregulation of dimer formation and intracellular localization", Cell 103:645-654 (2000).
Traverso, Sul comportamento di alcune 3-amino-4-metil-tiazolon-2-imidi nei confronti delle aldeidi aromatiche, Gazzetta Chimica Ital, Societa Chimica Italiana, IT, 85:956-964, Jan. 1, 1955 [With English translation of Abstract].
Tsujimoto, Y., et al., "Cloning of the chromosome breakpoint of neoplastic B cells with the t(14;18) chromosome translocation", Science 226:1097-1099 (1984).
Tsujimoto, Y., et al., "Involvement of the bcl-2 Gene in Human Follicular Lymphoma", Science 228:1440-1443 (1985).
Tzung, S.P. et al., "Antimycin A mimics a cell-death-inducing Bcl-2 homology domain 3", Nat Cell Biol 3:183-191 (2001).
Vaux, D.L., et al. "Bcl-2 gene promotes haemopoietic cell survival and cooperates with c-myc to immortalize pre-B cells", Nature 335:440-442 (1988).
Walensky, L.D. et al., "BAX unleashed: the biochemical transformation of an inactive cytosolic monomer into a toxic mitochondrial pore", Trends Biochem Sci 36:642-652 (2011).
Wang, J.L. et al., "Structure-based discovery of an organic compound that binds Bcl-2 protein and induces apoptosis of tumor cells", Proc Natl Acad Sci USA 97:7124-7129 (2000).
Wilen, S.H., "Tables of Resolving Agents and Optical Resolutions", p. 268 (E.L. Eliel, Ed., Univ. of Notre Dame Press, Note Dame, IN 1972).
Wilen, S.H., et al., "Strategies in Optical Resolutions", Tetrahedron 33:2725 (1977).
Wilson, W.H. et al., "Safety, Pharmacokinetics, Pharmacodynamics, and Activity of Navitoclax, a Targeted High Affinity Inhibitor of BCL-2, in Lymphoid Malignancies", Lancet Oncol 11(12):1149-1159 (2010).
Yecies, D., et al., "Acquired resistance to ABT-737 in lymphoma cells that up-regulate MCL-1 and BFL-1", Blood 115:3304-3313 (2010).
Yethon, J.A., et al., "Interaction with a membrane surface triggers a reversible conformational change in Bax normally associated with induction of apoptosis", J Biol Chem 278:48935-48941 (2003).
Yoon et al. "High-Throughput Screening-Based Identification of Paramyxovirus Inhibitors", Journal of Biomolecular Screening, 13(7):591-608 (2008).
Youle, R.J. et al., "The BCL-2 protein family: opposing activities that mediate cell death", Nat Rev Mol Cell Biol 9:47-59 (2008).
Zhai, D., et al., "Comparison of chemical inhibitors of antiapoptotic BCL-2 family proteins", Cell Death Diff. 13:1419-1421 (2006).
CAS Registration No. 1164463-47-1 Registry STN [online], https://stneasy.cas.org/tmp/20170518/79995-0183252827-200/236318139.clean.html May 18, 2017.
CAS Registry No. 1164469-80-0 Registry STN [online], https://stneasy.cas.org/tmp/20170518/79995-0183252827-200/218673_776.clean.html May 18, 2017.
CAS Registry No. 1164475-30-2 Registry STN [online], https://stneasy.cas.org/tmp/20170518/79995-0183252827-200/128995690.clean.html May 18, 2017.
CAS Registry No. 1164482-47-6 Registry STN [online], https://stneasy.cas.org/tmp/20170518/79995-0183252827-200/69065964.clean.html May 18, 2017.
CAS Registry No. 1164482-52-3 Registry STN [online] https://stneasy.cas.org/tmp/20170518/79995-0183252827-200/329817829_.clean.html May 18, 2017.
CAS Registry No. 1164482-75-0 Registry STN [online] https://stneasy.cas.org/tmp/20170518/79995-0183252827-200/350996572.clean.html May 18, 2017.
CAS Registry No. 1164502-80-0 Registry STN [online] https://stneasy.cas.org/tmp/20170518/79995-0183252827-200/688640520.clean.html May 18, 2017.
CAS Registry No. 1164503-48-3 Registry STN [online] https://stneasy.cas.org/tmp/20170518/79995-0183252827-200/30907460_1_.clean.html May 18, 2017.
CAS Registry No. 1164508-84-2 Registry STN [online] https://stneasy.cas.org/tmp/20170518/79995-0183252827-200/27945708.clean.html May 18, 2017.
CAS Registry No. 1164510-53-5 Registry STN [online] https://stneasy.cas.org/tmp/20170518/79995-0183252827-200/7_18275408.clean.html May 18, 2017.
CAS Registry No. 1164510-72-8 Registrystn [online] https://stneasy.cas.org/tmp/20170518/79995-0183252827-200/7296445_.clean.html May 18, 2017.
CAS Registry No. 1164513-93-2 Registry STN [online] https://stneasy.cas.org/tmp/20170518/79995-0183252827-200/267113598.clean.html May 18, 2017.
CAS Registry No. 1164516-60-2 Registry STN [online] https://stneasy.cas.org/tmp/20170518/79995-0183252827-200/520099716.clean.html May 18, 2017.
CAS Registry No. 1164531-53-6 Registry STN [online] https://stneasy.cas.org/tmp/20170518/79995-0183252827-200/120229496.clean.html May 18, 2017.
CAS Registry No. 1164541-91-6 Registry STN [online] https://stneasy.cas.org/tmp/20170518/79995-0183252827-200/660593334.clean.html May 18, 2017.
CAS Registry No. 1164543-50-3 Registry STN [online] https://stneasy.cas.org/tmp/20170518/79995-0183252827-200/418035717_.clean.html May 18, 2017.
CAS Registry No. 1164545-71-4 Registry STN [online] https://stneasy.cas.org/tmp/20170518/79995-0183252827-200/562824943_.clean.html May 18, 2017.
CAS Registry No. 1164546-81-9 Registry STN [online] https://stneasy.cas.org/tmp/20170518/79995-0183252827-200/204180515_.clean.html May 18, 2017.

(56) References Cited

OTHER PUBLICATIONS

CAS Registry No. 1164551-66-9 Registry STN [online] https://stneasy.cas.org/tmp/20170518/79995-0183252827-200/93312748.clean.html May 18, 2017.
CAS Registry No. 1164554-95-3 Registry STN [online] https://stneasy.cas.org/tmp/20170518/79995-0183252827-200/160120168.clean.html May 18, 2017.
CAS Registry No. 1164556-04-0 Registry STN [online] https://stneasy.cas.org/tmp/20170518/79995-0183252827-200/410250913_.clean.html May 18, 2017.
CAS Registry No. 1164556-15-3 Registry STN [online] https://stneasy.cas.org/tmp/20170518/79995-0183252827-200/380019195_.clean.html May 18, 2017.
CAS Registry No. 1164557-96-3 Registry STN [online] https://stneasy.cas.org/tmp/20170518/79995-0183252827-200/17848421_.clean.html May 18, 2017.
CAS Registry No. 1164558-61-5 Registry STN [online] https://stneasy.cas.org/tmp/20170518/79995-0183252827-200/330861997_.clean.html May 18, 2017.
CAS Registry No. 1164478-76-5 Registry STN [online] https://stneasy-japan.cas.org/tmp/20170521/155962-1981728486-300/518250663.clean.html May 22, 2017.
CAS Registry No. 1010960-60-7; STN Entry Date Mar. 30, 2008; 4-[2-(cyclohexylimino)-2,3-dihydro-3-((2-pyridinylmethylene)amino]-4-thiazolyl]-1,3-benzenediol, 1 page.
CAS Registry No. 1062109-16-3; STN Entry Date Oct. 16, 2008; 5-[(2Z)-2-(cyclopropylimino)-3-[(E)-[(4-fluorophenyl)methylene]amino]-2,3-dihydro-4-thiazolyl]-2-hydroxy-benzamide, 1 page.
CAS Registry No. 1177738-13-4; STN Entry Date Aug. 30, 2009; (2Z)-4-methyl-2-(cyclohexylimino)-N((2,4-dichlorophenyl)methylene]-3(2H)-thiazolamine, 1 page.
CAS Registry No. 452280-05-6; STN Entry Date Sep. 18, 2002; 2-(cyclohexylimino)-4-(2-furanyl)-N-(2-furanylmethylene)-3(2H)-thiazolamine, 1 page.
CAS Registry No. 455313-09-4; STN Entry Date Sep. 26, 2002; N-(1,3-benzodioxol-5-ylmethylene)-2-(cyclohexylimino)-4-methyl-3(2H)-thiazolamine, 1 page.
CAS Registry No. 455322-89-1; STN Entry Date Sep. 26, 2002; 4-[[[2-(cyclohexylimino)-4-(2-furanyl)-3(2H)-thiazolyl]imino]methyl]-1,2,3-benzenetriol, 1 page.
CAS Registry No. 473581-27-0; STN Entry Date Nov. 14, 2002; 4-[[[2-(cyclohexylimino)-4-methyl-3(2H)thiazolyl]imino]methyl]-2-ethoxy-phenol, 1 page.
CAS Registry No. 478856-87-0; STN Entry Date Jan. 13, 2003; 2-(cyclohexylimino)-4-methyl-N(phenylmethylene)-3(2H)-thiazolamine, 1 page.
CAS Registry No. 479363-09-2; STN Entry Date Jan. 17, 2003; 3-[[[2-(cyclohexylimino)-4-(2,4-dimethoxyphenyl)-3(2H)-thiazolyl]imino]methyl]-phenol, 1 page.
CAS Registry No. 482348-78-7; STN Entry Date Jan. 28, 2003; 4-[[[2-(cyclohexylimino)-4-(2,4-dimethoxyphenyl)-3(2H)-thiazolyl]imino]methyl]-1,2,3-benzenetriol, 1 page.
CAS Registry No. 485371-71-9; STN Entry Date Feb. 4, 2003; N-(1,3-benzodioxol-5-ylmethylene)-2-(cyclohexyl imino)-4-(2,5-dimethoxyphenyl)-3(2H )-thiazolamine, 1 page.
CAS Registry No. 485373-60-2; STN Entry Date Feb. 4, 2003; 4-[[[2-(cyclohexylimino)-4-(2-furanyl)-3(2H)-thiazolyl]imino]methyl]-1,2-benzenediol, 1 page.
CAS Registry No. 485771-08-2; STN Entry Date Feb. 5, 2003; 2-(cyclohexylimino)-4-(3,4-dimethylphenyl)-N-(1 H-pyrrol-2-ylmethylene)-3(2H)-thiazol, 1 page.
CAS Registry No. 502873-17-8; STN Entry Date Apr. 14, 2003; 4-[[[2-(cyclohexylimino)-4-(3,4,5-trimethoxyphenyl)-3(2H)-thiazolyl]imino]methyl]-1,2,3-benzenetriol, 1 page.
CAS Registry No. 502982-98-1; STN Entry Date Apr. 15, 2003; 4-[[[2-(cyclohexylimino)-4-(2,5-dichlorophenyl)-3(2H)-thiazolyl]imino]methyl]-1,2,3-benzenetriol, 1 page.
CAS Registry No. 502991-49-3; STN Entry Date Apr. 15, 2003; 4-(([2-(cyclohexylimino)-4-(2,4-dichlorophenyl)-3(2H)-1,2,3-benzenetriol, 1 page.
CAS Registry No. 503022-28-4; STN Entry Date Apr. 15, 2003; 4-(([2-(cyclohexylimino)-4-(3,4-dichlorophenyl)-3(2H)-thiazolyl]imino]methyl]-1,2,3-benzenetriol, 1 page.
CAS Registry No. 503145-61-7; STN Entry Date Apr. 16, 2003; 2-(cyclohexylimino)-4-(3,4-dimethylphenyl )-N-(2-th ienyl methylene )-(2H )-thiazolamine, 1 page.
CAS Registry No. 503297-48-1; STN Entry Date Apr. 17, 2003; 4-(([2-(cyclohexylimino)-4-(2,4-dichlorophenyl)-3(2H)-thiazolyl]imino]methyl]-1,3-benzenediol, 1 page.
CAS Registry No. 507457-35-4; STN Entry Date Apr. 30, 2003; 2-(cyclohexylimino)-N-(4-pyridinylmethylene)-4-(3,4,5-trimethoxyphenyl)-3(2H)-thiazolamine, 1 page.
CAS Registry No. 733043-64-6; STN Entry Date Aug. 26, 2004; 4-[[[2-(cyclohexylimino)-4-(2-furanyl)-3(2H)-thiazolyl]imino]methyl]-benzoic acid methyl ester, 1 page.
Examination Report No. 2 for Australian Application No. 2013235425, dated Jun. 22, 2017, 13 pages.
AU Examination Report No. 1 for Australian App. No. 2011210567, dated Jan. 29, 2010 (5 pages).
EPO Examination Report for EP App. No. 11737834.9 dated Sep. 20, 2017 (4 pages).
EPO Examination Report for EP App. No. 11737834.9 dated Jan. 2, 2017 (4 pages).
EPO Examination Report for EP App. No. 13763682.5 dated Mar. 14, 2017 (7 pages).
JPO Official Action for JP App. No. 2016-097054 dated Apr. 13, 2017 (10 pages) [With English Translation].
U.S. Appl. No. 14/386,747, filed Sep. 19, 2014, Walensky.

* cited by examiner 1) 1589P01 (Class G)   2) 1597G03 (Class E)   3) 1655B03 (Class E)

4) 1614B11 (Class E)   5) 1654L06 (Unclass.)   6) 1621I22 (Class I)

TINQESCIEPLAESITDVLVR

| Sample | Cys-fragment MW |
|---|---|
| Unmodified MCL-1ΔNΔC | 2330.7 Da |
| 1923A19-modified MCL-1ΔNΔC | 2777.4 Da |

FIG. 3A, cont.
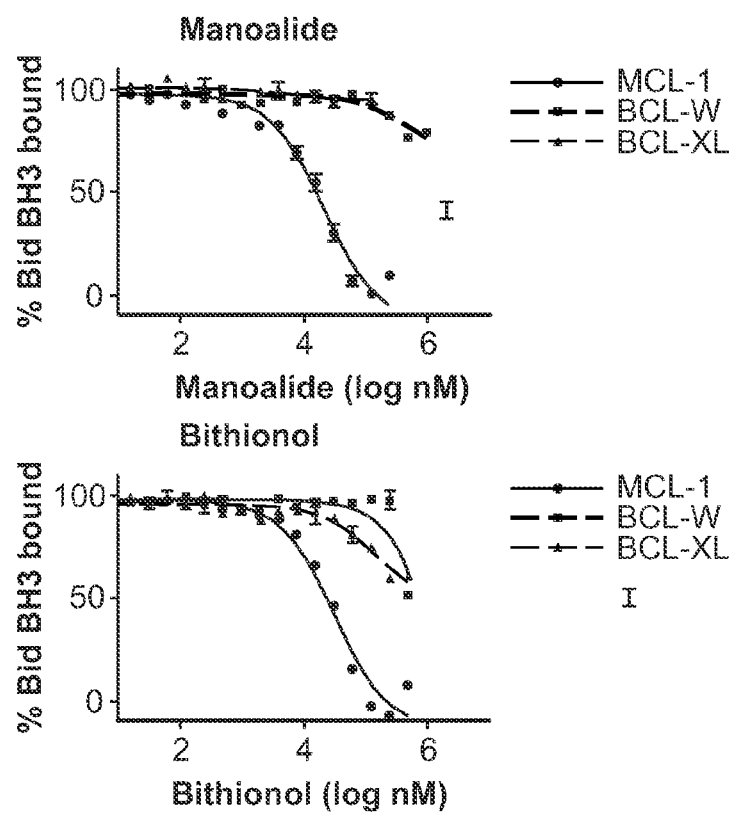

FIG. 3B

| Bioactive | Compound ID | MCL-1ΔNΔC | BCL-X$_L$ΔC | BCL-WΔC |
|---|---|---|---|---|
| Celestrol | 1923A13 | 0.2 ± 0.5 | 32 ± 9 | 19 ± 5 |
| U73122 | 1792N03 | 0.2 ± 0.5 | > 100 | > 100 |
| Hexachlorophene | 1920D07 | 0.9 ± 0.2 | 3.8 ± 1.0 | 12 ± 10 |
| Gossypol | 1570G15 | 1.3 ± 0.2 | 3.9 ± 0.9 | 1.7 ± 0.4 |
| Manoalide | 1792M11 | 2.8 ± 0.9 | > 100 | 50 ± 30 |
| Bithionol | 1920I03 | 3.2 ± 0.7 | 14 ± 10 | > 100 |

| < 5 µM | > 5 µM, < 25 µM | > 25 µM |
|---|---|---|
|  |  |  |

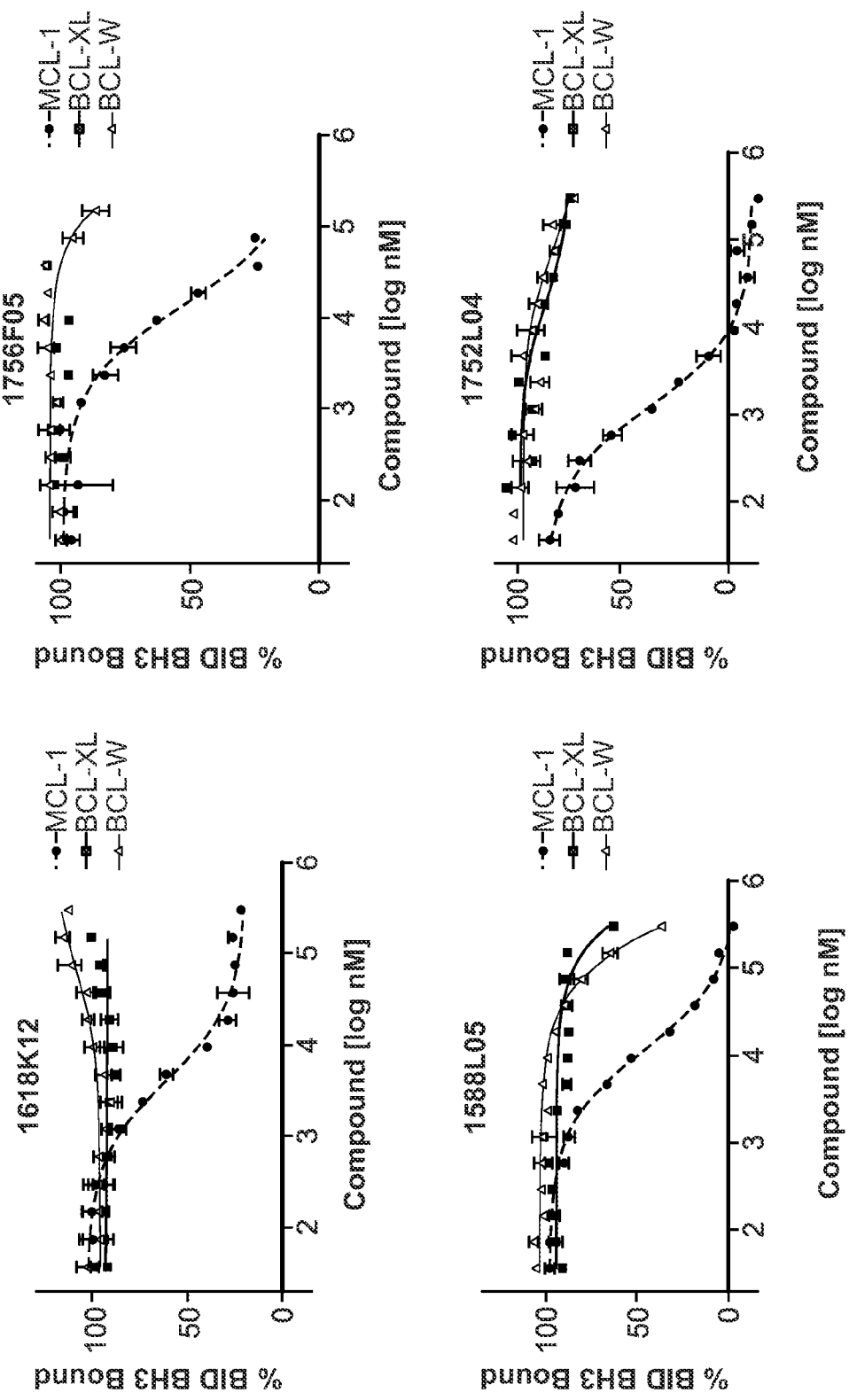
FIG. 4A, cont.

FIG. 4B

| Compound ID | Class | MCL-1ΔNΔC | BCL-X$_L$ΔC | BCL-WΔC |
|---|---|---|---|---|
| 1673N01 | A | 0.014 ± 0.009 | > 50 | > 50 |
| 1644L16 | D | 16 ± 8 | > 100 | > 100 |
| 1612H17 | E | 0.26 ± 0.09 | > 75 | > 75 |
| 1618N18 | F | 1.3 ± 0.2 | > 100 | > 100 |
| 1618K12 | G | 6 ± 3 | > 100 | > 100 |
| 1588L05 | H | 11.3 ± 1.2 | > 100 | > 100 |
| 1756F05 | I | 12 ± 5 | > 100 | > 100 |
| 1752D04 | J | 1.2 ± 0.3 | > 100 | > 100 |

| < 5 μM |
| > 5 μM, < 25 μM |
| > 25 μM |

| $R_1$ | $R_2$ | $EC_{50}$ |
|---|---|---|
| HN—N, S (1H-1,2,4-triazole-thiol) | p-tolyl | 14 ± 9 nM |
| HN—N, S (1H-1,2,4-triazole-thiol) | 4-F-phenyl | 100 ± 80 nM |
| Cl | p-tolyl | 3.2 ± 1.6 μM |
| S-CN | p-tolyl | 3.8 ± 0.8 μM |
| S-CH2-(4-methylphenyl) | p-tolyl | > 10 μM |

| R₁ | R₂ | EC₅₀ |
|---|---|---|
| H |  4-OMe, 3-NO₂ phenyl | 1.5 ± 1.0 μM |
| H |  phenyl | 1.7 ± 0.4 μM |
| H |  2-Me, 4-CO₂H phenyl | 2.2 ± 0.5 μM |
| H |  2-Me, 4-NHAc phenyl | 2.9 ± 0.7 μM |
| H |  4-OEt phenyl | 3.1 ± 1.5 μM |
| H |  4-F phenyl | 3.6 ± 2.6 μM |
| H |  4-Me phenyl | 4.8 ± 3.0 μM |
| H |  4-tBu phenyl | > 10 μM |

| $R_1$ | $R_2$ | $R_3$ | $EC_{50}$ |
|---|---|---|---|
| $CH_3$ | 4-hydroxyphenyl | $CH_3$ | > 40 μM |
| $CH_3$ | 3,4-dihydroxyphenyl | $CH_3$ | > 40 μM |
| $CH_3$ | 3,5-dihydroxyphenyl | $CH_3$ | > 40 μM |
| $CH_3$ | 2,3,4-trihydroxyphenyl | $CH_3$ | > 40 μM |
| $CH_2CH_3$ | 2,3,4-trihydroxyphenyl | $CH_3$ | > 40 μM |
| $CH_3$ | 2-iodophenyl | $CH_3$ | > 40 μM |
| $CH_3$ | 3,4-dihydroxyphenyl | 3-furyl | > 40 μM |
| benzyl | 2,4-dihydroxyphenyl | 3-furyl | > 40 μM |
| $CH_3$ | 4-hydroxyphenyl | 4-(difluoromethoxy)phenyl | > 40 μM |

FIG. 4D Cont.

| R₁ | R₂ | R₃ | EC₅₀ |
|---|---|---|---|
| cyclohexyl | 3,4-diOH-phenyl (OH, OH, OH) | CH₃ | 1.2 ± 0.3 μM |
| iPr | 3,4-diOH-phenyl (OH, OH, OH) | 3-thienyl | 1.6 ± 0.4 μM |
| CH₃ | 3,4-diOH-phenyl (OH, OH, OH) | 3,4-dimethylphenyl | 3.1 ± 0.3 μM |
| CH₃ | 3,4-diOH-phenyl (OH, OH, OH) | 2-fluorophenyl | 4.0 ± 0.8 μM |
| CH₃ | 3,4-diOH-phenyl (OH, OH, OH) | 3-thienyl | 4.2 ± 0.8 μM |
| CH₃ | 3,4-diOH-phenyl (OH, OH, OH) | 3,4-dichlorophenyl | 5.6 ± 1.5 μM |
| nPr | 3,4-diOH-phenyl (OH, OH, OH) | CH₃ | 9.5 ± 4.0 μM |
| 4-fluorophenyl | 3,4-diOH-phenyl (OH, OH) | benzoxazinone | 12.0 ± 3.0 μM |
| CH₃ | 3,4-diOH-phenyl (OH, OH) | 4-fluorophenyl | ~15 μM |

FIG. 5C

| Combination Index Values (*CalcuSyn analysis*) | | | | | |
|---|---|---|---|---|---|
| Bioactive | Compound ID | $EC_{50}$ | $EC_{75}$ | $EC_{90}$ | Synergy |
| Celastrol | 1923A19 | 0.366 | 0.279 | 0.241 | ++++ |
| Gossypol | 1570G15 | 0.507 | 0.475 | 0.561 | +++ |
| Bithionol | 1920I03 | 0.574 | 0.574 | 0.661 | +++ |
| Manoalide | 1792M11 | 0.635 | 0.592 | 0.576 | +++ |
| U73122 | 1792N03 | 0.911 | 0.782 | 0.686 | ++ |

FIG. 5D

| Combination Index Values (*CalcuSyn analysis*) | | | | | |
|---|---|---|---|---|---|
| Compound ID | Class | $EC_{50}$ | $EC_{75}$ | $EC_{90}$ | Synergy |
| 1585I05 | A | 0.850 | 0.568 | 0.389 | +++ |
| 1644L14 | D | 1.110 | 0.314 | 0.090 | +++ |
| 1612H17 | E | 0.687 | 0.640 | 0.682 | ++ |
| 1789N21 | F | 0.667 | 0.574 | 0.599 | ++ |
| 1784D04 | H | 0.341 | 0.411 | 0.504 | +++ |
| 1586C04 | I | 0.332 | 0.417 | 0.527 | +++ |
| 1754M20 | J | 0.395 | 0.417 | 0.477 | +++ |

SMALL MOLECULES FOR THE MODULATION OF MCL-1 AND METHODS OF MODULATING CELL DEATH, CELL DIVISION, CELL DIFFERENTIATION AND METHODS OF TREATING DISORDERS

This application is a divisional and claims priority, of co-pending U.S. application Ser. No. 13/576,116, filed Jul. 30, 2012 and having a 371 completion date of Oct. 22, 2012, which is a U.S. National Stage application, and claims priority of International Application No. PCT/US2011/023220, filed Jan. 31, 2011, which claims priority of U.S. Provisional Application Ser. No. 61/299,803, filed Jan. 29, 2010. The contents of all of the prior applications are incorporated herein by reference in their entirety.

STATEMENT REGARDING FEDERALLY SPONSORED RESEARCH OR DEVELOPMENT

This invention was made with government support under grant number P01CA92625 awarded by The National Institutes of Health. The government has certain rights in the invention.

BACKGROUND OF THE INVENTION

Beginning with the discovery of BCL-2 at the t14;18 chromosomal breakpoint of follicular lymphoma[1-3], the anti-apoptotic members of the BCL-2 family have emerged as key pathogenic proteins in human diseases characterized by unchecked cellular survival, such as cancer and autoimmunity. A series of anti-apoptotic proteins including BCL-2, BCL-$X_L$, BCL-w, MCL-1, BFL1/A1, and BCL-B promote cellular survival by trapping the critical apoptosis-inducing BCL-2 homology domain 3 (BH3) α-helix of pro-apoptotic BCL-2 family members[4]. Cancer cells exploit this physiologic survival mechanism through anti-apoptotic protein overexpression, establishing an apoptotic blockade that secures their immortality. To overcome this potentially fatal resistance mechanism, a pharmacologic quest is underway to develop targeted therapies that bind and block BCL-2 family survival proteins.

Anti-apoptotic proteins contain a hydrophobic binding pocket on their surface that engages BH3 α-helices[4,5]. Because Nature's solution to anti-apoptotic targeting involves selective interactions between BH3 death domains and anti-apoptotic pockets[6,7], molecular mimicry of the BH3 α-helix has formed the basis for developing small molecule modulators of anti-apoptotic proteins[8-10]. Promising compounds undergoing clinical evaluation, such as ABT-263[11], obatoclax[9], and AT-101[12], each target three or more anti-apoptotic proteins. The development of more precise inhibitors that target individual anti-apoptotic proteins remains a significant challenge due to the often subtle differences among BH3-binding pockets. Reminiscent of the long-term goals in kinase therapeutics, anti-apoptotic inhibitors with greater specificity would provide finely-tuned therapies to treat distinct diseases while potentially avoiding unwanted side-effects, such as those observed for ABT-263[11] and AT-101[13]. In addition, such compounds would serve as invaluable research tools to dissect the differential biological functions of anti-apoptotic proteins.

The specificity of anti-apoptotic proteins for BH3 domains is conferred by the topography of the canonical binding groove and the distinctive amino acid composition of the interacting BH3 helix. Whereas some BH3 domains, such as that of pro-apoptotic BIM, can tightly engage all anti-apoptotic pockets, others are more selective like the BAD BH3 that binds BCL-2, BCL-$X_L$, and BCL-w and the NOXA BH3 that targets MCL-1 and BFL1/A1[6]. The differential binding capacity of BH3 domains and their mimetics is clinically relevant, as exemplified by the close relationship between inhibitor binding spectrum and biological activity. For example, ABT-737, the prototype small molecule BH3 mimetic modeled after the BH3 domain of BAD, was designed to specifically target BCL-2 and BCL-$X_L$[10], and induces apoptosis in select cancers that are driven by these proteins[14-16]. However, ABT-737 fails to show efficacy against cancer cells that overexpress MCL-1, as this anti-apoptotic lies outside the molecule's binding spectrum[15-17]. In an effort to overcome the challenge of designing precision small molecules to selectively target interaction surfaces that are comparatively large and more complex, we investigated whether Nature's selective BH3 domains could be used to rapidly identify precise small molecule modulators.

The development of precise inhibitors for discrete anti-apoptotic BCL-2 family proteins implicated in pathologic cell survival remains a formidable but pressing challenge. Such compounds would provide finely-tuned molecular probes to study and treat human diseases driven by specific anti-apoptotic blockades. For example, anti-apoptotic MCL-1 has emerged as a major resistance factor in cancer. MCL-1 overexpression has been linked to the pathogenesis of a variety of refractory cancers, including multiple myeloma[18,19], acute myeloid leukemia[16], melanoma[20], and poor prognosis breast cancer[21]. MCL-1 exerts its pro-survival activity at the mitochondrial outermembrane where it neutralizes pro-apoptotic proteins such as NOXA, PUMA, BIM, and BAK. The critical role of MCL-1 in selective apoptotic resistance has been highlighted by the sensitizing effects of small interfering RNAs that downregulate MCL-1 protein levels[22,23].

Despite the formidable challenges associated with developing precise small molecule modulators of biomedically relevant protein targets, the identification of novel and selective small molecules modulators of MCL-1 is described herein.

BRIEF SUMMARY OF THE INVENTION

One embodiment of this invention encompasses a compound of the formula:

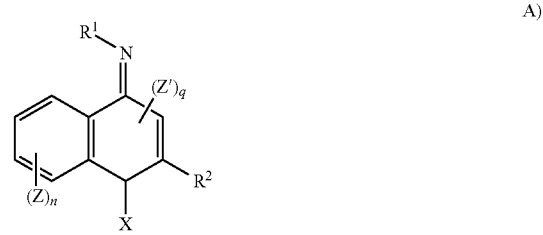

A)

Wherein:
X is =O or —O—$R^3$;
$R^1$ is substituted or unsubstituted aryl, substituted or unsubstituted heteroaryl, substituted or unsubstituted cycloalkyl, substituted or unsubstituted heterocycloalkyl, —S—$R^{2a}$, —$SO_2$—$R^{2a}$;
$R^2$ is hydrogen, halogen, —O—$R^{2a}$, —NH—$R^{2a}$, —S—CN, —S—$R^{2a}$, —S—$CH^2$—$R^{2a}$ or —$SO_2$—$R^{2a}$;

$R^{2a}$ is $C_1$-$C_8$ alkyl, substituted or unsubstituted aryl, substituted or unsubstituted heteroaryl, substituted or unsubstituted cycloalkyl, or substituted or unsubstituted heterocycloalkyl;

and $R^3$ is hydrogen, $C_1$-$C_5$ alkyl substituted or unsubstituted aryl, substituted or unsubstituted heteroaryl, substituted or unsubstituted cycloalkyl, or substituted or unsubstituted heterocycloalkyl; or

B)

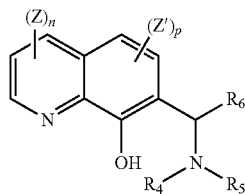

wherein:
$R^4$ and $R^5$ are independently hydrogen, substituted or unsubstituted aryl, substituted or unsubstituted heteroaryl, substituted or unsubstituted cycloalkyl, or substituted or unsubstituted heterocycloalkyl or are taken together to form a 5-7 membered, optionally substituted, heteroaryl or heterocycloalkyl, provided that no more than one of $R^4$ and $R^5$ is hydrogen;

And $R^6$ is substituted or unsubstituted aryl, substituted or unsubstituted heteroaryl, substituted or unsubstituted cycloalkyl, or substituted or unsubstituted heterocycloalkyl; or

C)

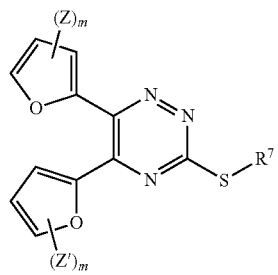

Wherein $R^7$ is CH2-CO—$R^{7a}$; —$CH_2$—NH—$SO_2$—$R^{7a}$;
and $R^{7a}$ is substituted or unsubstituted aryl, substituted or unsubstituted heteroaryl, substituted or unsubstituted cycloalkyl, or substituted or unsubstituted heterocycloalkyl; or

D)

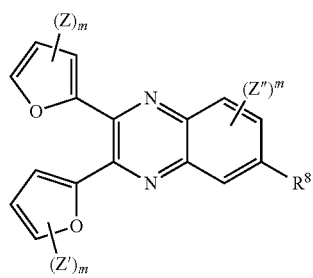

Wherein $R^8$ is is —CO—$R^{8a}$; —CO—NH—$(CH_2)_n$—$R^{8a}$; —CO—$CH_2$—$R^{8a}$, —NH—CO—NH—$R^{8a}$; —NH—$SO_2$—NH—$R^{8a}$; or —NH—CO—$R^{8a}$; —NH—$SO_2$—$R^{8a}$ and $R^{8a}$ is substituted or unsubstituted aryl, substituted or unsubstituted heteroaryl, substituted or unsubstituted cycloalkyl, or substituted or unsubstituted heterocycloalkyl; or

E)

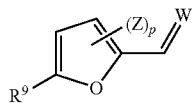

wherein $R^9$ is hydrogen, $C_1$-$C_6$ alkyl, $C_2$-$C_6$ alkeynyl, $C_2$-$C_6$ alkynyl, —$NH_2$, —$NHR^{9a}$, —$NR^{9a}R^{9b}$, —COH, —$COR^{9a}$, —COOH, or —$COOR^{9a}$;

$R^{9a}$ and $R^{9b}$ are independently $C_1$-$C_6$ alkyl, $C_2$-$C_6$ alkeynyl, $C_2$-$C_6$ alkynyl, substituted or unsubstituted aryl, substituted or unsubstituted heteroaryl, substituted or unsubstituted cycloalkyl, or substituted or unsubstituted heterocycloalkyl W is
$R^{10}$,
—CO—$R^{10}$,
—CO—NH—$(CH_2)_n$—$R^{10}$,
—CO—NH—CO—NH—$(CH_2)_n$—$R^{10}$,
—CO—NH—SO—NH—$(CH_2)_n$—$R^{10}$,
—SO—$(CH_2)_n$—$R^{10}$,
—SO—NH—$(CH_2)_n$—$R^{10}$,
—SO—NH—CO—NH—$(CH_2)_n$—$R^{10}$,
—SO—NH—SO—NH—$(CH_2)_n$—$R^{10}$, or
the group

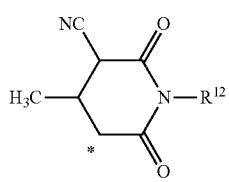

wherein * represents the point of attachment;
$R^{10}$ is Z or substituted or unsubstituted aryl, substituted or unsubstituted heteroaryl, substituted or unsubstituted cycloalkyl, or substituted or unsubstituted heterocycloalkyl;

$R^{12}$ is Z or hydrogen, $C_1$-$C_6$ alkyl or —$(CH_2)_n$—$R^{12a}$, $R^{12a}$ is Z or substituted or unsubstituted aryl, substituted or unsubstituted heteroaryl, substituted or unsubstituted cycloalkyl, or substituted or unsubstituted heterocycloalkyl; or

F)

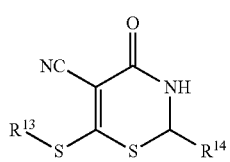

wherein
$R^{13}$ is $C_1$-$C_8$ alkyl, $C_2$-$C_8$ alkenyl, $C_2$-$C_8$ alkynyl, or $C_1$-$C_6$ alkoxy, and R$^{14}$ is substituted or unsubstituted aryl, substituted or unsubstituted heteroaryl, substituted or unsubstituted cycloalkyl, or substituted or unsubstituted heterocycloalkyl wherein R$^{14}$ may be further substituted by Z; or

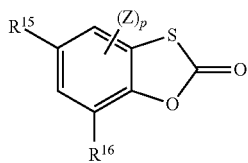

G)

wherein

R15 is hydrogen, hydroxyl, halogen, —CO—(CH$_2$)$_n$—R$^{15a}$, —CO—NH—(CH$_2$)$_n$—R$^{15a}$, —CO—NH—CO—NH—(CH$_2$)$_n$—R$^{15a}$, —CO—NH—SO—NH—(CH$_2$)$_n$—R$^{15a}$, NH—CO—(CH$_2$)$_n$—R$^{15a}$, NH—CO—NH—(CH$_2$)$_n$—R$^{15a}$, —SO—(CH$_2$)$_n$—R$^{15a}$, —SO—NH—(CH$_2$)$_n$—R$^{15a}$, —SO—NH—CO—NH—(CH$_2$)$_n$—R$^{15a}$, —SO—NH—SO—NH—(CH$_2$)$_n$—R$^{15a}$, or —NH—SO$_2$—R$^{15a}$; alkyl C1-C8-R15a R$^{15a}$ is substituted or unsubstituted aryl, substituted or unsubstituted heteroaryl, substituted or unsubstituted cycloalkyl, or substituted or unsubstituted heterocycloalkyl;

and R$^{16}$ is hydrogen, halogen, hydroxyl or substituted or unsubstituted aryl, substituted or unsubstituted heteroaryl, substituted or unsubstituted cycloalkyl, or substituted or unsubstituted heterocycloalkyl; or

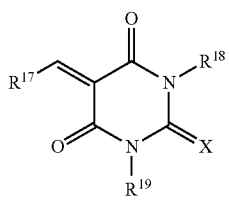

H)

wherein

X is O or S;

R$^{17}$ is substituted or unsubstituted aryl, substituted or unsubstituted heteroaryl, substituted or unsubstituted cycloalkyl, or substituted or unsubstituted heterocycloalkyl, wherein R$^{17}$ may be further substituted by Z;

R$^{18}$ is hydrogen, C$_1$-C$_8$ alkyl, C$_2$-C$_8$ alkenyl, C$_2$-C$_3$ alkynyl, or C$_1$-C$_6$ alkoxy, wherein R$^{18}$ may be further substituted by Z;

and R$^{19}$ is hydrogen, C$_1$-C$_8$ alkyl, C$_2$-C$_8$ alkenyl, C$_2$-C$_8$ alkynyl, or C$_1$-C$_6$ alkoxy wherein R$^{19}$ may be further substituted by Z; or

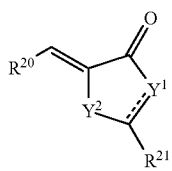

I)

wherein

Y$^1$ is N, NH, CH or CH$_2$;

Y$^2$ is O, S, or NH;

- - - - represents an optional double bond;

R$^{20}$ is substituted or unsubstituted aryl, substituted or unsubstituted heteroaryl, substituted or unsubstituted cycloalkyl, or substituted or unsubstituted heterocycloalkyl, wherein R$^{20}$ may be further substituted by Z;

R$^{21}$ represents =S, =NH, —NHR$^{21a}$, —CHR$^{21a}$, =NR$^{21a}$, or =CCO—R$^{21a}$; and R$^{21a}$ is substituted or unsubstituted aryl, substituted or unsubstituted heteroaryl, substituted or unsubstituted cycloalkyl, or substituted or unsubstituted heterocycloalkyl, wherein R$^{21a}$ may be further substituted by Z; or

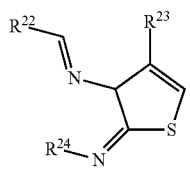

J)

wherein

R$^{22}$ is substituted or unsubstituted aryl, substituted or unsubstituted heteroaryl, substituted or unsubstituted cycloalkyl, or substituted or unsubstituted heterocycloalkyl wherein R$^{22}$ may be further substituted by Z;

R$^{23}$ is C$_1$-C$_8$ alkyl, C$_2$-C$_8$ alkenyl, C$_2$-C$_8$ alkynyl, or C$_1$-C$_6$ alkoxy, substituted or unsubstituted aryl, substituted or unsubstituted heteroaryl, substituted or unsubstituted cycloalkyl, or substituted or unsubstituted heterocycloalkyl wherein R$^{23}$ may be further substituted by Z; and R$^{24}$ is C$_1$-C$_8$ alkyl, C$_2$-C$_8$ alkenyl, C$_2$-C$_8$ alkynyl, or C$_1$-C$_6$ alkoxy, substituted or unsubstituted aryl, substituted or unsubstituted heteroaryl, substituted or unsubstituted cycloalkyl, or substituted or unsubstituted heterocycloalkyl wherein R$^{24}$ may be further substituted by Z; or

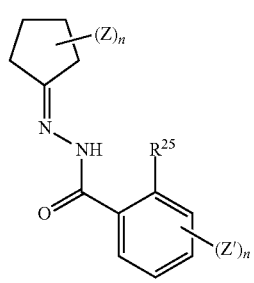

K)

wherein

R$^{25}$ is —CO—R$^{25a}$; —CO—NH—(CH$_2$)$_n$—R$^{25a}$; —CO—CH$_2$—R$^{25a}$, —NH—CO—NH—R$^{25a}$; —NH—SO$_2$—NH—R$^{25a}$; or —NH—CO—R$^{25a}$; —NH—SO$_2$—R$^{25a}$

R$^{25a}$ is substituted or unsubstituted aryl, substituted or unsubstituted heteroaryl, substituted or unsubstituted cycloalkyl, or substituted or unsubstituted heterocycloalkyl wherein R$^{22}$ may be further substituted by Z; or

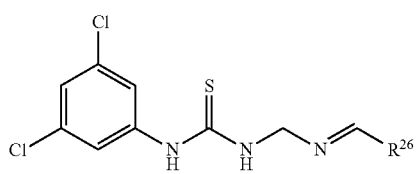

L)

wherein
R²⁶ is substituted or unsubstituted aryl, substituted or unsubstituted heteroaryl, substituted or unsubstituted cycloalkyl, or substituted or unsubstituted heterocycloalkyl wherein R²² may be further substituted by Z;
or
and wherein
in each of formulas A-L:
each occurrence of n is independently an integer from 0-4;
each occurrence of m is independently an integer from 0-3;
each occurrence of p is independently an integer from 0-2;
each occurrence of q is independently an integer from 0-1;
each occurrence of Z, Z' and Z" is independently halogen, hydroxyl, $C_1$-$C_8$ alkyl, $C_2$-$C_8$ alkenyl, $C_2$-$C_8$ alkynyl, or $C_1$-$C_6$ alkoxy, substituted or unsubstituted aryl, substituted or unsubstituted heteroaryl, substituted or unsubstituted cycloalkyl, or substituted or unsubstituted heterocycloalkyl, or M)
a compound having the formula

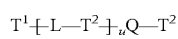

wherein:
T¹ represents a compound of the formula A-L;
each T² independently represents another compound of the formula A-L which may be the same or different from T¹;
each Q represents a direct bond, a $C_1$-$C_8$ alkylene linker, a $C_2$-$C_8$ alkenylene linker, a $C_2$-$C_8$ alkynylene linker, an amide linker, or a sulfonamide linker formed by joining together a Z, Z', or Z" moiety of T¹ with a Z, Z', or Z" moiety of each subsequent T²; and
u represents an integer from 0-5
or a pharmaceutically acceptable salt, solvate, hydrate or stereoisomer thereof.

In some embodiments, the invention encompasses a compound of having the formula M:

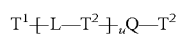

wherein:
T¹ represents a compound of the formula A-L;
each T² independently represents another compound of the formula A-L which may be the same or different from T¹;
each Q represents a direct bond, a $C_1$-$C_8$ alkylene linker, a $C_2$-$C_8$ alkenylene linker, or a $C_2$-$C_8$ alkynylene linker formed by joining together a Z, Z', or Z" moiety of T¹ with a Z, Z', or Z" moiety of each subsequent T²; and
u represents an integer from 0-5
or a pharmaceutically acceptable salt, solvate, hydrate or stereoisomer thereof.

In some embodiments, the invention encompasses a compound having the formula M wherein u is 0 and Q is a direct bond.

In still other embodiments, the invention encompasses a compound having the formula M wherein u is 0 and Q is a $C_1$-$C_8$ alkylene linker.

In yet other embodiments, the invention encompasses a compound having the formula M wherein u is 1 and each Q is independently a direct bond or a $C_1$-$C_8$ alkylene linker.

Representative compounds and subclasses of compounds of the invention are identified in Table 1 (including Subtables Table 1-A through Table 1-P). These compounds may be useful in the methods and compositions described herein.

Another aspect of the invention encompasses a pharmaceutical composition comprising one or more compounds according to Formula A-M or physiologically acceptable salts, solvates, hydrates, stereoisomers, or fusion compounds thereof and a pharmaceutically acceptable diluent or carrier. In some embodiments, the pharmaceutical composition the invention encompasses a composition wherein the compound is present in a therapeutically effective amount.

In still another embodiment, the pharmaceutical composition the invention further encompasses at least one further active compound. In one embodiment, the further active compound is a death receptor stimulant, an HDAC inhibitor, a proteasome inhibitor, a BCL-2 family inhibitor, a kinase inhibitor, a mitotic inhibitor, a nucleoside analog, an anticancer monoclonal antibody, a corticosteroid, a DNA-damaging agent, an antimetabolite, or other cell death-activating stimulant.

Another aspect of the invention encompasses a packaged pharmaceutical composition comprising a container, the pharmaceutical composition of the invention and instructions for using the pharmaceutical composition to treat a disease or condition in a mammal.

Yet another aspect of the invention encompasses a method of modulating MCL-1 in a cell comprising contacting a cell with one or more compounds of the invention. In one embodiment, the activity modulated is apoptotic cell death. In another embodiment, the activity modulated is autophagy. In another embodiment, the activity modulated is necrotic cell death. In another embodiment, the activity modulated is cell metabolism. In another embodiment, the activity modulated is cell division. In another embodiment, the activity modulated is transcription in a cell. In another embodiment, the activity modulated is RNA Processing in a cell. In another embodiment, the activity modulated is cell differentiation. In another embodiment, the activity modulated is transcription. In another embodiment, the activity modulated is RNA processing. In another embodiment, the activity modulated is protein multimerization or dissociation.

Still another aspect of the invention encompasses a method of treating a hyperproliferative disorder in a mammal comprising administering to a mammal in need thereof, a therapeutically effective amount of one or more compounds of the invention. In some embodiments, the hyperproliferative disorder is cancer, including but not limited to, cancer of the breast, respiratory tract, brain, reproductive organs, digestive tract, urinary tract, eye, liver, skin, head and neck, thyroid, parathyroid or a distant metastasis of a solid tumor, a lymphoma, sarcoma, melanoma or leukemia.

Yet another aspect of the invention encompasses a method of treating an angiogenesis disorder in a mammal comprising administering to a mammal in need thereof, a therapeutically effective amount of one or more compounds of the invention.

Still yet another aspect of the invention encompasses a method of treating an inflammatory disorder in a mammal comprising administering to a mammal in need thereof, a therapeutically effective amount of one or more compounds of the invention.

Another aspect of the invention encompasses a method of treating an infectious disease in a mammal comprising administering to a mammal in need thereof, a therapeutically effective amount of one or more compounds of the invention.

Still another aspect of the invention encompasses a method of treating a cell cycle regulation disorder in a mammal comprising administering to a mammal in need thereof, a therapeutically effective amount of one or more compounds of the invention.

Yet another aspect of the invention encompasses a method of treating an autophagy regulation disorder in a mammal comprising administering to a mammal in need thereof, a therapeutically effective amount of one or more compounds of the invention.

Still yet another aspect of the invention encompasses a method of treating an autoimmune disorder in a mammal comprising administering to a mammal in need thereof, a therapeutically effective amount of one or more compounds of the invention.

Another aspect of the invention encompasses a method of enhancing wound repair in a mammal comprising administering to a mammal in need thereof, a therapeutically effective amount of one or more compounds of the invention.

Yet another aspect of the invention encompasses a method of enhancing cellular engraftment in a mammal comprising administering to a mammal in need thereof, a therapeutically effective amount of one or more compounds of the invention.

Another aspect of the invention encompasses a method of sensitizing a cell to treatment by a secondary active ingredient comprising administering to a cell a sensitizing amount of one or more compounds of the invention. In certain embodiments, the secondary active ingredient is a death receptor stimulant, an HDAC inhibitor, a proteasome inhibitor, a BCL-2 family inhibitor, a kinase inhibitor, a mitotic inhibitor, a nucleoside analog, an anti-cancer monoclonal antibody, a corticosteroid, a DNA-damaging agent, an antimetabolite, or other cell death-activating stimulant.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

BRIEF DESCRIPTION OF THE DRAWINGS

FIG. 3B demonstrates that small molecule bioactives identified as MCL-1 selective indeed exhibit preferential displacement of FITC-BID BH3 from MCL-1ΔNΔC compared to other anti-apoptotic proteins. The tabulated $IC_{50}$ values are shown.

FIG. 4B shows tabulated $IC_{50}$ values in μM, demonstrating that small molecules identified as MCL-1 selective exhibit preferential displacement of FITC-BID BH3 from MCL-1ΔNΔC compared to other anti-apoptotic proteins.

FIG. 5C shows a combination treatment analysis using CalcuSyn software revealing combination index values that reflect synergy between treatment with TRAIL and the identified small molecule bioactive hits that target MCL-1. The tabulated combination index values document synergy of MCL-1-targeting molecules from bioactive library in reducing OPM2 cell viability when combined with TRAIL.

FIG. 5D shows a combination treatment analysis using CalcuSyn software revealing combination index values that reflect synergy between treatment with TRAIL and the identified small molecule hits that target MCL-1. The tabulated combination index values document synergy of MCL-1-targeting molecules from small molecule libraries in reducing OPM2 cell viability when combined with TRAIL. (CI<0.9, synergy; 0.9<CI<1.1, additive effect; CI>1.1, antagonism).

DETAILED DESCRIPTION OF THE INVENTION

Definitions

Figures 1A, 1B:
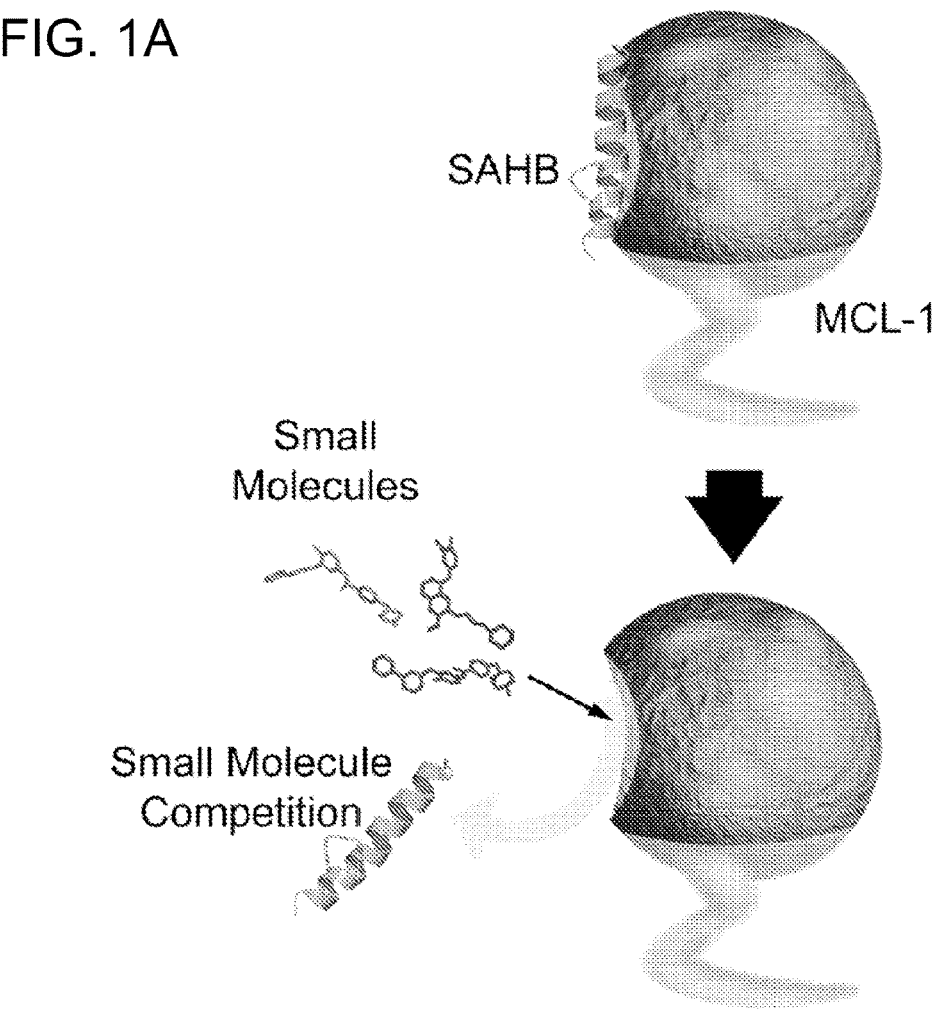
FIG. 1A shows the application of a selective stapled peptide in a competitive binding screen to identify selective small molecules against a protein target.
FIG. 1B shows workflow for identifying small molecules that selectively target MCL-1.

In order that the invention may be more readily understood, certain terms are first defined and collected here for convenience. Other definitions appear in context throughout the application.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "halogen" refers to radicals of fluorine, chlorine, bromine and iodine.

The term "alkyl" refers to a straight or branched hydrocarbon chain radical, containing solely carbon and hydrogen atoms, having in the range from one up to eight carbon atoms, and which is attached to the rest of the molecule by a single bond, such as illustratively, methyl, ethyl, n-propyl 1-methylethyl (iso-propyl), n-butyl, n-pentyl, and 1,1-dimethylethyl (tert-butyl).

The term "cycloalkyl" denotes a non-aromatic mono or multicyclic ring system having in the range of 3 up to 14 carbon atoms such as cyclopropyl, cyclobutyl, cyclopentyl, and cyclohexyl. Examples of multicyclic cycloalkyl groups include decahydronapththyl. Examples of bridged cycloalkyl groups or sprirobicycloalkyl groups include adamantyl norbornyl, and sprio[4.4]nonyl groups.

The term "alkoxy" denotes an alkyl group as defined herein attached via an oxygen linkage to the rest of the molecule. Representative examples of those groups are methoxy, ethoxy, iso-propoxy, n-butoxy, and tert-butoxy.

The term "cycloalkoxy" denotes a cycloalkyl group as defined herein attached via an oxygen linkage to the rest of the molecule. Representative examples of those groups are cyclopropoxy, cyclobutoxy, cyclopentoxy, cyclohexoxy, and cycloheptoxy.

The term "aryl" refers to aromatic radicals having in the range of 6 up to 14 carbon atoms such as phenyl, naphthyl, indanyl, and biphenyl.

The term "heteroaryl" refers to a stable 5- to 13-membered aromatic heterocycle having in the range of from 1 up to 4 heteroatoms from the group consisting of nitrogen, phosphorus, oxygen and sulfur, which ring or ring system can be linked via a carbon atom or a nitrogen atom, if such an atom is present. For purposes of this invention, the heteroaryl ring radical may be a monocyclic, bicyclic or tricyclic ring system. Examples of such heteroaryl radicals are: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolicenyl, indolyl, benzo[b]thienyl, benzo[b]furyl, benzothiazolyl, benzothiadiazolyl, indazolyl, quinolyl, isoquinolyl, isoquinolyl, naphthyridinyl, quinazolinyl, oxadiazolyl, benzoxazolyl, tetrazoyl, triazolyl, thiadiazolyl, and benzimidazolyl.

The term "heterocycloalkyl" refers to a stable 3 to 13 membered saturated or partially unsaturated heterocycle having in the range from 1 up to 4 heteroatoms from the group consisting of nitrogen, phosphorus, oxygen and sulfur, which ring or ring system can be linked via a carbon atom or a nitrogen atom, if such an atom is present. For purposes of this invention, the heterocyclic ring radical may be a monocyclic, bicyclic or tricyclic ring system, which may include fused, bridged or spiro ring systems. Examples of such heterocyclyl radicals are: tetrahydropyranyl, aziridyl, azepanyl, tetrahydrofuryl, pyrrolidinyl, pyrrolinyl, piperidinyl, 1,2 dihydropyridinyl, 1,4 dihydropyridinyl, piperazinyl, morpholinyl, thiomorpholinyl, azepinyl, oxazolinyl, thiazolinyl and 1,4 diazepinyl.

The term "alkylamino" refers to an alkyl group as defined herein attached via amino linkage to the rest of the molecule. The term alkylamino further includes dialkyl amino moieties in which two alkyl groups as define herein are attached via amino linkage to the rest of the molecule. Representative examples of those groups are methylamino and dimethylamino.

Where the plural form of the word compounds, salts, polymorphs, hydrates, solvates and the like, is used herein, this is taken to mean also a single compound, salt, polymorph, isomer, hydrate, solvate or the like.

The compounds of this invention may contain one or more asymmetric centers, depending upon the location and nature of the various substituents desired. Asymmetric carbon atoms may be present in the (R) or (S) configuration, resulting in racemic mixtures in the case of a single asymmetric center, and diastereomeric mixtures in the case of multiple asymmetric centers. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivitization, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of this invention can likewise be obtained by chiral syntheses utilizing optically active starting materials.

The present invention also relates to useful forms of the compounds as disclosed herein, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid.

Pharmaceutically acceptable salts also include those in which a compound of the invention functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of a compound of the invention the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of a compound of the invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

The term "subject" refers to animals such as mammals, including, but not limited to, primates (e.g., humans), cows, sheep, goats, horses, dogs, cats, rabbits, rats, mice and the like. In certain embodiments, the subject is a human.

It is also to be understood that the terminology used herein is for purposes of describing particular embodiments only, and is not intended to be limiting. As used in the specification and the appended claims, the singular forms "a", "an", and "the" include plural referents unless the context clearly indicates otherwise. Thus, for example, reference to "a peptide" includes multiple peptides, reference to "a spacer" includes two or more spacers.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Compounds

As set forth above, the invention provides compounds which selectively bind to the survival protein MCL-1 with high affinity and selectivity.

Figure 4A:
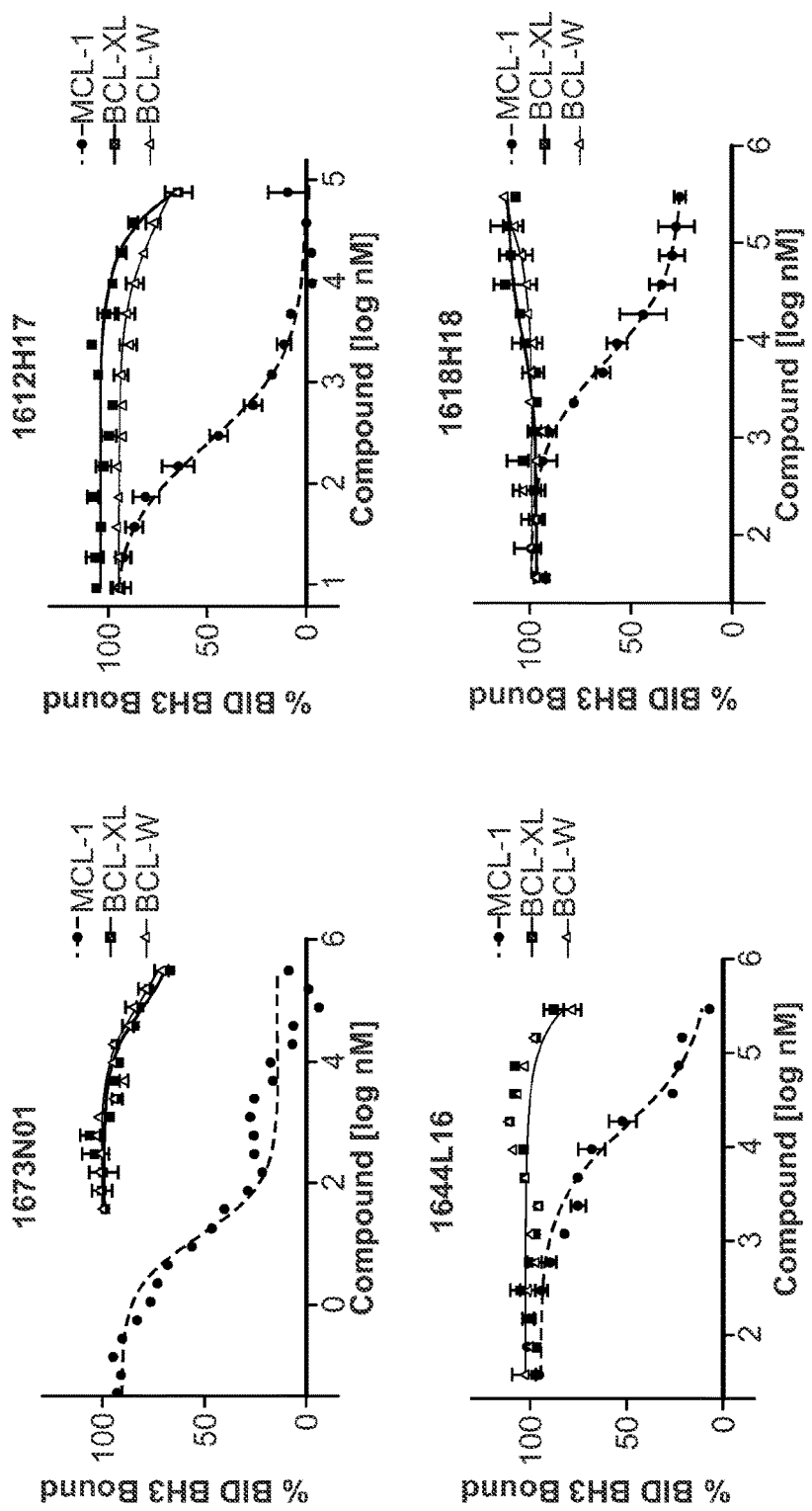
FIG. 4A shows the degree of MCL-1 selectivity as determined by competitive fluorescence polarization binding assays (FPA) in a secondary screen of hits from small molecule libraries against FITC-BID BH3/anti-apoptotic protein interactions. Competitive FPA binding curves as shown.
Figure 4C:
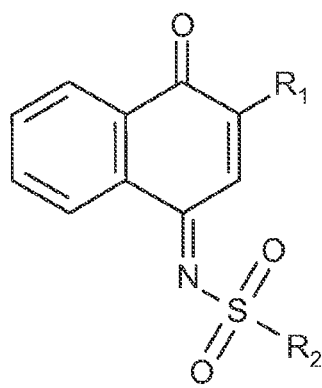
FIG. 4C shows structure-activity relationship (SAR) analysis for select derivatives of Class A molecular inhibitors of MCL-1, using the FITC-BID BH3/MCL-1ΔNΔC competitive fluorescence polarization binding assay.
Figure 4C:
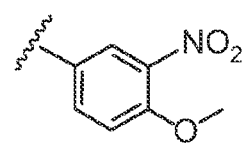
Figure 4C:
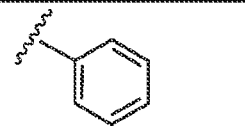
Figure 4C:
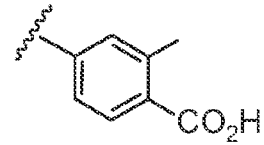
Figure 4C:
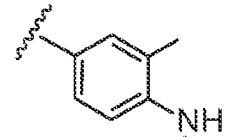
Figure 4C:
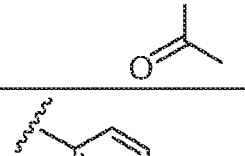
Figure 4C:
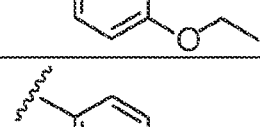
Figure 4C:
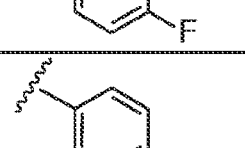
Figure 4C:
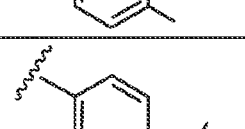
Figure 4D:
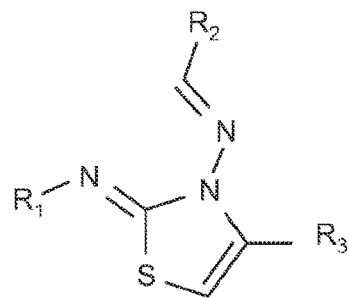
FIG. 4D shows structure-activity relationship (SAR) analysis for select derivatives of Class J molecular inhibitors of MCL-1, using the FITC-BID BH3/MCL-1ΔNΔC competitive fluorescence polarization binding assay.

Table 1 (including Subtables Table 1-A through Table 1-P) lists of representative compounds and subclasses identified as selective or preferential MCL-1 binders based upon a small molecule competitive binding assay using FITC-MCL-1 SAHB/MCL-1$\Delta$N$\Delta$C and FITC-BAD BH3/BCL-$X_L\Delta$C interaction pairs. FIGS. 4C and 4D tabulates select derivatives of Class A and Class J compounds that exhibit differential MCL-1 targeting activity based on chemical variation of discrete R groups.

Certain compounds of Table 1 describe certain known bioactive compounds. These compounds are particularly useful in targeting MCL-1 and may be useful in the treatment of diseases as described herein. Thus, in certain aspects, the compounds of Formula A-L may exclude certain compounds of Table 1.

The compounds of the invention may contain one or more asymmetric centers and thus occur as racemates and racemic mixtures, single enantiomers, individual diastereomers and diastereomeric mixtures. All such isomeric forms of these compounds are expressly included in the invention. The compounds of this invention may also be represented in multiple tautomeric forms, in such instances, the invention expressly includes all tautomeric forms of the compounds described herein. All such isomeric forms of such compounds are expressly included in the invention. All crystal forms of the compounds described herein are expressly included in the invention.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

Methods of obtaining a compound of the invention include purchasing, synthesizing or otherwise acquiring the compound. Synthesizing a compound of the invention is within the means of chemists of ordinary skill in the art. Methods for optimizing reaction conditions, if necessary minimizing competing by-products, are known in the art. The methods may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Methods of Treatment

In one aspect, the invention encompasses a method of modulating MCL-1 in a cell comprising contacting a cell with one or more compounds of the invention. Such modulation is useful in the modulation of programmed cell death or apoptosis, autophagic cell death; necrotic cell death; cell metabolism; cell division; cell differentiation; cell migration; cell engraftment; tissue repair; RNA transcription and processing; or protein multimerization or dissociation.

As used herein, the term "modulation" refers to a change in activity as a direct or indirect response to the presence of at least one compound of the invention described herein, relative to the activity in the absence of the compound. The change may be an increase in activity or a decrease in activity, and may be due to the direct interaction of the compound with MCL-1, or due to the interaction of the compound with one or more other factors that in turn interact with MCL-1 or affect MCL-1 activity. In certain embodiments, the modulation may be the result of a covalent bond between the compound with MCL-1. In certain embodiments, the modulation may be the result of a non-covalent bond between the compound with MCL-1. In certain embodiments, the modulation may be the result of a covalent bond between the compound with the established BH3 binding site of MCL-1 or with a residue of MCL-1 not associated with the established BH3 binding site of MCL-1. In certain embodiments, the modulation may be the result of a non-covalent bond between the compound with the established BH3 binding site of MCL-1 or with a residue of MCL-1 not associated with the established BH3 binding site of MCL-1. In still other embodiments, the modulation may be the result of a covalent bond between the compound with the C286 reside of MCL-1. In certain embodiments, the modulation may be the result of a non-covalent bond between the compound in the region of the C286 residue of MCL-1.

In one aspect, the invention encompasses a method of treating a hyperproliferative disorder in a mammal comprising administering to a mammal in need thereof, a therapeutically effective amount of one or more compounds of the invention.

As used herein the term "hyperproliferative disorder" refers to a disorder associated with an irregular or an abnormally high rate of cell division (which results in a rapid proliferation of the cells) or a blockade in the natural cell death pathway resulting in the accumulation of cells, or a combination thereof. Hyperproliferative disorders include but are not limited, e.g., psoriasis, keloids, and other hyperplasias affecting the skin, benign prostate hyperplasia (BPH), solid and liquid tumors, such as cancers of the breast, respiratory tract, brain, reproductive organs, digestive tract, urinary tract, eye, liver, skin, head and neck, thyroid, parathyroid and their distant metastases, lymphomas, sarcomas, and leukemias.

Still another aspect of the invention encompasses a method of treating a cell cycle regulation disorder in a mammal comprising administering to a mammal in need thereof, a therapeutically effective amount of one or more compounds of the invention.

As used herein, the term "cell cycle regulation disorder" relates to a disorder of the cell cycle regulation mechanisms, observed in many malignant tumors, are directly related to uncontrolled proliferation of cancer cells. Cell cycle regulation disorders can be the result of the degradation of the regulation of one or more stages of cell growth, $G_1$, S, $G_2$, and M phases of the growth cycle and may include the degradation of one or more cell cycle regulators including, but not limited to, p27Kip1, cdk2, cdk4, cdk6, chk1, cdc25, cyclin B, cyclin H, cyclin D, and cyclin E.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

In one aspect, the invention encompasses a method of treating angiogenesis in a mammal comprising administering to a mammal in need thereof, a therapeutically effective amount of one or more compounds of the invention.

As used herein the term "angiogenesis" refers to a disorder associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), age-related macular degeneration (AMD; see, Lopez et al. Invest. *Opththalmol. Vis. Sci.* 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Another aspect of the invention encompasses a method of treating an infectious disease by blocking pathogen or infected cell survival in a mammal comprising administering to a mammal in need thereof, a therapeutically effective amount of one or more compounds of the invention.

Examples of infectious diseases include, but are not limited to, AIDS, Alveolar Hydatid Disease (AHD, Echinococcosis), Amebiasis (Entamoeba histolytica Infection), Angiostrongylus Infection, Anisakiasis, Anthrax, Babesiosis (Babesia Infection), Balantidium Infection (Balantidiasis), Baylisascaris Infection (Raccoon Roundworm), Bilharzia (Schistosomiasis), Blastocystis hominis Infection (Blastomycosis), Boreliosis, Botulism, Brainerd Diarrhea, Brucelosis, BSE (Bovine Spongiform Encephalopathy), Candidiasis, Capillariasis (Capillaria Infection), CFS (Chronic Fatigue Syndrome), Chagas Disease (American Trypanosomiasis), Chickenpox (Varicella-Zoster virus), Chlamydia pneumoniae Infection, Cholera, Chronic Fatigue Syndrome, CJD (Creutzfeldt-Jakob Disease), Clonorchiasis (Clonorchis Infection), CLM (Cutaneous Larva Migrans, Hookworm Infection), Coccidioidomycosis, Conjunctivitis, Coxsackievirus A16 (Hand, Foot and Mouth Disease), Cryptococcosis, Cryptosporidium Infection (Cryptosporidiosis), Culex mosquito (Vector of West Nile Virus), Cutaneous Larva Migrans (CLM), Cyclosporiasis (Cyclospora Infection), Cysticercosis (Neurocysticercosis), Cytomegalovirus Infection, Dengue/Dengue Fever, Dipylidium Infection (Dog and Cat Flea Tapeworm), Ebola Virus Hemorrhagic Fever, Echinococcosis (Alveolar Hydatid Disease), Encephalitis, Entamoeba coli Infection, Entamoeba dispar Infection, Entamoeba hartmanni Infection, Entamoeba histolytica Infection (Amebiasis), Entamoeba polecki Infection, Enterobiasis (Pinworm Infection), Enterovirus Infection (Non-Polio), Epstein-Barr Virus Infection, Escherichia coli Infection, Foodborne Infection, Foot and mouth Disease, Fungal Dermatitis, Gastroenteritis, Group A streptococcal Disease, Group B streptococcal Disease, Hansen's Disease (Leprosy), Hantavirus Pulmonary Syndrome, Head Lice Infestation (Pediculosis), Heliobacter pylori Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis (Isospora Infection), Lassa Fever, Leishmaniasis, Kala-azar (Kala-azar, Leishmania Infection), Lice (Body lice, Head lice, Pubic lice), Lyme Disease, Malaria, Marburg Hemorrhagic Fever, Measles, Meningitis, Mosquito-borne Diseases, Mycobacterium avium Complex (MAC) Infection, Naegleria Infection, Nosocomial Infections, Nonpathogenic Intestinal Amebae Infection, Onchocerciasis (River Blindness), Opisthorciasis (Opisthorcis Infection), Parvovirus Infection, Plague, PCP (Pneumocystis carinii Pneumonia), Polio, Q Fever, Rabies, Respiratory Syncytial Virus (RSV) Infection, Rheumatic Fever, Rift Valley Fever, River Blindness (Onchocerciasis), Rotavirus Infection, Roundworms Infection, Salmonellosis, Salmonella Enteritidis, Scabies, Shigellosis, Shingles, Sleeping Sickness, Smallpox, Streptococcal Infection, Tapeworm Infection (Taenia Infection), Tetanus, Toxic Shock Syndrome, Tuberculosis, Ulcers (Peptic Ulcer Disease), Valley Fever, Vibrio parahaemolyticus Infection, Vibrio vulnificus Infection, Viral Hemorrhagic Fever, Warts, Waterborne infectious Diseases, West Nile Virus Infection (West Nile Encephalitis), Whooping Cough, Yellow Fever, tuberculosis, leprosy, mycobacteria-induced meningitis, Chagas disease, effects of Shiga-like toxin resulting from Staphylococcus infection, meningococcal infection, and infections from Borrelia burgdorferi or Treponema pallidum.

Yet another aspect of the invention encompasses a method of treating an autophagy regulation disorder in a mammal comprising administering to a mammal in need thereof, a therapeutically effective amount of one or more compounds of the invention.

As used herein, the term "autophagy regulation disorder" relates to a dissorder of the autophagy system of a cell i.e. the self-digestion by a cell through the action of enzymes originating within the same cell including, but not limited to, chaperone-mediated autophagy, macroautophagy, microautophagy. Disorders of autophagy regulation include but are not limited to, Danon disease X-linked myopathy with excessive autophagy, Infantile autophagic vacuolar myopathy, Childhood autophagic vacuolar myopathy, Adult-onset autophagic vacuolar myopathy with multiorgan involvement, LGMD 1A, Toxic myopathy, Inflammatory myopathies, Hypokalemic myopathy, Acid maltase deficiency, Inflammatory bowel disease associations, Autophagy 16-like 1 (ATG16L1), LRG47, and autophagy-mediated survival of cancer cells or cancer stem cells to escape chemotherapy or radiation treatments.

Still yet another aspect of the invention provides a method of treating an autoimmune disorder in a mammal comprising administering to a mammal in need thereof, a therapeutically effective amount of one or more compounds of the invention.

Examples of autoimmune disorders include, but are not limited to, allergic bronchopulmonary aspergillosis; autoimmune hemolytic anemia; acanthosis nigricans; allergic contact dermatitis; Addison's disease; atopic dermatitis; alopecia greata; alopecia universalis; amyloidosis; anaphylactoid purpura; anaphylactoid reaction; aplastic anemia; angioedema, hereditary; angioedema, idiopathic; ankylosing spondylitis; arteritis, cranial; arteritis, giant cell; arteritis, Takayasu's; arteritis, temporal; asthma; a-telangiectasia; autoimmune oophoritis; autoimmune orchitis; autoimmune polyendocrine failure; Behcet's disease; Berger's disease; Buerger's disease; bullous pemphigus; candidiasis, chronic mucocutaneous; Caplan's syndrome; post-myocardial infarction syndrome; post-pericardiotomy syndrome; carditis; celiac sprue; Chagas's disease; Chediak-Higashi syndrome; Churg-Strauss disease; Cogan's syndrome; cold agglutinin disease; CREST syndrome; Crohn's disease; cryoglobulinemia; cryptogenic fibrosing alveolitis; dermatitis herpetifomis; dermatomyositis; diabetes mellitus; Diamond-Blackfan syndrome; DiGeorge syndrome; discoid lupus erythematosus; eosinophilic fasciitis; episcleritis; drythema elevatum diutinum; erythema marginatum; erythema multiforme; erythema nodosum; familial Mediterranean fever; Felty's syndrome; fibrosis pulmonary; glomerulonephritis, anaphylactoid; glomerulonephritis, autoimmune; glomerulonephritis, post-streptococcal; glomerulonephritis, post-transplantation; glomerulopathy, membranous; Goodpasture's syndrome; graft-vs.-host disease; granulocytopenia, immune-mediated; granuloma annulare; granulomatosis, allergic; granulomatous myositis; Grave's disease; Hashimoto's thyroiditis; hemolytic disease of the newborn; hemochromatosis, idiopathic; Henoch-Schoenlein purpura; hepatitis, chronic active and chronic progressive; histiocytosis X; hypereosinophilic syndrome; idiopathic thrombocytopenic purpura; Job's syndrome; juvenile dermatomyositis; juvenile rheumatoid arthritis juvenile chronic arthritis); Kawasaki's disease; keratitis; keratoconjunctivitis sicca; Landry-Guillain-Barre-Strohl syndrome; leprosy, lepromatous; Loeffler's syndrome; Lyell's syndrome; Lyme disease; lymphomatoid granulomatosis; mastocytosis, systemic; mixed connective tissue disease; mononeuritis multiplex; Muckle-Wells syndrome; mucocutaneous lymph node syndrome; mucocutaneous lymph node syndrome; multicentric reticulohistiocytosis; multiple sclerosis; myasthenia gravis; mycosis fungoides; necrotizing vasculitis, systemic; nephrotic syndrome; overlap syndrome; panniculitis; paroxysmal cold hemoglobinuria; paroxysmal nocturnal hemoglobinuria; pemphigoid; pemphigus; pemphigus erythematosus; pemphigus foliaceus; pemphigus vulgaris; pigeon breeder's disease; pneumonitis, hypersensitivity; polyarteritis nodosa; polymyalgia rheumatica; polymyositis; polyneuritis, idiopathic; Portuguese familial polyneuropathies; pre-eclampsia/eclampsia; primary biliary cirrhosis; progressive systemic sclerosis (scleroderma); psoriasis; psoriatic arthritis; pulmonary alveolar proteinosis; pulmonary fibrosis, Raynaud's phenomenon/syndrome; Reidel's thyroiditis; Reiter's syndrome, relapsing polychrondritis; rheumatic fever; rheumatoid arthritis; sarcoidosis; scleritis; sclerosing cholangitis; serum sickness; Sezary syndrome; Sjogren's syndrome; Stevens-Johnson syndrome; Still's disease; subacute sclerosing panencephalitis; sympathetic ophthalmia; systemic lupus erythematosus; transplant rejection; ulcerative colitis; undifferentiated connective tissue disease; urticaria, chronic; urticaria, cold; uveitis; vitiligo; Weber-Christian disease; Wegener's granulomatosis; and Wiskott-Aldrich syndrome.

In another aspect, the invention provides a method of enhancing cellular engraftment in a subject comprising administering to a subject in need thereof of a therapeutically effective amount of one or more compounds of the invention.

As used herein the phrase "enhancing cellular engraftment" refers to an improvement in efficiency, quality or rapidity of cell transplantation which may result from improved homing to the target tissue, improved adhesion, reduced rejection and the like. Methods for assessing cell engraftinent potential include, for example, cell migration and other in vitro techniques, and histological, immunological and/or radiological assessment of tissues and organs from actual in-vivo transplantation. In certain aspects, the term "enhancing cellular engraftment" also includes, but is not limited to, the treatment of a disorder in which the subject is treated with cells, such as in the context of bone marrow transplantation, stem cell replacement, and skin engraftment.

In another aspect, the invention provides a method of enhancing wound repair in a subject comprising administering to a subject in need thereof of a therapeutically effective amount of one or more compounds of the invention.

As used herein the term, "enhancing wound repair" includes, but is not limited to, the formation of granulation tissue; of wound contraction; and/or the induction of epithelialization (i.e., the generation of new cells in the epithelium). Wound repair is conveniently measured by decreasing wound area. In certain aspects, the term "enhancing wound repair" also includes, but is not limited to, the treatment a disorder in which the subject is being treated for tissue damage, either internal or external, such that the goal is to restore organ or tissue integrity.

In another aspect, the invention provides a method of treating an inflammatory condition in a subject comprising administering to a subject in need thereof an effective amount of a composition comprising a compound of the invention or a pharmaceutically acceptable salt thereof.

As used herein, the term "inflammatory condition" refers to a condition or disorder associated with one or more aberrant physiological processes or other physiological responses (such as responses to an injurious or noxious stimulus) which result in a pathophysiological state of inflammation. An inflammatory condition may be either an acute or chronic inflammatory condition, which can result from infections or non-infectious causes. Various infectious causes include meningitis, encephalitis, uveitis, colitis, tuberculosis, dermatitis, and adult respiratory distress syndrome. Non-infectious causes include trauma (burns, cuts, contusions, crush injuries), autoimmune diseases, and organ rejection episodes. Thus, in specific aspects, an inflammatory condition results from a condition selected from the group that includes: atherosclerosis (arteriosclerosis); autoimmune conditions, such as multiple sclerosis, systemic lupus erythematosus, polymyalgia rheumatica (PMR), gouty arthritis, degenerative arthritis, tendonitis, bursitis, psoriasis, fibrosis, arthrosteitis, rheumatoid arthritis and other forms of inflammatory arthritis, Sjogren's Syndrome, progressive systemic sclerosis (scleroderma), ankylosing spondylitis, polymyositis, dermatomyositis, pemphigus, pemphigoid, Type I diabetes mellitus, myasthenia gravis, Hashimoto's thyroditis, Graves' disease, Goodpasture's disease, mixed connective tissue disease, sclerosing cholangitis, inflammatory bowel disease including Crohn's Disease (regional enteritis) and ulcerative colitis, pernicious anemia, inflammatory dermatoses; usual interstitial pneumonitis (UIP), asbestosis, silicosis, bronchiectasis, berylliosis, talcosis, all forms of pneumoconiosis, sarcoidosis (in the lung and in any other organ), desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa); sepsis; inflammatory dermatoses not presumed to be autoimmune; chronic active hepatitis; delayed-type hypersensitivity reactions (e.g., poison ivy dermatitis); pneumonia or other respiratory tract inflammation due to any cause; Adult Respiratory Distress Syndrome (ARDS) from any etiology; encephalitis with inflammatory edema; immediate hypersensitivity reactions including, but not limited to, asthma, hayfever, cutaneous allergies, acute anaphylaxis; diseases involving acute deposition of immune complexes, including, but not limited to, rheumatic fever, acute and/or chronic glomerulonephritis due to any etiology, including specifically post-infectious (e.g., post-Streptococcal) glomerulonephritis, acute exacerbations of Systemic Lupus Erythematosus; pyelonephritis; cellulitis; cystitis; acute and/or chronic cholecystitis; and conditions producing transient ischemia anywhere along the gastrointestinal tract, bladder, heart, or other organ, especially those prone to rupture; sequelae of organ transplantation or tissue allograft, including allograft rejection in the acute time period following allogeneic organ or tissue transplantation and chronic host-versus-graft rejection. The term "inflammatory condition" also includes appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, tonsillitis, uveitis, vaginitis, vasculitis, vulvitis, and vulvovaginitis, angitis, chronic bronchitis, osteomylitis, optic neuritis, temporal arteritis, transverse myelitis, necrotizing fascilitis, hepatitis, and necrotizing enterocolitis.

In a specific aspect, the invention encompasses a method of targeting MCL-1 in a cell comprising contacting a cell with one or more compounds selected from gossypol, celastrol, manoalide, u73122, bithionol and hexachlorophene. Such targeting may useful in the modulation of programmed cell death or apoptosis, autophagic cell death; necrotic cell death; cell metabolism; cell division; cell differentiation; RNA transcription and processing; or protein multimerization or dissociation.

As used herein, the term "targeting" refers to the direct interaction of the compound with MCL-1, or to the interaction of the compound with one or more other factors that in turn interact with MCL-1 or affect MCL-1 activity.
Administration In certain embodiments, a compound of the invention or a pharmaceutically acceptable salt, solvate or hydrate thereof is administered to the subject in a pharmaceutically-acceptable formulation. In certain embodiments, a compound of the invention or a pharmaceutically acceptable salt, solvate or hydrate thereof or an a compound of the invention pharmaceutical composition is suitable for topical, intravenous, parental, or oral administration. The methods of the invention further include administering to a subject a therapeutically effective amount of a compound of the invention or a pharmaceutically acceptable salt, solvate or hydrate thereof.

The phrase "pharmaceutically acceptable" refers to a compound of the invention, compositions containing a compound of the invention, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, involved in carrying or transporting the subject chemical from one organ, or portion of the body, to another organ, or portion of the body. Each carrier must be "acceptable" in the sense of being compatible with the other ingredients of the formulation and not injurious to the patient.

Methods of preparing these compositions include the step of bringing into association a compound of the invention or a pharmaceutically acceptable salt, solvate or hydrate thereof with the carrier and, optionally, one or more accessory ingredients. These compositions may also contain adjuvants such as preservatives, wetting agents, emulsifying agents and dispersing agents.

Regardless of the route of administration selected, a compound of the invention, which may be used in a suitable salt, solvate, or hydrate form, and/or the pharmaceutical compositions of a compound of the invention, are formulated into pharmaceutically acceptable dosage forms by conventional methods known to those of skill in the art.

Formulations are provided to a subject in an effective amount. The term "effective amount" includes an amount effective, at dosages and for periods of time necessary, to achieve the desired result. An effective amount of a compound of the invention may vary according to factors such as the disease state, age, and weight of the subject, and the ability of the compound to elicit a desired response in the subject. Dosage regimens may be adjusted to provide the optimum therapeutic response.

The effective amount is generally determined by the physician on a case-by-case basis and is within the skill of one in the art. As a rule, the dosage for in vivo therapeutics or diagnostics will vary. Several factors are typically taken into account when determining an appropriate dosage. These factors include age, sex and weight of the patient, the condition being treated, and the severity of the condition. In addition, an effective amount is preferably selected to minimize adverse side effects. For example, an effective amount of a compound of the invention is preferably selected to treat or prevent a disorder as disclosed herein, while minimizing side effects such as hypotension.

Suitable dosages and formulations of a compound of the invention or a pharmaceutically acceptable salt, solvate or hydrate thereof can be empirically determined by the administering physician. Standard texts, such as Remington: The Science and Practice of Pharmacy, 17th edition, Mack Publishing Company, and the Physician's Desk Reference, each of which are incorporated herein by reference, can be consulted to prepare suitable compositions and doses for administration. A determination of the appropriate dosage is within the skill of one in the art given the parameters for use described herein.

Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages is within the skill of one in the art given the parameters herein.

In terms of treatment, an effective amount is an amount that is sufficient to palliate, ameliorate, stabilize, reverse or slow the progression of an inflammatory condition or other disorder as disclosed herein, or the symptoms thereof. A therapeutically effective amount can be provided in one or a series of administrations. In terms of an adjuvant, an effective amount is one sufficient to enhance the anti-inflammatory or immune response to the anti-inflammatory or immunogen. The effective amount is generally determined by the physician on a case-by-case basis and is within the skill of one in the art.

As a rule, the dosage for in vivo therapeutics or diagnostics will vary. Several factors are typically taken into account when determining an appropriate dosage. These factors include age, sex and weight of the patient, the condition being treated, the severity of the condition and the method of administration.

The dosage of a compound of the invention or a pharmaceutically acceptable salt, solvate or hydrate thereof can vary from about 0.01 mg to about 1,000 mg per day; about 0.1 mg to about 250 mg per day; about 0.5 mg to about 100 mg per day; or about 1 to about 5 mg per day. Ascertaining dosage ranges is well within the skill of one in the art. The dosage of a compound of the invention or a pharmaceutically acceptable salt, solvate or hydrate thereof can range from about 0.001 to 25 mg/kg of body weight. Such dosages may vary, for example, depending on whether multiple administrations are given, tissue type and route of administration, the condition of the individual, the desired objective and other factors known to those of skill in the art. Administrations can be conducted infrequently, or on a regular weekly basis until a desired, measurable parameter is detected, such as diminution of disease symptoms. Administration can then be diminished, such as to a biweekly or monthly basis, as appropriate.

A therapeutically effective amount can be administered in one or more doses. The term "administration" or "administering" includes routes of introducing the compound(s) to a subject to perform their intended function. Examples of routes of administration which can be used include injection (subcutaneous, intravenous, parenterally, intraperitoneally, intrathecal), oral, inhalation, rectal and transdermal.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically", "peripheral administration" and "administered peripherally" as used herein mean the administration of a compound(s), drug or other material, such that it enters the patient's system and, thus, is subject to metabolism and other like processes, for example, subcutaneous administration.

Such dosages may vary, for example, depending on whether multiple administrations are given, tissue type and route of administration, the condition of the individual, the desired objective and other factors known to those of skill in the art.

Available routes of administration include subcutaneous, intramuscular, intraperitoneal, intradermal, oral, intranasal, intrapulmonary (i.e., by aerosol), intravenously, intramuscularly, subcutaneously, intracavity, intrathecally or transdermally, alone or in combination with other pharmaceutical agents.

A cell can be contacted with a composition including a compound of the invention, in certain embodiments in vivo or, in certain embodiments, in vitro. Contacting a cell in vivo can include administration of the composition to a subject, or to a tissue, such that a cell is contacted with a compound of the invention. Contacting a cell in vitro can include, e.g., contacting the cell with a compound of the invention, or a composition consisting essentially of a compound of the invention, directly or by addition of irinadalone or the composition to a growth medium for the cell.

Additional/Secondary Therapeutic Agents

The compounds and compositions of the invention can be administered with one or more additional additional therapeutic agents either separately or in the same formulation as a compound of the invention.

In certain embodiments the compounds and compositions of the invention are useful in sensitizing a cell or a subject to one or more secondary therapeutic agents. In such embodiments, the invention provides a method for sensitizing a cell to a secondary therapeutic agent comprising administering to said cell a sensitizing amount of one or more compound of the invention. A sensitizing amount may be any amount capable of generating a greater response by the cell to the secondary therapeutic agent as compared to the response by the cell without a compound or composition of the invention. In certain embodiments a sensitizing amount is a therapeutically effective amount. In other embodiments, a sensitizing amount is less than a therapeutically effective amount.

The compounds and compositions of the invention can be administered with one or more additional therapeutic agents either separately or in the same formulation as a compound of the invention.

Additional Therapeutic agents include, but are not limited to antacids, antibiotics, antiemetic agents, antidepressants, and antifungal agents, anti-inflammatory agents, antiviral agents, anticancer agents, immunomodulatory agents, beta-interferons, hormones or cytokines.

Additional Therapeutic agents further include, but are not limited to death receptor stimulants (eg. TRAIL), HDAC inhitor (eg. SAHA), proteasome inhibitor (eg. Bortezomib), BCL-2 family inhibitor (eg. ABT-737, ABT-263, obatoclax), kinase inhibitor (e.g. Gleevac, Raf inhibitor), mitotic inhibitors (e.g. Taxol), nucleoside analogs (e.g. Gemcitabine), and anti-cancer monoclonal antibodies (e.g. cetuximab), corticosteroids (e.g. dexamethasone), DNA-damaging agents (e.g. cisplatin), antimetabolites (e.g. methotrexate).

The compounds of the invention can be formulated in combination with antacids. For example, they can be formulated with aluminum carbonate, aluminum hydroxide, bismuth subsalicylate, calcium carbonate, calcium hydroxide, calcium phosphate, dihydroxyaluminum sodium carbonate, magnesium hydroxide, magnesium oxide, magnesium trisilicate, sodium bicarbonate, simethicone, glycine, or combinations thereof.

The compounds of the invention can be formulated in combination with antibiotics. For example, they can be formulated with a macrolide (e.g., tobramycin), a cephalosporin (e.g., cephalexin, cephradine, cefuroxime, cefprozil, cefaclor, cefixime or cefadroxil), a clarithromycin (e.g., clarithromycin), an erythromycin (e.g., erythromycin), a penicillin (e.g., penicillin V) or a quinolone (e.g., ofloxacin, ciprofloxacin or norfloxacin), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefrnetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The compounds of the invention can be formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinols, thiethylperazine, thioproperazine, tropisetron, and mixtures thereof.

The compounds of the invention can be formulated or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, fernoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The compounds of the invention can be formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

The compounds of the invention can be formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diprionate, amcinonide, beclomethasone dipropionate, betametasone, betamethasone benzoate, betamethasone diprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The compounds of the invention can be formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, alpha-interferons; adefovir, clevadine, entecavir, pleconaril.

The compounds of the invention can be formulated in combination with an immunomodulatory agent. Immunomodulatory agents include, but are not limited to, methothrexate, leflunornide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., MEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114 (IDEC)) and CTLA4-immunoglobulin. Examples of cytokine receptor modulators include, but are not limited to, soluble cytokine receptors (e.g., the extracellular domain of a TNF-alpha. receptor or a fragment thereof, the extracellular domain of an IL-1.beta. receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-alpha., interferon (IFN)-alpha., IFN-beta., IFN-gamma, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-alpha. antibodies, anti-IL-1beta antibodies, anti-IL-6 antibodies, anti-IL-8 antibodies (e.g., ABX-IL-8 (Abgenix)), and anti-IL-12 antibodies).

The compounds of the invention can be formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-alpha, and IFN-gamma).

The compounds of the invention can be formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The compounds of the invention can be formulated in combination with beta-interferons which include, but are not limited to, interferon beta-1a and interferon beta-1b.

The compounds of the invention can be formulated in combination with an absorption enhancer, particularly those which target the lymphatic system, including, but not limited to sodium glycocholate; sodium caprate; N-lauryl-D-maltopyranoside; EDTA; mixed micelle; and those reported in Muranishi Crit. Rev. Ther. Drug Carrier Syst., 7-1-33, which is hereby incorporated by reference in its entirety. Other known absorption enhancers can also be used. Thus, the invention also encompasses a pharmaceutical composition comprising one or more sulfated polysaccharides of the invention and one or more absorption enhancers.

The additional therapeutic agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

Oral Dosage Forms

A compound of the invention or a pharmaceutically acceptable salt, solvate or hydrate thereof and compositions comprising a compound of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Parenteral and Intravascular Dosage Forms

Parenteral and intravascular dosage forms can be administered to patients by various routes including, but not limited to, subcutaneous, intravenous (including bolus injection and constant infusion), intramuscular, and intraarterial. Because their administration typically bypasses patients' natural defenses against contaminants, parenteral and intravascular dosage forms are preferably sterile or capable of being sterilized prior to administration to a patient. Examples of parenteral dosage forms include, but are not limited to, solutions ready for injection, dry products (including, but not limited to lyophilized powders, pellets, and tablets) ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

For intravascular administration, for instance by direct injection into the blood vessel, or surrounding area, it may be desirable to administer the compositions locally to the area in need of treatment. This can be achieved, for example, by local infusion during surgery, by injection, by means of a catheter, or by means of an implant, said implant being of a porous, non-porous, or gelatinous material, including membranes, such as silastic membranes, or fibers. A suitable such membrane is Gliadel® provided by Guilford Pharmaceuticals Inc.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredient of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Although methods and materials similar or equivalent to those described herein can be used in the practice of the present invention, preferred methods and materials are described below. The materials, methods, and examples are illustrative only and not intended to be limiting. Other features and advantages of the invention will be apparent from the detailed description and from the claims.

Kits

This invention therefore encompasses kits which, when used by the medical practitioner, can simplify the identification of subjects and the administration of appropriate amounts of a compound of the invention or a pharmaceutically acceptable salt, solvate or hydrate thereof to a patient.

A typical kit of the invention comprises one or more unit dosage forms of a compound of the invention or a pharmaceutically acceptable salt, solvate or hydrate thereof, and instructions for identification of a subject.

Kits of the invention can further comprise devices that are used to administer a compound of the invention or a pharmaceutically acceptable salt, solvate or hydrate thereof. Examples of such devices include, but are not limited to, intravenous cannulation devices, syringes, drip bags, patches, topical gels, pumps, containers that provide protection from photodegradation, autoinjectors, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

All documents mentioned herein are incorporated herein by reference in their entirety.

EXAMPLES

In order that the invention may be more fully understood, the following examples are provided. It should be understood that these examples are for illustrative purposes only and are not to be construed as limiting the invention in any way.

General Experimental Methodology

1. To identify potent and selective small molecule modulators of MCL-1, a small molecule binding screen by competitive fluorescence polarization assay was conducted. Small molecules were screened in parallel against the FITC-MCL-1 SAHB/MCL-1ΔNΔC interaction and the FITC-BAD BH3/BCL-$X_L$ΔC interaction. Those compounds that preferentially disrupted the FITC-MCL-1 SAHB/MCL-1ΔNΔC interaction were advanced to secondary screening analyses.
2. A series of confirmatory binding assays were performed. First, the competitive binding assay using FITC-MCL-1 SAHB/MCL-1ΔNΔC was repeated using dose-response analysis to confirm dose-responsive binding and determine small molecule $K_i$ values. Subsequently specificity analysis was performed by competitive fluorescence polarization binding assay of small molecules against the interactions of FITC-BID BH3 in combination with MCL-1ΔNΔC, BCL-2ΔC, BCL-$X_L$ΔC, BCL-wΔC, and BFL1/A1ΔC. Small molecules exhibiting high fidelity specificity for MCL-1ΔNΔC over the other anti-apoptotic proteins were advanced to SAR, binding site, and functional analysis. Docking analysis was performed to confirm the compatibility of small molecule structure with an energetically favorable docking site at the structurally defined (i.e. x-ray crystallography) BH3-binding pocket of MCL-1ΔNΔC. Dilutional assays were performed to distinguish between non-covalent and covalent MCL-1 binders. These studies identified a series of covalent interactors; for example, a novel site of interaction for inhibiting MCL-1 binding activity was identified based on covalent modification of MCL-1 by the molecule at cysteine 286. Finally, selective MCL-1 inhibitors were tested in a BAX-mediated liposomal release assay to evaluate their capacity to block the inhibitory/anti-apoptotic activity of MCL-1.
3. Small molecule modulators of MCL-1 were then tested in a cellular apoptosis sensitization assay using OPM2 cells exposed to subcytotoxic doses of TRAIL in the presence or absence of serial dilutions of small molecule. Sensitization activity was also confirmed by use of CalcuSyn analysis of combination treatments.

Methods

Sahb Synthesis.

Hydrocarbon-stapled peptides corresponding to BCL-2 family BH3 domains and their FITC-βAla derivatives were synthesized, purified, and characterized using previously described methodologies[24,27,29].

Anti-Apoptotic Protein Preparation.

Recombinant and tagless MCL-1ΔNΔC, BCL-2 ΔC, BCL-XLΔC, BCL-wΔC, and BFL1/A1ΔC were produced using previously described methods[27,29,31].

Small Molecule Screening.

Small molecule screens were performed at the Institute for Chemistry and Cellular Biology at Harvard Medical School and employed commercial libraries (Asinex, Chembridge, ChemDiv, Enamine, Life Chemicals, and Maybridge). A high-throughput competitive FP binding assay was employed to screen for small molecules that disrupted the interaction between FITC-MCL-1 SAHB (15 nM) and MCL-1ΔNΔC (45 nM). MCL-1ΔNΔC was expressed and purified by FPLC and delivered by automated liquid handler to 384 well plates, followed by addition of small molecule libraries. After a 15 minute incubation at room temperature, FITC-MCL-1 SAHB (15 nM) was added to each well by liquid handler and FP read at equilibrium (e.g. 1 hr). Small molecule hits were re-examined in this assay using serial dilutions of the compounds to confirm dose-responsive inhibition of FITC-MCL-1 SAHB binding.

Confirmatory Binding Analyses.

The most potent hits were advanced to rigorous quantification of binding activity and specificity. First, serial dilutions of small molecule in triplicate were mixed with FITC-MCL-1 SAHB (15 nM), followed by addition to 384-well black Costar plates containing MCL-1ΔNΔC (45 nM) diluted in binding buffer (50 mM Tris, 100 mM NaCl, 0.0625% CHAPS, pH 8.0). The plates were incubated in the dark at room temp until equilibrium was reached (i.e. stabilization of binding isotherms) and FP (mP units) determined using a microplate reader (e.g. Spectramax). $K_i$ values were calculated by nonlinear regression analysis of dose-response curves using Prism software (Graphpad). Small molecule hits were then tested for their ability to dissociate FITC-BAK BH3 from MCL-1ΔNΔC in a competitive FP assay, performed as described above except that small molecule dilutions were added to a solution of FITC-BAK BH3 (25 nM) and MCL-1ΔNΔC (250 nM) to simulate a physiologic displacement of pro-apoptotic BAK from the inhibitory MCL-1 protein. For rigorous specificity analysis, the identical competitive FP-type experiment was performed except that serial dilutions of small molecule hits were mixed with the pan-anti-apoptotic binder FITC-BID BH3 (15 nM), followed by addition to plates containing either MCL-1ΔNΔC, BCL-2ΔC, BCL-X$_L$ΔC, BCL-wΔC, or BFL1/A1ΔC. We used pGEX vectors to express GST-MCL-1ΔNΔC, BCL-2ΔC, BCL-X$_L$ΔC, BCL-wΔC, and BFL1/A1ΔC, followed by thrombin cleavage and FPLC-based gel filtration chromatography. Of note, the C-terminal alpha-helix was deleted from each of these constructs to facilitate protein expression and purification; an additional N-terminal deletion of MCL-1 was performed to further enhance expression, purity, and stability. FP analysis was performed as above and those molecules showing exclusive binding activity for MCL-1ΔNΔC were advanced to structural docking and functional testing.

Dilution Assay.

MCL-1ΔNΔC (2 μM, 500 mL) was incubated with compound (at a ratio well above each previously determined $EC_{50}$ value) for 1 hour at room temperature in FP buffer (100 mM NaCl, 50 nM Tris, pH 8). A small sample was taken as a pre-dilution control. Compound-treated protein and unmodified protein were then diluted to a volume of 20 mL, and subsequently re-concentrated to 500 mL using 10K centrifugal filter units (Amicon). FP binding analysis was performed as described above by adding serial dilutions of compound-modified MCL-1 and unmodified MCL-1, both before and after dilution, followed by FITC-BID BH3 (15 nM) to a 96-well black flat bottom plate (Costar). FP measurements and analyses are then performed as described above.

Identification of Covalent Modification Site by Mass Spectrometry.

MCL-1ΔNΔC (90 μM) was incubated with a 1:1.25 ratio of compound for 2 hours at room temperature in 150 mM NaCl, 50 mM Tris, pH 7.4. Excess compound was removed by gel filtration and the protein was digested with trypsin overnight at 37° C. Peptides were analyzed by nano-LC/ESI/MS using a vented column assembly as described (Ficarro et al., 2009)[34]. Briefly, peptides were injected using an autosampler and HPLC (Waters NanoAcquity) onto a self-packed precolumn (4 cm, 100 μm I.D., POROS10R2, Applied Biosystems) and gradient eluted (0-30% B in 20 minutes, A=0.2 M acetic acid in water, B=acetonitrile with 0.2M acetic acid) to the resolving column (self-packed 30 μm I.D., 12 cm of 5 μm Monitor $C_{18}$, Column Engineering) and introduced to the mass spectrometer (Thermo Fisher LTQ-Orbitrap XL) via EST (spray voltage=2.2 kV). The top 8 most abundant precursors in each MS scan (image current detection, resolution=30,000) were subjected to CAD (electron multiplier detection, collision energy=35%). A separate targeted nano-LC/ESI/MS experiment was performed with compound-modified peptide (e.g. TINQES*CIEPLAESITDVLVR [*C=modified cysteine)]), which was subjected to HCD (higher energy collisionally activated dissociation).

Liposomal Release Assay.

Liposomes are prepared from a mixture of lipids that reflect the composition of the outer mitochondrial membrane as previously described in detail (Pitter et al., 2008)[31]. Aliquots of mixed lipids (1 mg total) are stored in glass at −20° C. under nitrogen, and before use, resuspended in liposome assay buffer (10 mM HEPES, 200 mM KCl, 1 mM $MgCl_2$, pH 7) with 12.5 mM of the fluorescent dye ANTS (8-aminonaphthalene-1,3,6-trisulfonic acid, disodium salt) and 45 mM of the quencher DPX (p-xylene-bis-pyridinium bromide). The resulting slurry is vortexed for 10 minutes and freeze-thawed five times alternating between liquid nitrogen and a 40° C. water bath. The solution is then passed through an Avanti Mini-Extruder Set (#610000) equipped with a 100-nm filter, followed by passage through a Sepharose column (GE Healthcare) to remove residual ANTS/DPX. The lipsomes are brought up to a volume of 3 mL to produce a final liposome stock. For the liposomal release assay, a total volume of 30 μL is used in 384 well black flat bottom plates (Costar), and baseline fluorescence measurements of 8 μL liposomes are made for 10 minutes using the Tecan Infinite M1000 (excitation: 355 nm, emission: 520 nm). Following the baseline read, recombinant MCL-1ΔNΔC pre-incubated with a 1:1 ratio of compound is added to the liposomes. Next, 20 nM caspase-cleaved mouse BID (R&D systems) and 250 nM purified recombinant monomeric BAX is added, and fluorescence measurements (F) are recorded every minute from time zero (F0) until the release readings plateau. The liposomes are then quenched with 1% Triton X-100 (100% release; F100), and percent ANTS/DPX release is calculated as $((F-F0)/(F100-F0))\times 100$.

Cytochrome c Release Assays.

Mouse liver mitochondria (0.5 mg/mL) are isolated and release assays performed as described[31]. Mitochondria are incubated with a serial dilution of MCL-1 targeting small molecule, singly or in combination with BID BH3, and after 40 minutes, the pellet and supernatant fractions are isolated and cytochrome c quantitated using a colorimetric ELISA assay (R&D Systems). Percent cytochrome c released into the supernatant (% $cytoc_{sup}$) from releasable mitochondrial pools was calculated according to the following equation: % cytoc=$[(cytoc_{sup}-cytoc_{backgr})/(cytoc_{total}-cytoc_{backgr})]*100$, where background release represents cytochrome c detected in the supernatant of vehicle-treated (1% DMSO) samples and total release represents cytochrome c measured in 1% Triton-X 100 treated samples. All experimental conditions are also tested on $Bak^{-/-}$ mitochondria to ensure that the observed cytochrome c release from wild-type mitochondria derives from BAK activation.

Immunoprecipitation Assay.

MCL-1-expressing cancer cells ($10\times10^6$) are incubated with the MCL-1 targeting small molecule or vehicle in serum-free media at 37° C. for 4 hours, followed by serum replacement for an additional 6 hours. After cellular lysis in 50 mM Tris (pH 7.4), 150 mM NaCl, 1 mM EDTA, 1 mM DTT, 0.5% NP40 and complete protease inhibitor pellet, cellular debris is pelleted at 14,000 g for 10 minutes at 4° C. The supernatant is exposed to pre-equilibrated protein A/G sepharose beads and the pre-cleared supernatant subsequently incubated with anti-MCL-1 antibody for 1.5 hours at 4° C., followed by the addition of protein A/G sepharose beads for 1 hour. The beads are pelleted and washed with lysis buffer for 10 minutes at 4° C. The washed bead are then pelleted, heated to 90° C. for 10 minutes in SDS loading buffer, analyzed by SDS/PAGE, and then immunoblotted for MCL-1 and BAK.

Crystallography.

Crystallization conditions for lead small molecule-MCL-1ΔNΔC complexes are screened using 96-well sitting drop plates set up using a Phoenix crystallization robot. Initial conditions include HT Index Screen, JSCG+ Suite, and Pro-Complex Suite. Screening around the best hit, including varying pH, salt, and detergent concentrations, are performed to identify the best condition for crystal growth. Once generated, the crystals are removed, washed in the crystallization buffer, and subjected to mass spectroscopy to verify the presence of compound and protein within the crystal. The crystal is then soaked in cyroprotectant, flash frozen, and stored in liquid nitrogen. Suitable crystals are examined at the Argonne National Laboratory synchrotron facility. Phases are obtained by molecular replacement followed by data analysis and refinement (Phaser, Phenix, and Coots software).

Cellular Apoptosis Induction Assays.

Small molecule inhibitors of MCL-1 were screened in MCL-1-expressing cancer cell lines, such as OPM-2 (multiple myeloma) cells. The cells are treated with the small molecule MCL-1 inhibitor, alone or in combination with subtherapeutic pro-apoptotic stimuli (e.g. TRAIL, Fas ligand, ABT-737), and then cell viability is measured at 48 hours by MTT assay performed according to the manufacturer's protocol (Roche) and quantitated by an ELISA microplate reader (Biorad). $IC_{50}$ values were determined by nonlinear regression analysis using Prism software (Graphpad). Small molecules that decrease cell viability are then screened for cellular apoptosis induction by annexin V binding and FACS analysis, and by cell fractionation-based mitochondrial cytochrome c release, as described[28]. Apoptosis is also correlated with in situ dissociation of the MCL-1/BAK complex (immunoprecipitation) performed as described above. As an additional measure of small molecule MCL-1 specificity, the identical experiments are conducted on wild-type vs. $Mcl-1^{-/-}$ MEFs, to explicitly link the selective MCL-1 targeting capacity of the small molecules to sensitization of apoptosis. The caspase-dependency of small molecule activity is also confirmed by monitoring for blockade of activity upon co-treatment with the pan-capase inhibitor Z-VAD.

Pharmacokinetic Analyses.

Lead small molecules undergo pharmacokinetic (PK) analysis in mice, performed in conjunction with the DF/HCC Clinical Pharmacology Core. LC/MS-based analytical assays are developed in order to detect and quantify compound levels in plasma. For PK analysis, small molecules (e.g. 10, 50, 100 mg/kg) are injected by tail vein or intraperitoneally into male C57/BL6 mice. Blood samples are withdrawn by retro-orbital bleed at various time points and plasma isolated for compound quantification, followed by calculation of plasma half-life, peak plasma levels, total plasma clearance, and apparent volume of distribution. Small molecules that exhibit selective MCL-1 targeting in cells and exhibit a favorable pharmacokinetic profile re advanced to in vivo testing.

In Vivo Efficacy Studies.

Small molecule-sensitive cancer cell lines are retrovirally transduced to achieve stable luciferase expression (pMMP-LucNeo) and transplanted into SCID beige mice as previously described[27,32]. Initial xenograft studies examine 5 mouse cohorts (n=10), treated with either vehicle alone, low or high dose small molecule alone, or low/high dose small molecule in combination with subtherapeutic dosing of pro-apoptotic stimuli (e.g. TRAIL, ABT-737, doxorubicin, etoposide, dexamethasone). Starting on experimental day 1, mice receive a once daily tail injection of small molecule (e.g. 25 or 100 mg/kg, with or without combination treatment). For alternate day in vivo tumor imaging, mice are anesthetized with inhaled isoflurane and treated concomitantly with intraperitoneal injection of D-luciferin. Photonic emission is imaged (2 min exposure) using a Xenogen In Vivo Imaging System and total body bioluminescence quantified by the integration of photonic flux (photons/sec) using Xenogen's Living Image Software. The survival distributions of experimental mice are determined using the Kaplan-Meier method and compared using the log-rank test. The Fisher's exact test is used to compare the proportion of mice who fail treatment, where treatment failure is defined as progression or death, and success as stable disease or regression. If a treatment response is observed with a particular small molecule, three additional cohorts, treated with either vehicle, small molecule, or small molecule combination will be used for pharmacodynamic studies in which pro-apoptotic activity is evaluated in tissues by TUNEL and activated caspase-3 immunohistochemical staining.

Examples

Identification of MCL-1 Selective Small Molecules by a Competitive Fluorescence Polarization Binding Assay Using FITC-MCL-1 SAHB and MCL-1ΔNΔC.

A high-throughput competitive FP binding assay was employed to screen for small molecules that disrupted the interactions between FITC-MCL-1 SAHB/MCL-1ΔNΔC and FITC-BAD BH3/BCL-$X_L$ΔC (FIG. 1). Compounds were ranked based upon their selectivity for MCL-1ΔNΔC over BCL-$X_L$ΔC targeting, and tabulated (see Table 1 (including Subtables Table 1-A through Table 1-P)).

The Structures of Small Molecule/MCL-1 Complexes Provide a Template for Refining MCL-1 Binding Activity and Specificity.

Using the crystal structure of MCL-1ΔNΔC, the identified small molecules were docked onto the BH3-binding pocket of MCL-1ΔNΔC to analyze the location and energetic favorability of interaction. The compounds covered discrete subregions of BH3-binding pocket topography (FIG. 2), providing a blueprint for engineering selective, larger molecules that incorporate combinations of molecules or their subfragments to engage the complex and extended BH3-binding surface of MCL-1.

Subclassification of Selective MCL-1 Inhibitors Based on Non-Covalent Vs. Covalent Interactions.

Figure 2A:
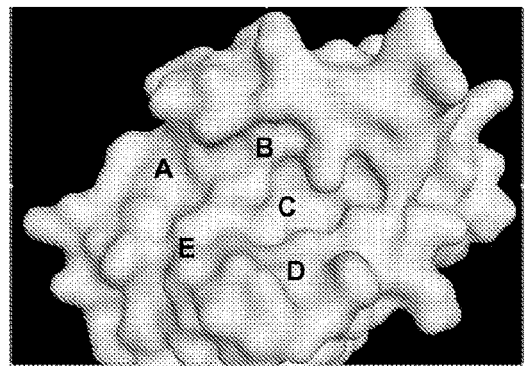
FIG. 2A shows a surface view of the BH3-binding pocket of MCL-1ΔNΔC from the X-ray structure of MCL-1 (PDB ID: 2PQK), with discrete topographic regions of the binding surface labeled A-E.
Figure 2B:
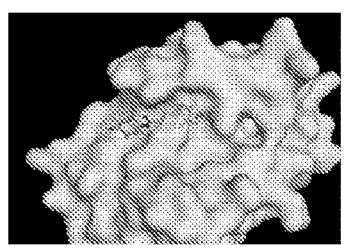
FIG. 2B shows examples of selective small molecule binders of MCL-1ΔNΔC engaging discrete topographic regions (labeled A-E) of the BH3-binding pocket, as rendered by molecular docking. Since certain small molecules cover distinct regions of the pocket, synthetic combinations of molecules or fragments thereof can yield a larger molecule that selectively binds a greater surface area of the BH3-binding pocket. The identified topographic coverage of select molecules include compounds 1, (A+B); 2, (B+C); 3, (C+D); 4, (A+E); 5, (A+B+C); 6, (E+B+C).
Figure 2B:
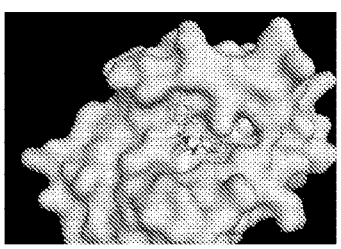
Figure 2B:
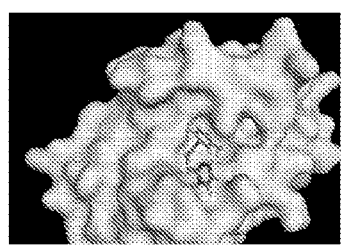
Figure 2B:
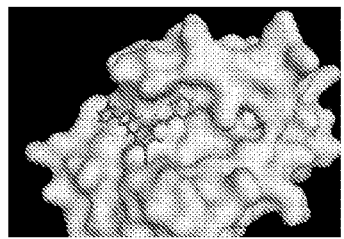
Figure 2B:
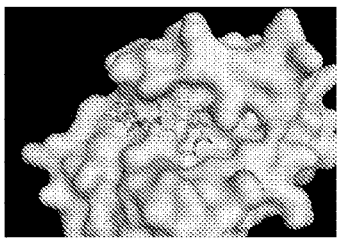
Figure 2B:
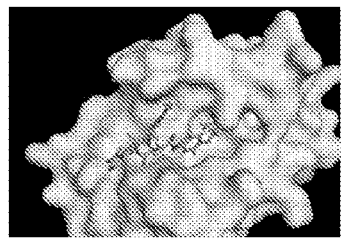
Figure 2C:
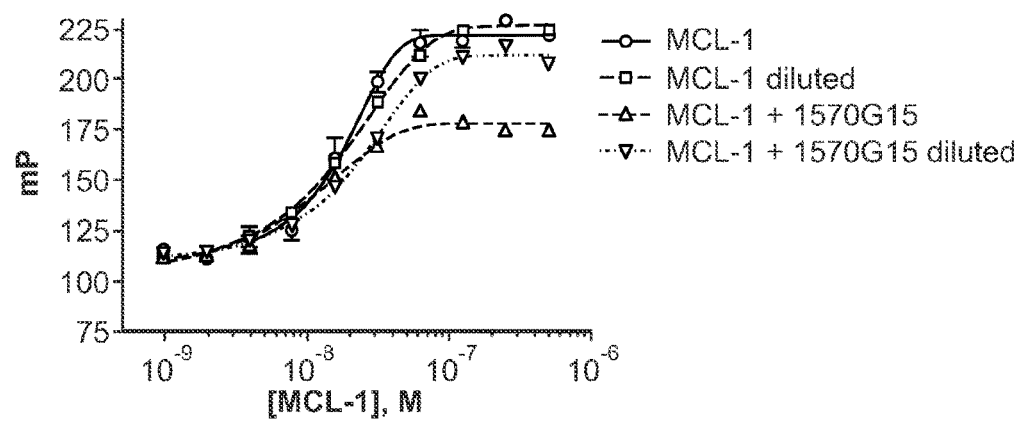
FIG. 2C shows the results of a dilutional assay that revealed selective small molecule binders can be subclassified based on engaging MCL-1 through noncovalent or covalent interactions. FITC-BID BH3 binding to MCL-1 is restored upon dilution in the top panel (molecule 1570G15), whereas competitive FITC-BID BH3 binding cannot be restored by dilution once MCL-1 is exposed to small molecules 1725P16 and 1579E07. These data suggest that 1570G15 engages MCL-1 through non-covalent interactions, whereas 1725P16 and 1579E07 covalently modify MCL-1, preventing re-engagement by FITC-BID BH3 even after protein dilution.
Figure 2C:
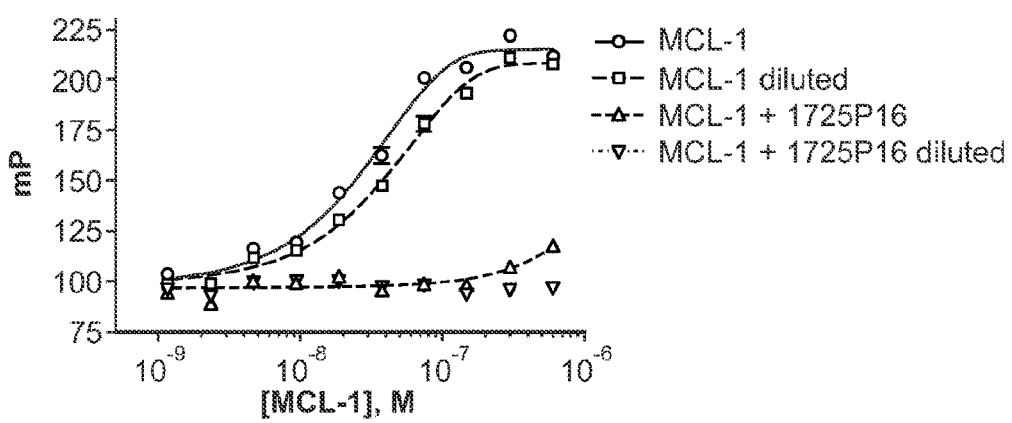
Figure 2C:
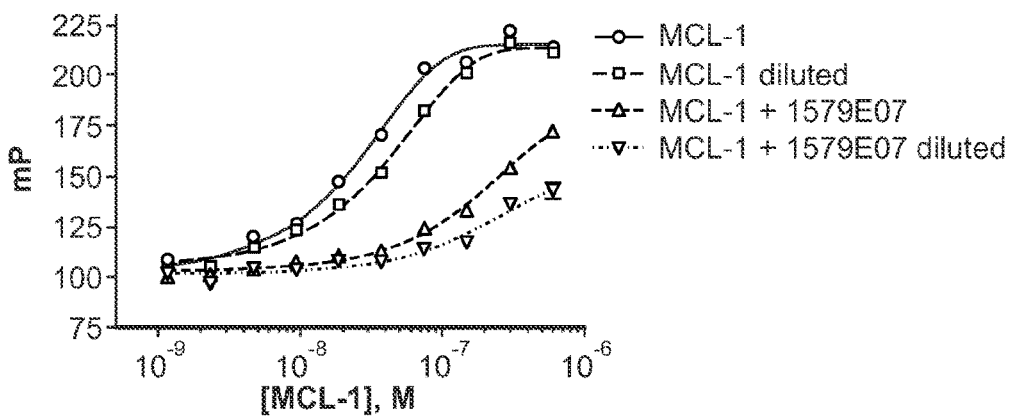

To examine the mechanism of small molecule binding to MCL-1, the compounds were subjected to a rapid dilution assay (FIG. 2C). Briefly, MCL-1ΔNΔC was pre-incubated with the small molecule inhibitors prior to dilution with buffer. The solution was concentrated to its original volume and fluorescence polarization was performed. Compounds that bind covalently will remain bound to the protein, whereas compounds that bind reversibly will be exchanged upon dilution. As a positive control, the rapid dilution assay confirmed that gossypol (1570G15) bound reversibly to MCL-1ΔNΔC (FIG. 2C, top panel). In contrast, 1725P16 and 1597E07 failed to exchange upon dilution, indicating that the compounds bind and covalently modified MCL-1ΔNΔC (FIG. 2C, middle, bottom panels).

Identification of a Novel Interaction Site for MCL-1 Inhibition Based on C286 Engagement.

Figure 2D:
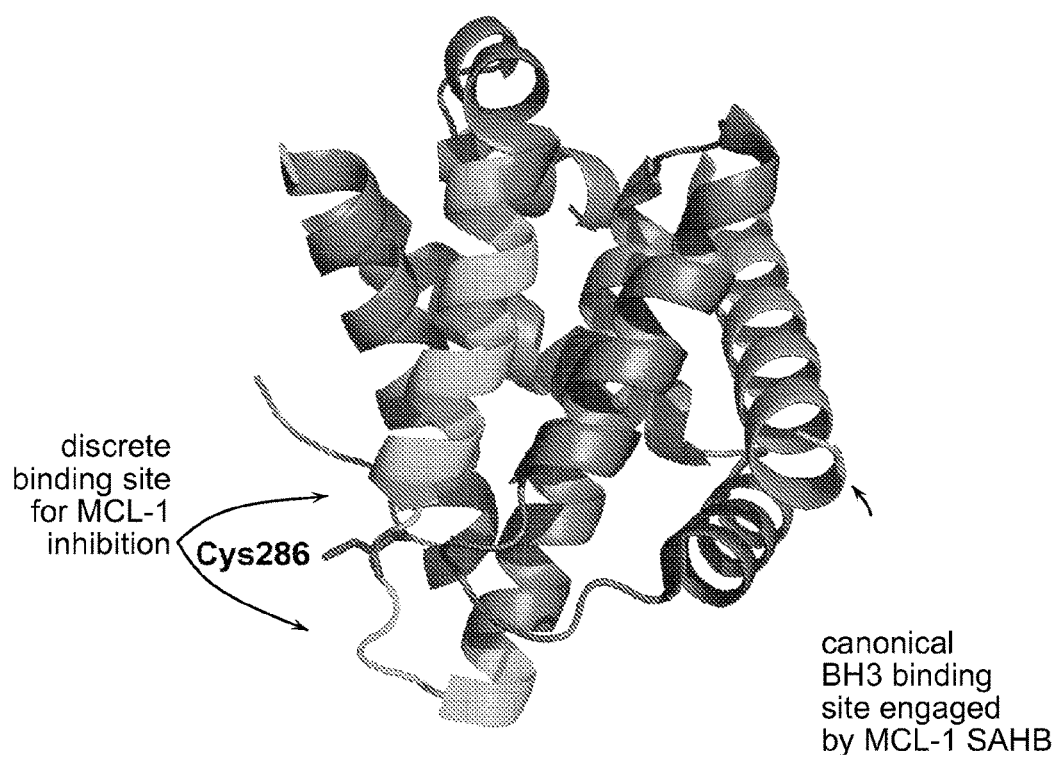
FIG. 2D shows that a subgroup of MCL-1 inhibitor molecules covalently reacted with C286 of MCL-1 at a novel interaction site. Proteomic analysis determined that a subset of molecules that covalently modify MCL-1 react at C286 of the identified tryptic fragment, revealing a discrete binding site for MCL-1 that differs in location from the canonical BH3 binding site engaged by MCl-1 SAHB.
Figure 2E:
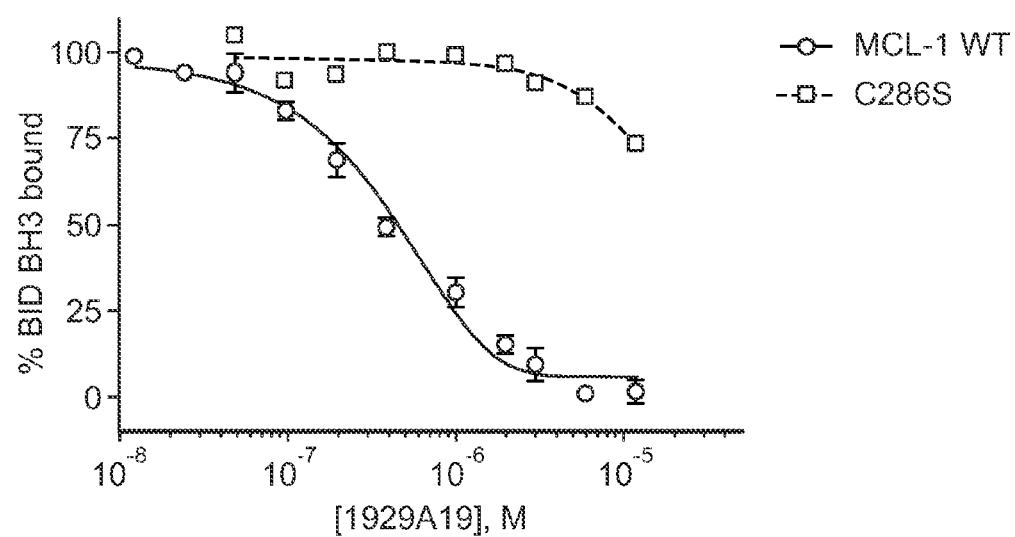
FIG. 2E demonstrates that C286S mutagenesis abrogates binding of this subgroup of molecules, confirming engagement of a novel interaction site for MCL-1 inhibition. Molecules that covalently modify MCL-1 at C286 (1929A19; 161N08 [Class A]) effectively block FITC-BID BH3 binding to MCL-1. This small molecule activity is specifically abrogated by C286S mutagenesis, implicating interactions at a novel site in the modulation of binding activity at the canonical BH3 binding pocket of MCL-1.
Figure 2E:
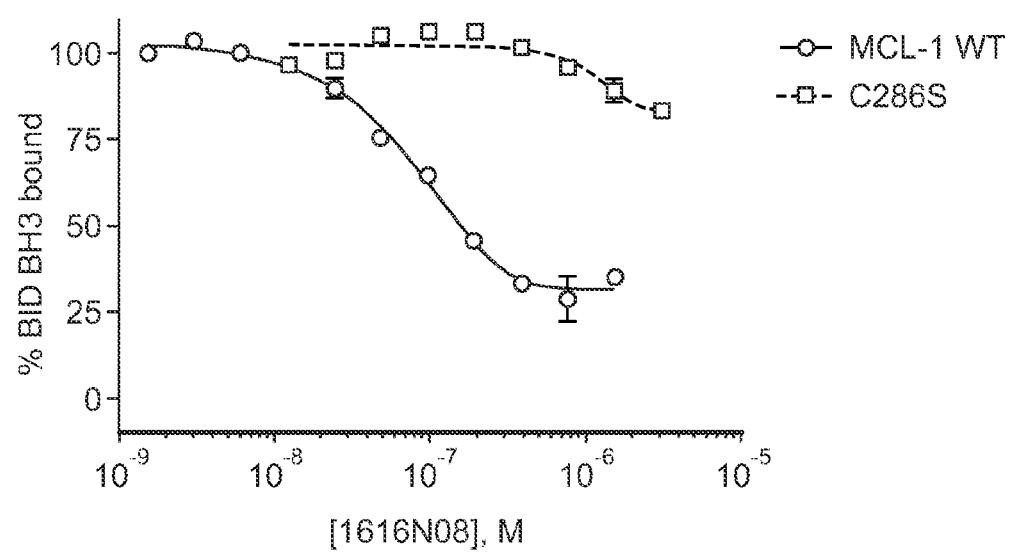

To localize sites of covalent modification, small molecule-treated MCL-1ΔNΔC (e.g. 1929A19) was subjected to mass spectrometry. An additional MALDI peak was observed for small molecule-treated protein, with the increase in mass corresponding to the molecular weight of the covalently tethered compound. The MCL-1ΔNΔC-adduct was further subjected to tandem MS/MS, which revealed cysteine 286 as the site of modification for 1929A19 (FIG. 2D). Importantly, cysteine 286 is not located at the canonical BH3 binding pocket (FIG. 2D), indicating that engagement of this novel binding site can allosterically regulate MCL-1's anti-apoptotic/BH3-binding activity. To confirm the functional importance of C286 engagement, a C286S construct of MCL-1ΔNΔC was generated by site-direct mutagenesis and small molecule binding activity was compared in competitive FP assays using FITC-BID BH3 and the wild-type and mutant MCL-1ΔNΔC proteins. Whereas 1929A19 and 1616N08 competed with FITC-BID BH3 for MCL-1ΔNΔC binding, the molecules failed to engage the C286S construct of MCL-1ΔNΔC, as demonstrated by the capacity of FITC-BID BH3 to maintain binding activity toward MCL-1ΔNΔC $C_{286}S$ in the presence of the compounds.

Confirmation of Small Molecule Binding Activity and Selectivity by Use of Competitive Binding Assays.

Figure 3A:
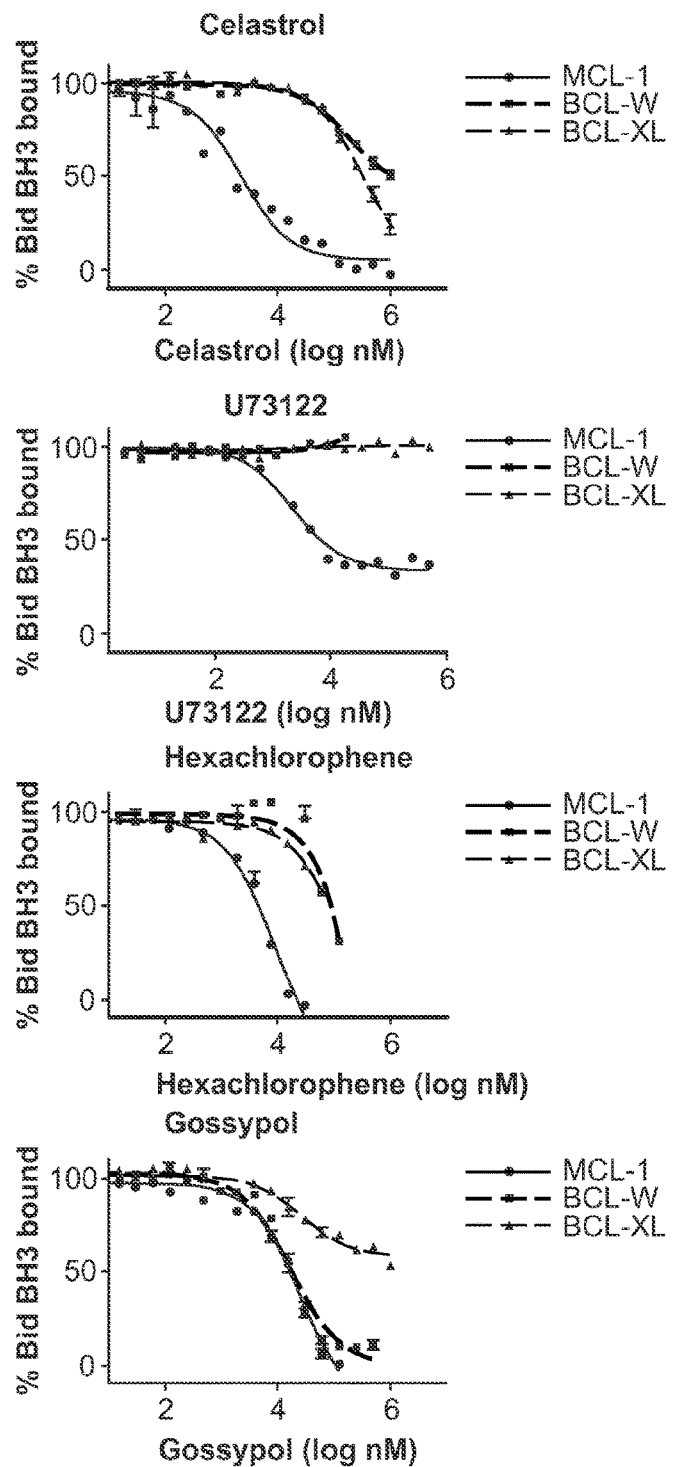
FIG. 3A shows the degree of MCL-1 selectively as determined by competitive fluorescence polarization binding assays (FPA) in a secondary screen of small molecule hits from a bioactive library against FITC-BID BH3/anti-apoptotic protein interactions.

To verify the capacity of the identified small molecules to selectively target MCL-1ΔNΔC, small molecule hits were tested for their differential ability to dissociate FITC-BID BH3 from a panel of anti-apoptotic proteins, including MCL-1ΔNΔC C, BCL-2ΔC, BCL-XLΔC, BCL-wΔC, and BFL1/A1ΔC. As exemplified in FIGS. 3 and 4, small molecules identified as MCL-1ΔNΔC selective indeed exhibited preferential displacement of FITC-BID BH3 from MCL-1ΔNΔC compared to the other anti-apoptotic proteins tested.

Structure-Activity Relationship Analysis of Selective MCL-1 Inhibitors.

Chemical derivatives of class A (FIG. 4C) and J (FIG. 4D) molecules demonstrated significant differences in binding activity. Importantly, the five-member thiotriazole ring at position R1 of class A increased binding affinity for MCL-1ΔNΔC compared to smaller, non-aromatic substituents. At the R2 position, aromatic residues were favored with small hydrophobic side chains or hydrogen bond acceptors at the para-position of the phenyl ring. For class J, small aliphatic groups were well tolerated at the R1 position, and the trihydroxyphenyl ring at the R2 position demonstrated superior binding affinity for MCL-1ΔNΔC. Finally, five- or six-member aromatic rings were favored at the R3 position. Specifically, analogs that contained methyl substituents at R3 displayed no activity unless paired with a large aliphatic group at the R1 position.

Small Molecule MCL-1 Binders Sensitize Cancer Cells to Pro-Apoptotic Stimuli.

Figure 5A:
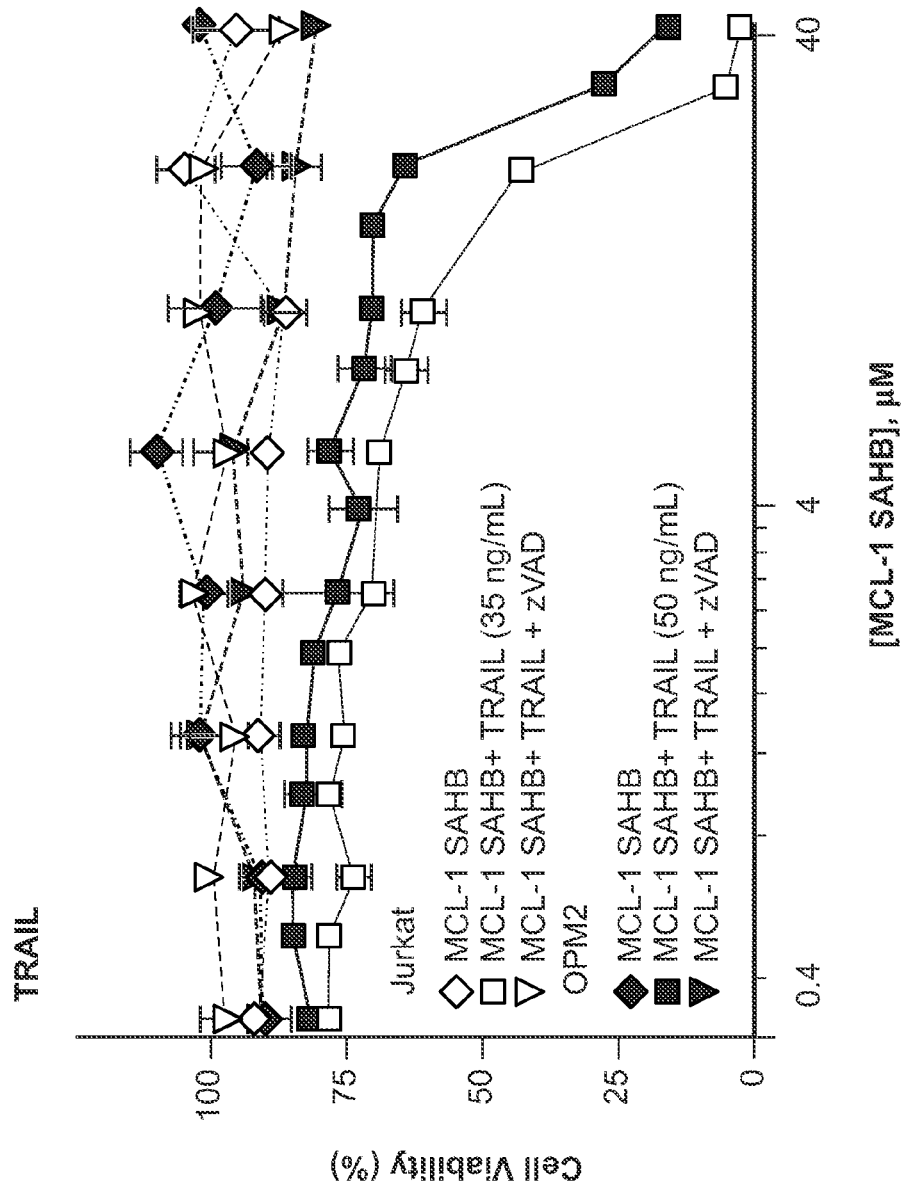
FIG. 5A shows that a SAHB peptide selective for MCL-1 sensitizes TRAIL-induced and caspase-dependent cell death of Jurkat T-cell leukemia and OPM2 multiple myeloma cells. MCL-1-targeting small molecule hits synergize with TRAIL to induce cell death of OPM2 cells.
Figure 5B:
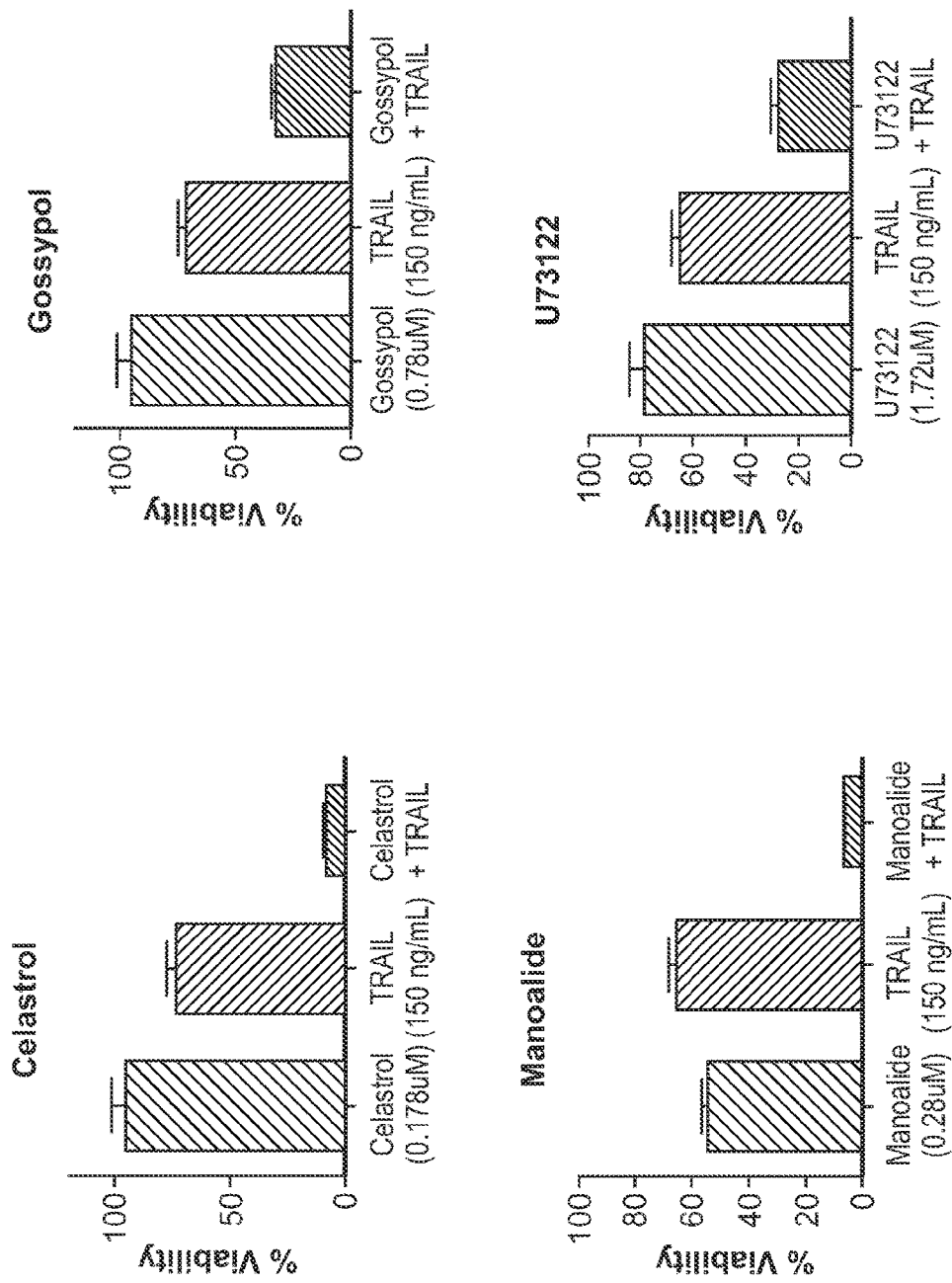
FIG. 5B shows that small molecule bioactives that target MCL-1 also sensitize the capacity of TRAIL to inhibit viability of OPM2 cells, as has been shown for selective targeting of MCL-1 with MCL-1 SAHB (FIG. 5A) and for selective knock-down of MCL-1 with siRNA.

Cancer cells that depend on MCL-1 for survival were treated with selective small molecule MCL-1ΔNΔC binders in combination with other pro-apoptotic agents to assess for synergistic anti-tumor activity. As exemplified in FIG. 5, small molecule bioactives synergized with TRAIL to kill OPM2 multiple myeloma cells, as assessed by MTT viability assay and by combination treatment analysis using CalcuSyn software.

Selective MCL-1 Inhibitors Block the Anti-Apoptotic Function of MCL-1 in a BAX-Mediated Liposomal Release Assay.

Figure 6:
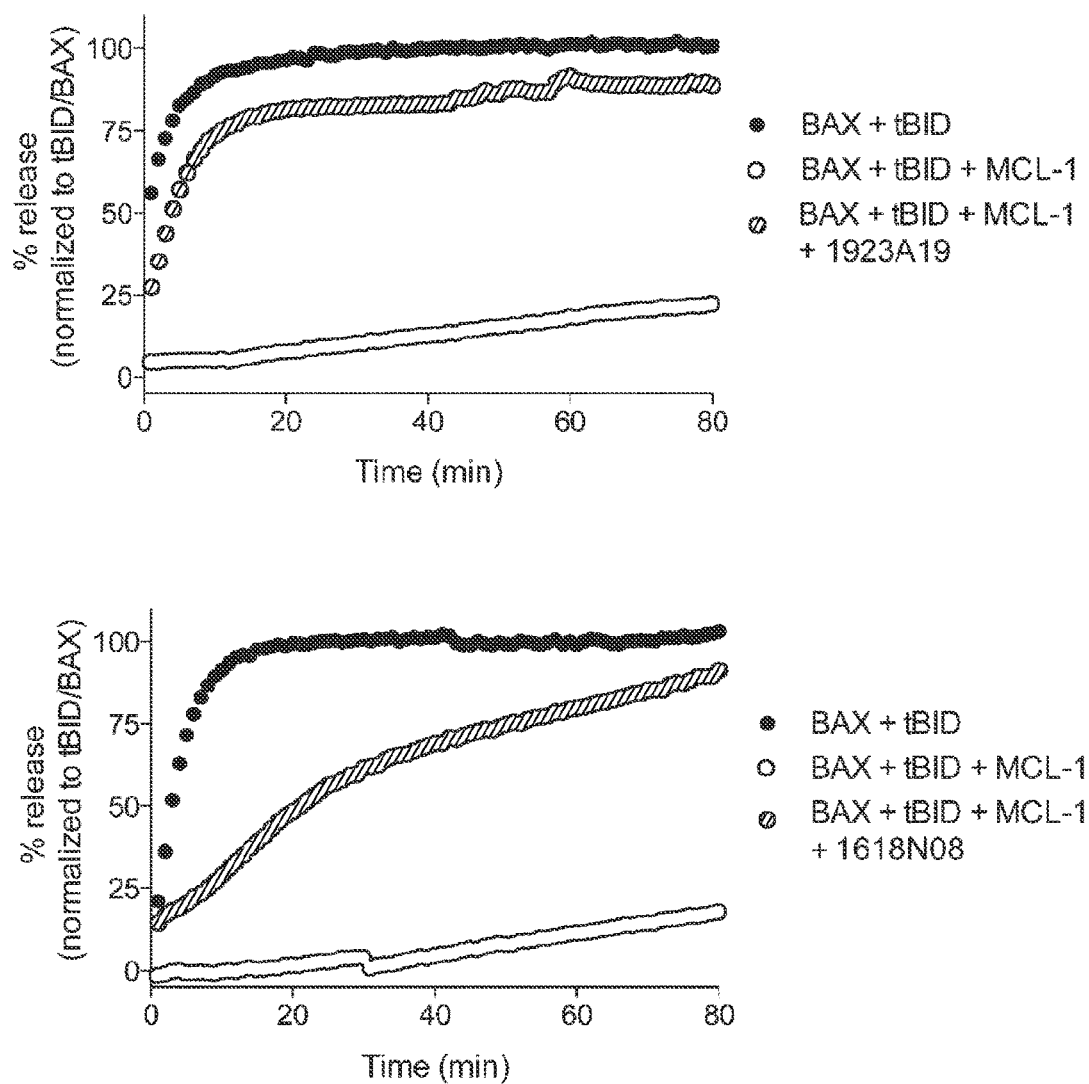
FIG. 6 shows that selective MCL-1 inhibitor molecules block the anti-apoptotic activity of MCL-1 in a BAX-mediated liposomal release assay. MCL-1 blockade of tBID-induced, BAX-mediated liposomal release is inhibited by pretreatment of MCL-1 with the selective small molecule MCL-1 inhibitors.

The liposomal release assay is designed to mimic the functional release of mitochondrial cytochrome c by formation BAX-containing pores within the outer mitochondrial membrane. Here, recombinant full length BAX was incubated with recombinant tBID in the presence or absence of MCL-1ΔNΔC. As demonstrated in FIG. 6, tBID triggered BAX-mediated release of the fluorophore from the liposome in a time-dependent manner. MCL-1ΔNΔC blocked BAX activation, inhibiting fluorophore release. By inhibiting MCL-1ΔNΔC, 1929A19 and 1616N08 dose-responsively re-instated tBID-induced, BAX-mediated liposomal release of the fluorophore, highlighting the capacity of the small molecule MCL-1 inhibitors to block the anti-apoptotic activity of MCL-1.

TABLE 1-A

| Structure | MCL-1% Bound | BCL-XL % Bound | Spec Values |
|---|---|---|---|
| 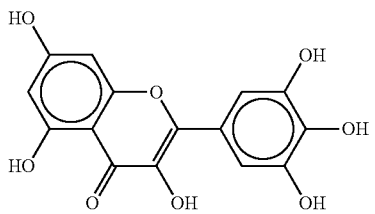 | 34.13126397 | 102.3629331 | 68.231669 |

-continued
| | | | |
|---|---|---|---|
| 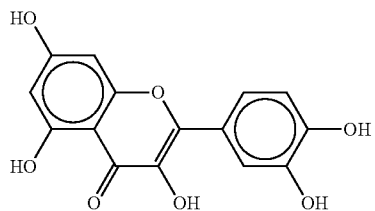 | 16.68871081 | 105.3416001 | 88.652889 |
| 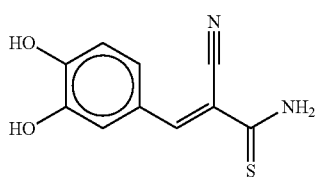 | 34.54623163 | 100.760843 | 66.214611 |
| 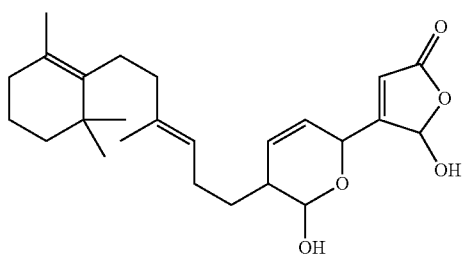 [SMILES: CC1=C(CC/C(C)=C/CCC2C=CC(C3=CC(=O)OC3O)OC2O)C(C)(C)CCC1] | 35.01128141 | 106.8345939 | 71.823312 |
| 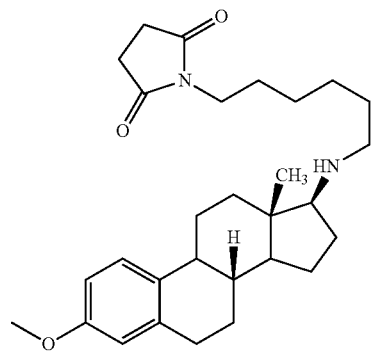 | 56.60157162 | 106.2747212 | 49.67315 |
| 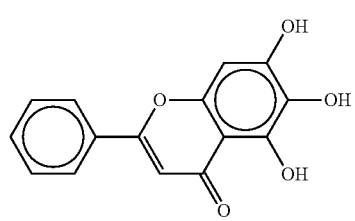 | 10.32290702 | 104.1661092 | 93.843202 |
| 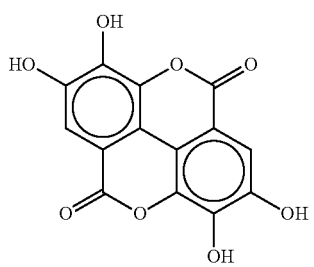 | 1.259544221 | 90.57802572 | 89.318482 |

-continued

| Structure | | | |
|---|---|---|---|
| (bithionolate-like: dichlorophenolate-S-tetrachlorophenyl) | 27.20036677 | 100.4228001 | 73.222433 |
| PL-157DG15 (disodium salt, polyphenolic dimer with isopropyl, methyl, aldehyde, and hydroxyl groups) | 3.955080904 | 101.0243434 | 97.069262 |
| (hexachlorophene: bis(3,5,6-trichloro-2-hydroxyphenyl)methane) | 41.01271009 | 100.3606236 | 59.347914 |
| (celastrol-type triterpenoid carboxylic acid with quinone methide) | 32.90443509 | 97.09434568 | 64.189911 |
| (pentagalloyl glucose / tannin, galloylated glucopyranose) | 15.93536133 | 98.2573418 | 82.32198 |

-continued
TABLE 1-B
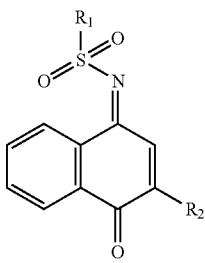
R1 = heterocycle or aromatic
R2 = H or S-heterocycle or aromatic
| Structure | MCL-1% Bound | BCL-XL % Bound | Spec Values |
|---|---|---|---|
| 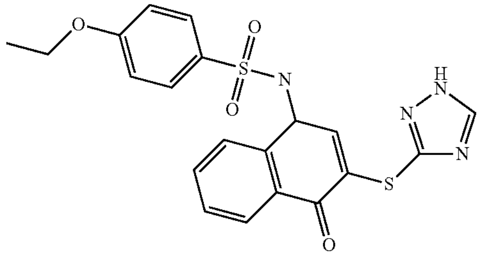 [SMILES: CCOc1ccc(S(=O)(=O)NC2C=C(Sc3nc[nH]n3)C(=O)c3ccccc32)cc1] | 2.332623997 | 103.4341651 | 101.1015411 |
| 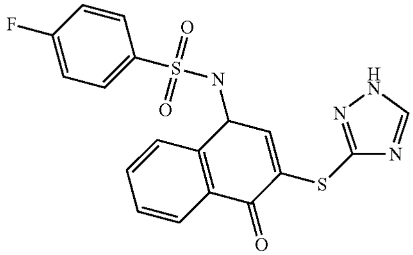 [SMILES: O=C1C(Sc2nc[nH]n2)=CC(NS(=O)(=O)c2ccc(F)cc2)c2ccccc21] | 4.951710591 | 96.11650485 | 91.16479426 |
| 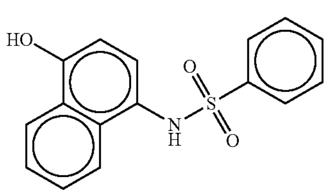 | 19.67020024 | 96.38730675 | 76.71710652 |
| 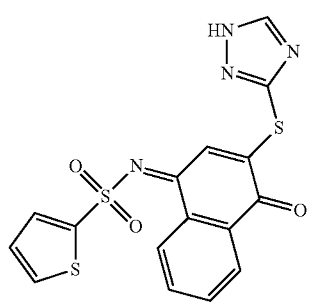 [SMILES: O=C1C(Sc2nc[nH]n2)=C/C(=N/S(=O)(=O)c2cccs2)c2ccccc21] | 19.74954984 | 93.16376474 | 73.4142149 |

-continued
| Structure | | | |
|---|---|---|---|
| 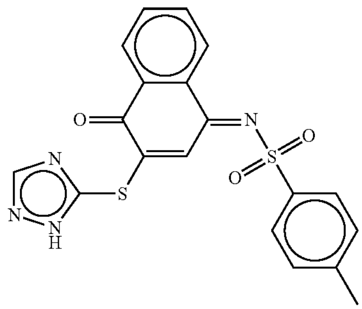 | 35.6 | 98.3 | 62.7 |
| 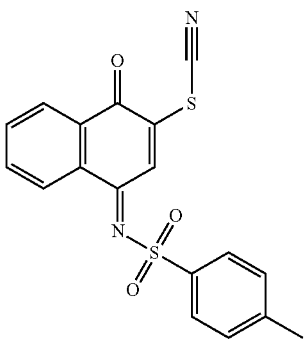 [SMILES: Cc1ccc(S(=O)(=O)/N=C2\C=C(SC#N)C(=O)c3ccccc32)cc1] | 36.15465782 | 91.34577213 | 55.19111431 |
TABLE 1-C
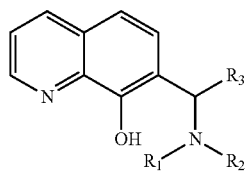
where R3 = heterocycle or aromatic
| Structure | MCL-1% Bound | BCL-XL % Bound | Spec Values |
|---|---|---|---|
| 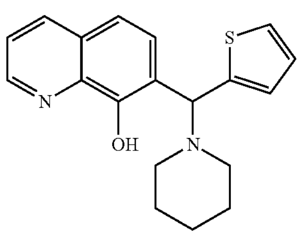 [SMILES: Oc1c(C(c2cccs2)N2CCCCC2)ccc2cccnc12] | 9.463295931 | 115.1848233 | 105.7215274 |
| 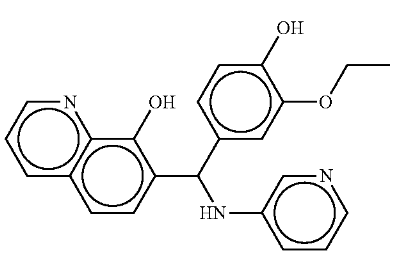 | −0.3 | 108.4 | 108.7 |

-continued
| | | | |
|---|---|---|---|
| 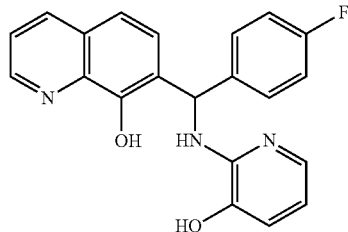 [SMILES: Oc1cccnc1NC(c1ccc(F)cc1)c1ccc2cccnc2c1O] | 42.48636709 | 113.7228826 | 71.23651547 |
| 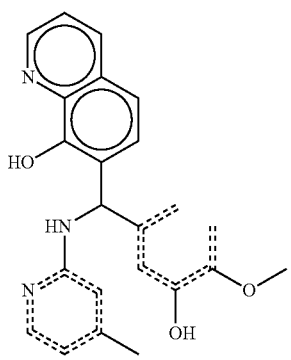 | 27.16644285 | 93.0177803 | 65.85133746 |
| 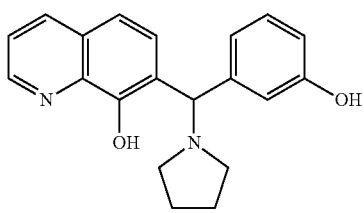 [SMILES: Oc1cccc(C(c2ccc3cccnc3c2O)N2CCCC2)c1] | 43.7012494 | 106.4084449 | 62.70719545 |
| 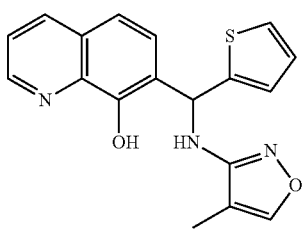 [SMILES: Cc1conc1NC(c1cccs1)c1ccc2cccnc2c1O] | 58.33277892 | 103.7511722 | 45.41839332 |

-continued

TABLE 1-D

| Structure | MCL-1 % Bound | BCL-XL % Bound | Spec Values |
|---|---|---|---|
| 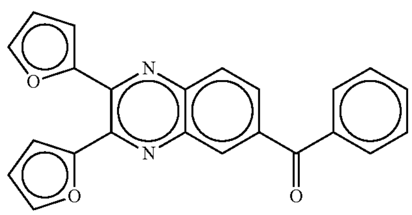 | 14.6 | 101.3 | 86.7 |
| 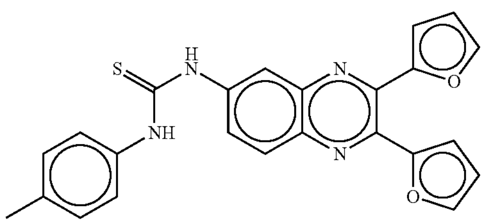 | −2.04714193 | 75.96629122 | 78.01343315 |
| 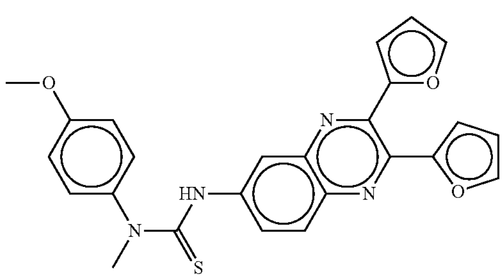 | 8.332108744 | 81.17127433 | 72.83916559 |
| 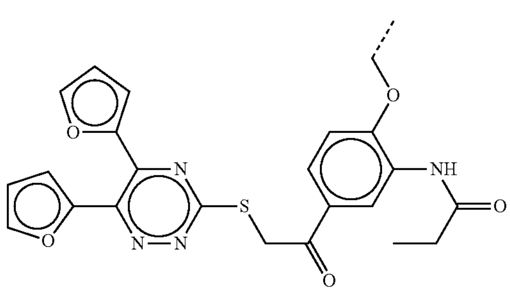 | 43.2 | 109.5 | 66.3 |

-continued
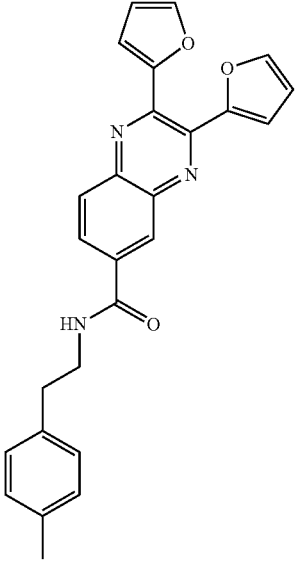 [SMILES: Cc1ccc(CCNC(=O)c2ccc3nc(-c4ccco4)c(-c4ccco4)nc3c2)cc1]
| | | |
|---|---|---|
| 35.72624681 | 99.74101397 | 64.01476715 |
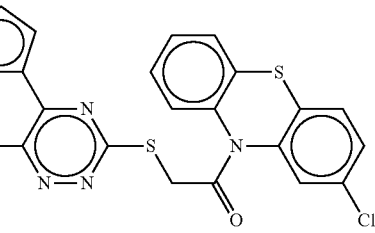
| | | |
|---|---|---|
| 37.6 | 98.3 | 60.7 |
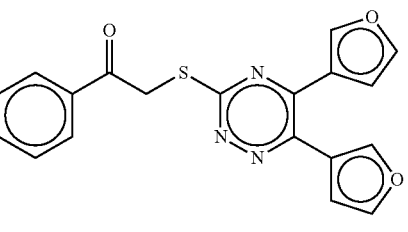
| | | |
|---|---|---|
| 45.37762426 | 98.52069172 | 53.14306746 |
TABLE 1-E
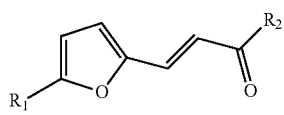
where R1 = amide or ester
R2 = heterocycle or aromatic
| Structure | MCL-1% Bound | BCL-XL % Bound | Spec Values |
|---|---|---|---|
| 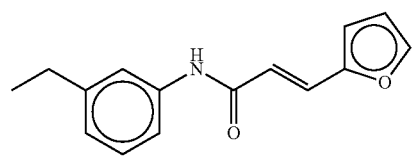 | −0.733372059 | 80.39676939 | 81.13014145 |

-continued
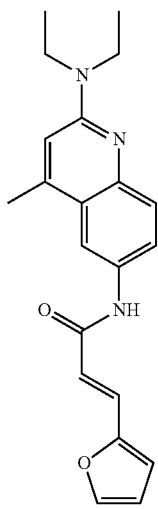 [SMILES: CCN(CC)c1cc(C)c2cc(NC(=O)/C=C/c3ccco3)ccc2n1]
11.728005051　79.877899881　68.14989482
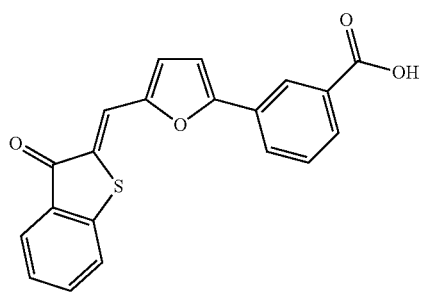 [SMILES: O=C(O)c1cccc(-c2ccc(/C=C3\Sc4ccccc4C3=O)o2)c1]
31.16639478　95.42028511　64.25389033
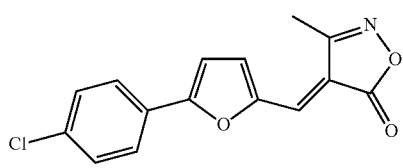 [SMILES: CC1=NOC(=O)/C1=C/c1ccc(-c2ccc(Cl)cc2)o1]
38.47471452　101.451065　65.97539199
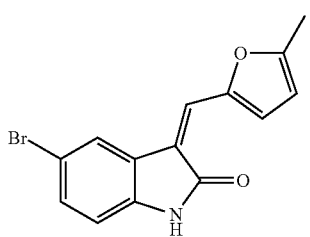 [SMILES: Cc1ccc(/C=C2\C(=O)Nc3ccc(Br)cc32)o1]
18.740375731　77.59057823　58.85020251
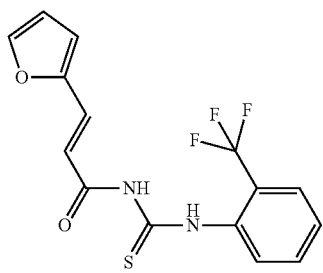 [SMILES: O=C(/C=C/c1ccco1)NC(=S)Nc1ccccc1C(F)(F)F]
47.00574838　99.25113873　52.245390351

| | | | |
|---|---|---|---|
| 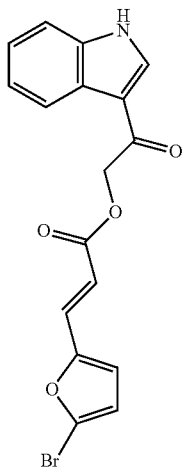 [SMILES: O=C(/C=C/c1ccc(Br)o1)OCC(=O)c1c[nH]c2ccccc12] | 53.4905597 | 105.62956951 | 52.139009761 |
| 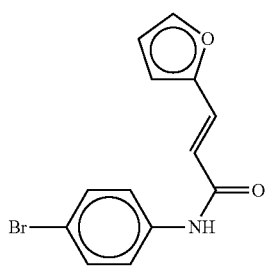 | 47.953523241 | 96.90361633 | 48.95009309 |
| 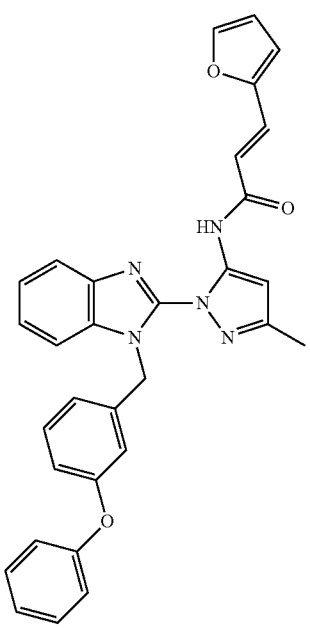 [SMILES: Cc1cc(NC(=O)/C=C/c2ccco2)n(-c2nc3ccccc3n2Cc2cccc(Oc3ccccc3)c2)n1] | 56.33127545 | 104.43159921 | 48.100323781 |
| 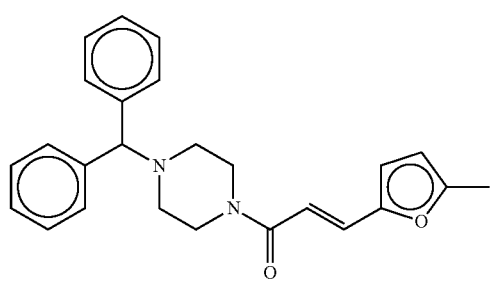 | 55.14812663 | 103.2306124 | 48.08248577 |

| | | | |
|---|---|---|---|
| 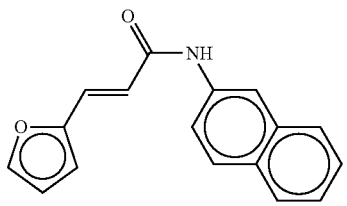 | 64.63766028 | 112.7047864 | 48.0671261 |
| 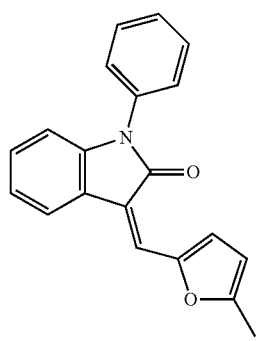 [SMILES: Cc1ccc(/C=C2\C(=O)N(c3ccccc3)c3ccccc32)o1] | 62.71844661 | 110.0825659 | 47.3641Hm: |
| 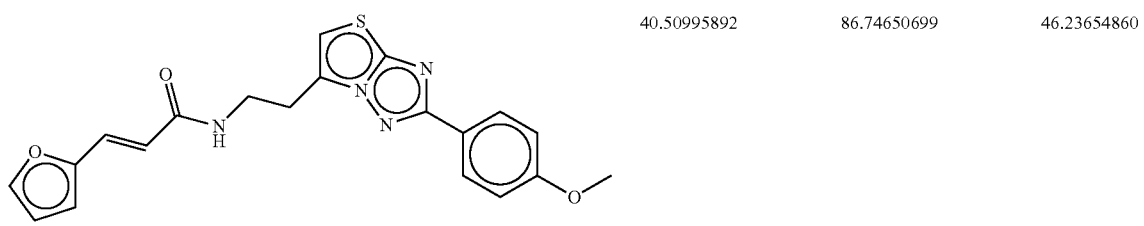 | 40.50995892 | 86.74650699 | 46.23654860 |
| 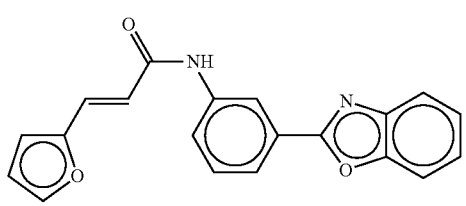 | 66.09053804 | 111.9999168 | 45.90937874 |
| 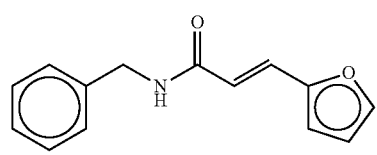 | 56.10428305 | 101.763264 | 45.65898096 |

-continued
| Structure | MCL-1% Bound | BCL-XL % Bound | Spec Values |
|---|---|---|---|
| 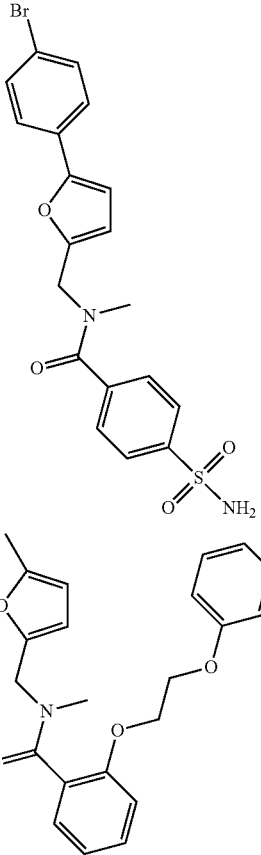 | 69.53461354 | 115.1985743 | 45.66396079 |
| 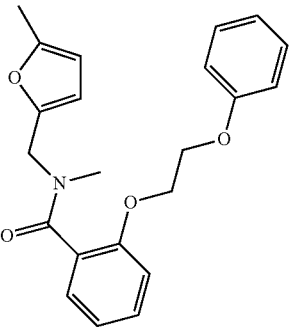 [SMILES: Cc1ccc(CN(C)C(=O)c2ccccc2OCCOc2ccccc2)o1] | 68.79611916 | 114.1804937 | 45.38437457 |
TABLE 1-F
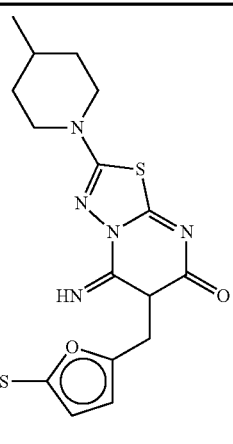
| Structure | MCL-1% Bound | BCL-XL % Bound | Spec Values |
|---|---|---|---|
| 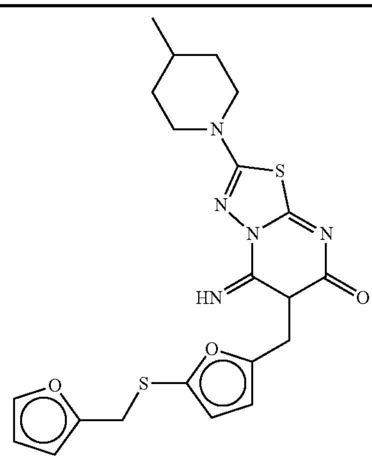 | 14.30073607 | 84.68236855 | 70.38163248 |

-continued
| Structure | MCL-1% Bound | BCL-XL % Bound | Spec Values |
|---|---|---|---|
| 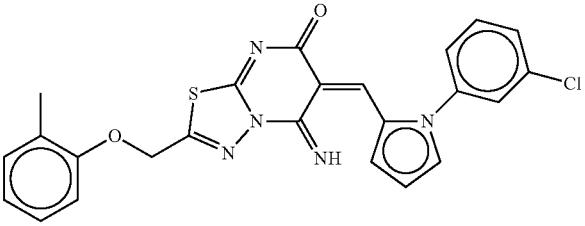 | 25.28012412 | 92.88964225 | 67.60951814 |
| 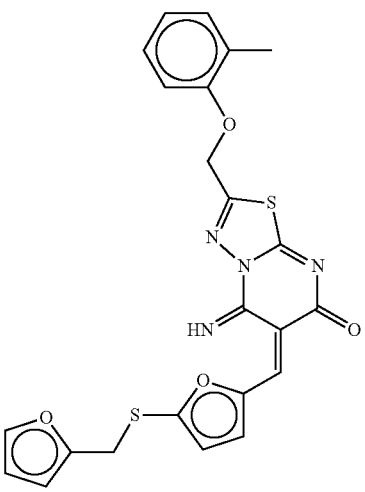 | 19.17808219 | 73.82692962 | 54.64884742 |
| 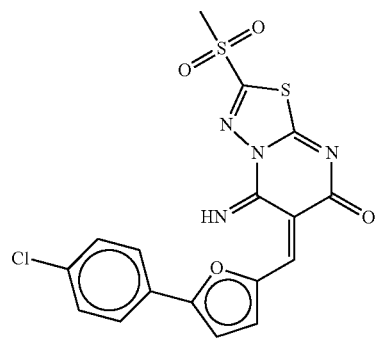 | 33.27874504 | 82.61218664 | 49.33344159 |
TABLE 1-G
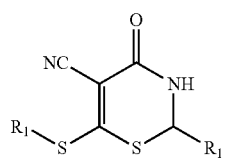
where R1 = heterocycle or aromatic
| Structure | MCL-1% Bound | BCL-XL % Bound | Spec Values |
|---|---|---|---|
| 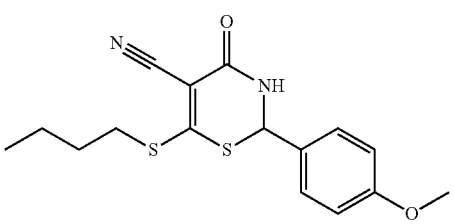 [SMILES: CCCCSC1=C(C#N)C(=O)NC(c2ccc(OC)cc2)S1] | 24.59486004 | 99.32600497 | 74.73114493 |

-continued
| Structure | | | |
|---|---|---|---|
| 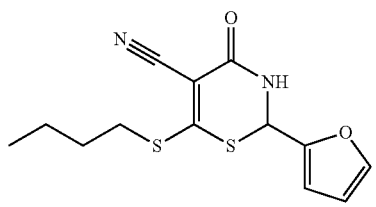 [SMILES: CCCCSC1=C(C#N)C(=O)NC(c2ccco2)S1] | 18.96382387 | 92.90700473 | 73.94318087 |
| 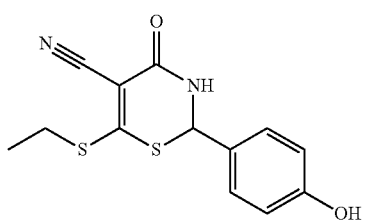 [SMILES: CCSC1=C(C#N)C(=O)NC(c2ccc(O)cc2)S1] | 15.16614831 | 84.81906443 | 69.65291612 |
| 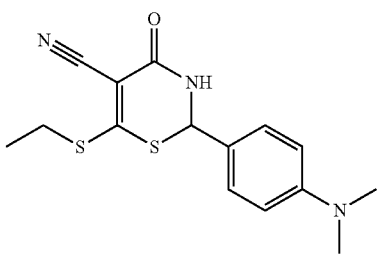 [SMILES: CCSC1=C(C#N)C(=O)NC(c2ccc(N(C)C)cc2)S1] | 30.48780488 | 79.68386424 | 49.19605936 |
TABLE 1-H
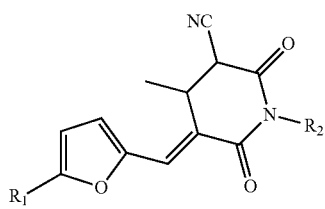
where R1 = aromatic or heterocycle
R2 = CH2
| Structure | MCL-1% Bound | BCL-XL % Bound | Spec Values |
|---|---|---|---|
| 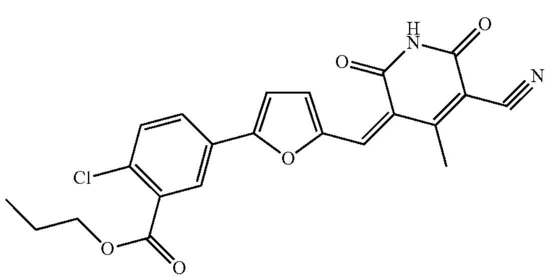 [SMILES: CCCOC(=O)c1cc(-c2ccc(/C=C3\C(=O)NC(=O)C(C#N)=C3C)o2)ccc1Cl] | −10.5954323 | 87.16205145 | 97.75748375 |

-continued
| Structure | | | |
|---|---|---|---|
| 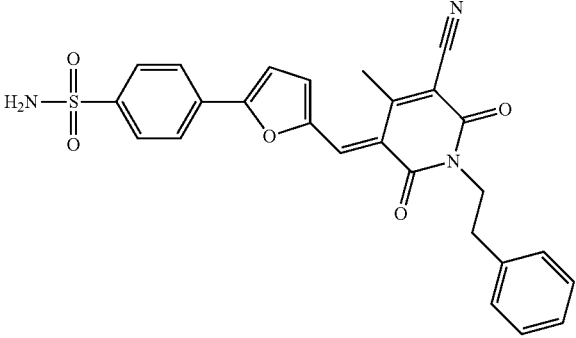 [SMILES: CC1=C(C#N)C(=O)N(CCc2ccccc2)C(=O)/C1=C/c1ccc(-c2ccc(S(N)(=O)=O)cc2)o1] | 7.037265168 | 97.35012677 | 90.3128616 |
| 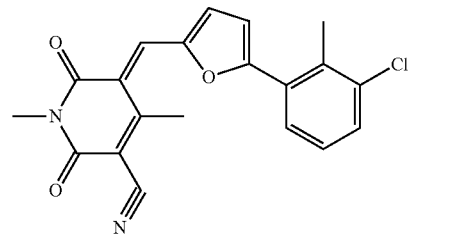 [SMILES: CC1=C(C#N)C(=O)N(C)C(=O)/C1=C/c1ccc(-c2cccc(Cl)c2C)o1] | 3.36867863 | 86.24446993 | 82.8757913 |
| 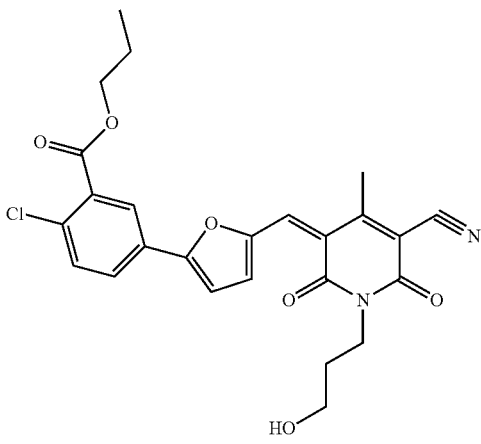 [SMILES: CCCOC(=O)c1cc(-c2ccc(/C=C3\C(=O)N(CCCO)C(=O)C(C#N)=C3C)o2)ccc1Cl] | −7.07177814 | 75.49565787 | 82.56743601 |
| 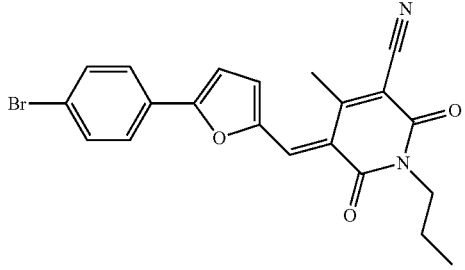 [SMILES: CCCN1C(=O)C(C#N)=C(C)/C(=C\c2ccc(-c3ccc(Br)cc3)o2)C1=O] | 20.58823529 | 102.1918705 | 81.60363516 |
| 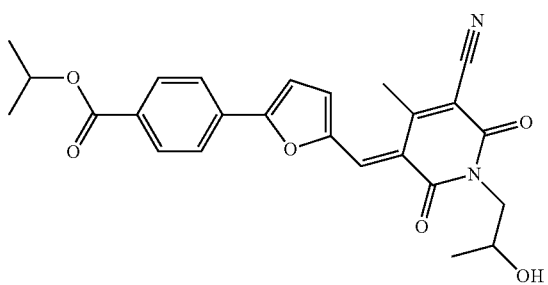 [SMILES: CC1=C(C#N)C(=O)N(CC(C)O)C(=O)/C1=C/c1ccc(-c2ccc(C(=O)OC(C)C)cc2)o1] | 30.19710502 | 107.6879038 | 77.4907988 |

-continued
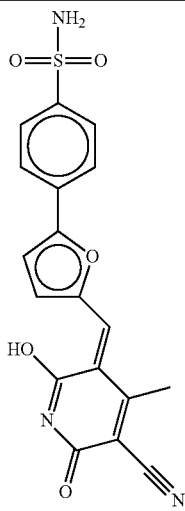	21.8	98.2	76.4
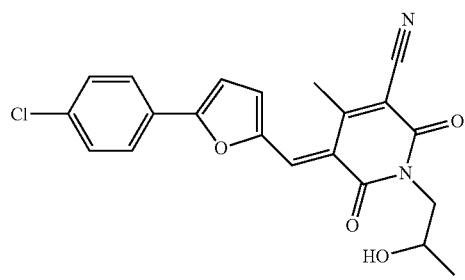 [SMILES: CC1=C(C#N)C(=O)N(CC(C)O)C(=O)/C1=C/c1ccc(-c2ccc(Cl)cc2)o1]	15.04465661	89.36779259	74.32313598
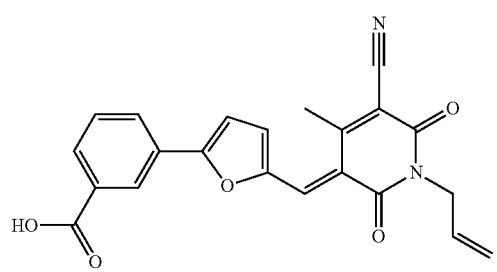 [SMILES: C=CCN1C(=O)C(C#N)=C(C)/C(=C\c2ccc(-c3cccc(C(=O)O)c3)o2)C1=O]	31.4290114	89.23693465	57.80792326
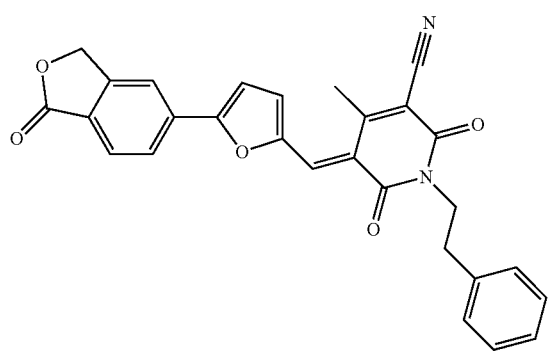 [SMILES: CC1=C(C#N)C(=O)N(CCc2ccccc2)C(=O)/C1=C/c1ccc(-c2ccc3c(c2)COC3=O)o1]	30.81305821	84.78776478	53.97470658

-continued
| Structure | | | |
|---|---|---|---|
| 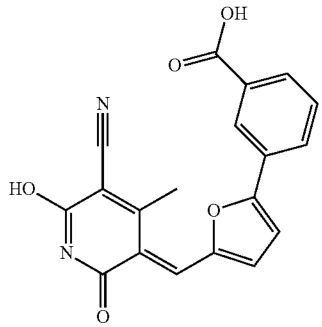 [SMILES: CC1=C(C#N)C(O)=NC(=O)/C1=C/c1ccc(-c2cccc(C(=O)O)c2)o1] | 36.80576864 | 89.70132202 | 52.89555338 |
| 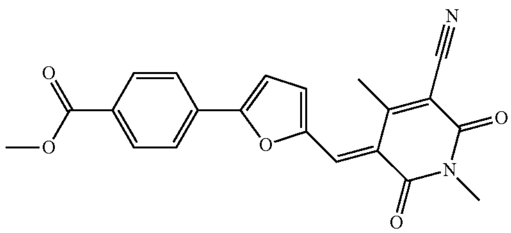 [SMILES: COC(=O)c1ccc(-c2ccc(/C=C3/C(=O)N(C)C(=O)C(C#N)=C3C)o2)cc1] | 38.82044965 | 91.59237753 | 52.77192788 |
| 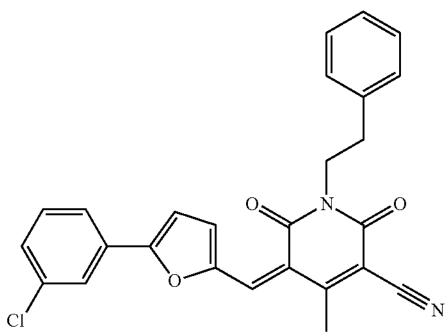 [SMILES: CC1=C(C#N)C(=O)N(CCc2ccccc2)C(=O)/C1=C\c1ccc(-c2cccc(Cl)c2)o1] | 29.33477056 | 78.76829966 | 49.43352911 |
TABLE 1-I
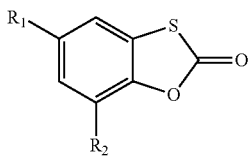
where R1 = H or sulfonamide-, ester-,
or amide linked heterocycle or aromatic
R2 = H or aromatic
| Structure | MCL-1% Bound | BCL-XL % Bound | Spec Values |
|---|---|---|---|
| 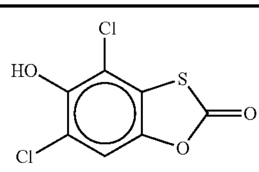 | −5.219264716 | 104.6841563 | 109.903421 |
| 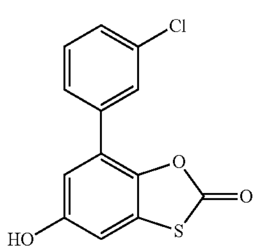 [SMILES: O=c1oc2c(-c3cccc(Cl)c3)cc(O)cc2s1] | 11.19902121 | 76.15107324 | 64.95205204 |

-continued

| Structure | MCL-1% Bound | BCL-XL % Bound | Spec Values |
|---|---|---|---|
| (2,5-dimethylphenyl sulfonamide chlorobenzoxathiol-2-one) | 25.38058602 | 86.7447645 | 61.36417848 |
| (3-methylbenzoate benzoxathiol-2-one) | 44.3557943 | 92.23836973 | 47.88257544 |

TABLE 1-J

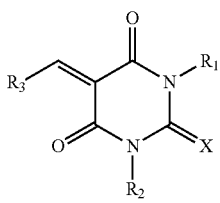

where X = S or O
R3 = aromatic or heterocycle

| Structure | MCL-1% Bound | BCL-XL % Bound | Spec Values |
|---|---|---|---|
| (4-methoxybenzylidene-allyl-thiobarbiturate) | 19.08127208 | 95.08543531 | 76.00416323 |
| (cyclohexenylethyl-phenylpyrimidinyl-methylidene barbiturate) | 43.51306119 | 106.9095962 | 63.39656504; |
| (iodo-hydroxybenzylidene-diethyl-thiobarbiturate) | 39.32183657 | 100.3628503 | 61.041013731 |

-continued
| | | | |
|---|---|---|---|
| 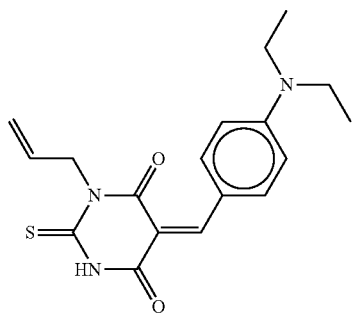 | 41.8167411 | 102.1683264 | 60.35158527 |
| 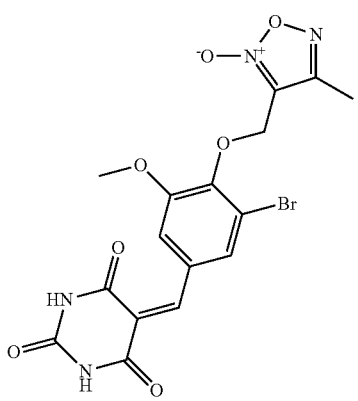 | 38.17542436 | 95.91685226 | 57.74142791 |
| 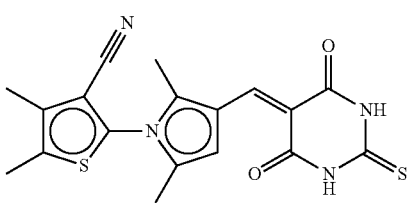 | 45.19897498 | 102.0166733 | 56.81769831 |
| 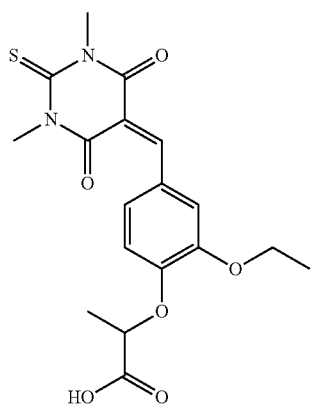 [SMILES: CCOc1cc(C=C2C(=O)N(C)C(=S)N(C)C2=O)ccc1OC(C)C(=O)O] | 41.985733 | 98.20470972 | 56.21897672 |
| 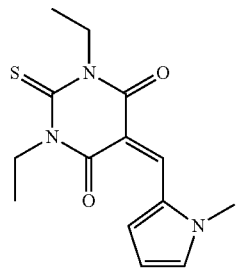 [SMILES: CCN1C(=O)C(=Cc2cccn2C)C(=O)N(CC)C1=S] | 52.01193335 | 105.6743612 | 53.6624278 |

| | | | |
|---|---|---|---|
| 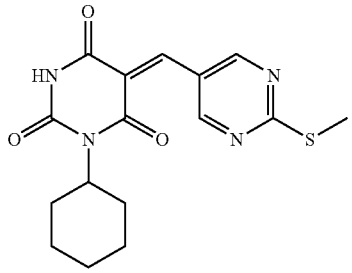 [SMILES: CSc1ncc(/C=C2/C(=O)NC(=O)N(C3CCCCC3)C2=O)cn1] | 46.42363385 | 99.004091721 | 52.58045787 |
| 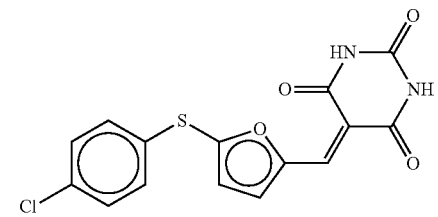 | 39.96352925 | 92.21643287 | 52.25290362 |
| 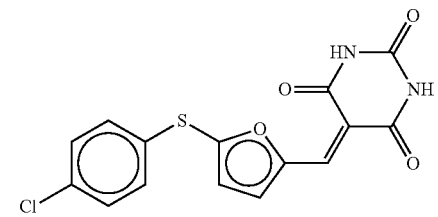 | 30.59011861 | 81.34023006 | 50.75011146 |
| 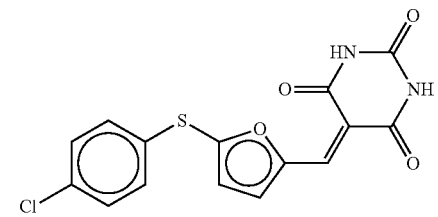 | 33.00999412 | 82.65729799 | 49.64730387 |
| 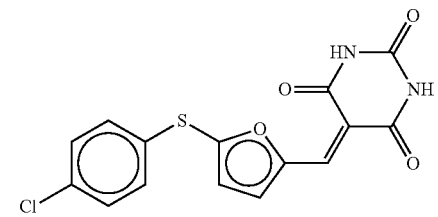 | 51.18862475 | 99.22340759 | 48.03478284 |

-continued
| Structure | | | |
|---|---|---|---|
| 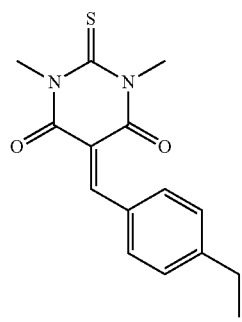 [SMILES: CCc1ccc(C=C2C(=O)N(C)C(=S)N(C)C2=O)cc1] | 55.45434348 | 100.8550361 | 45.4006926 |
TABLE 1-K
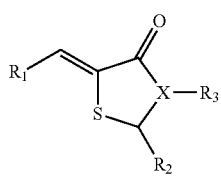
where R1 = phenyl or furan
X = N or C
| Structure | MCL-1% Bound | BCL-XL % Bound | Spec Values |
|---|---|---|---|
| 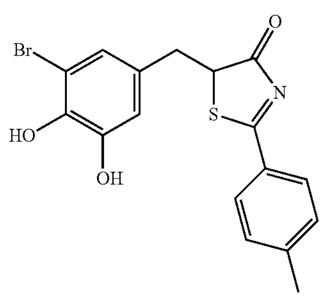 [SMILES: Cc1ccc(C2=NC(=O)C(Cc3cc(O)c(O)c(Br)c3)S2)cc1] | 2.606828112 | 96.58770003 | 93.98087192 |
| 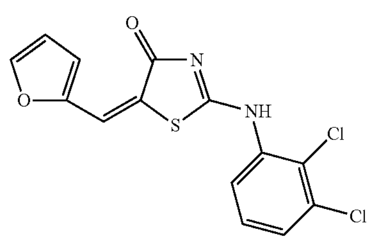 [SMILES: O=C1N=C(Nc2cccc(Cl)c2Cl)S/C1=C/c1ccco1] | 15.57226143 | 89.44018281 | 73.86792137 |
| 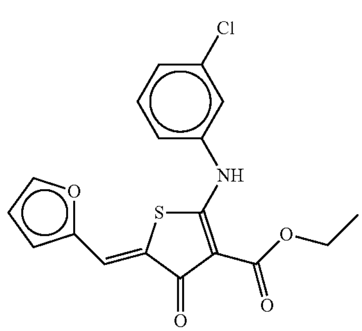 | 48.21516581 | 111.214653 | 62.99948715 |

-continued
| | | | |
|---|---|---|---|
| 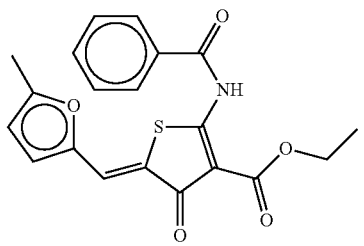 | 43.16379248 | 101.2275149 | 58.06372239 |
| 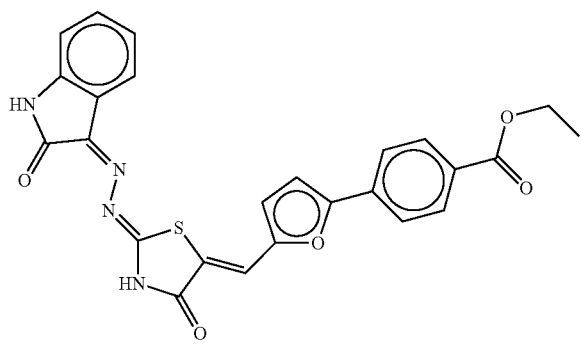 | 13.28219273 | 66.62503346 | 53.34284073 |
| 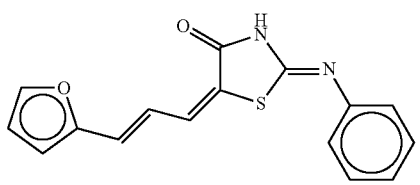 | 48.95344507 | 97.58836088 | 48.63491581 |
| 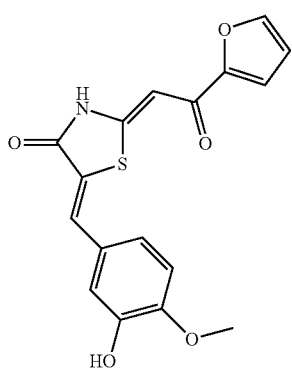 [SMILES: COc1ccc(/C=c2\s/c(=C\C(=O)c3ccco3)[nH]c2=O)cc1O] | 215.6015433 | 263.737406 | 48.13586273 |
| 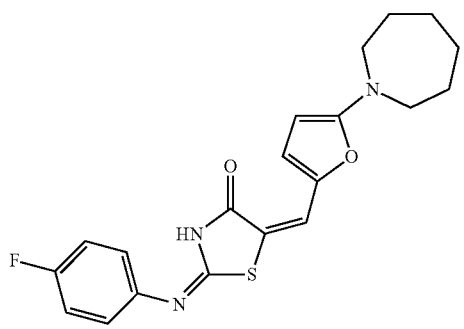 [SMILES: O=C1N/C(=N\c2ccc(F)cc2)S/C1=C/c1ccc(N2CCCCCC2)o1] | 40.42192793 | 87.79749734 | 47.37556941 |

TABLE 1-L
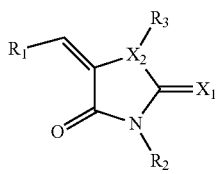
where X1 = O or S
X2 = S or N
| Structure | MCL-1% Bound | BCL-XL % Bound | Spec Values |
|---|---|---|---|
| 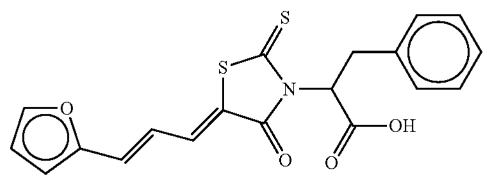 | −9.610778443 | 87.82745228/ | 97.43823072! |
| 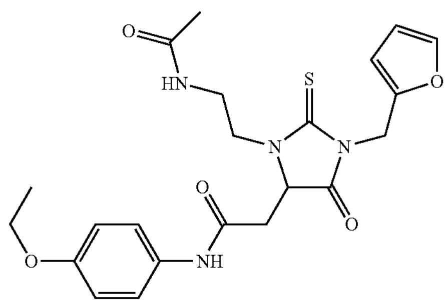 [SMILES: CCOc1ccc(NC(=O)CC2C(=O)N(Cc3ccco3)C(=S)N2CCNC(C)=O)cc1] | 19.68883273 | 102.4094424 | 82.72060968 |
| 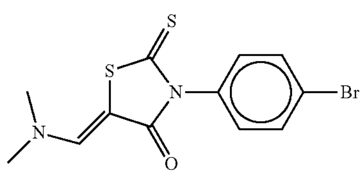 | 33.27029276 | 112.3457833 | 79.07549058 |
| 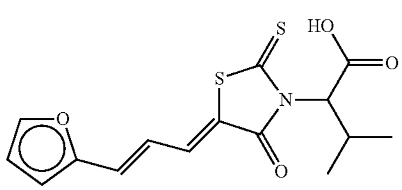 | 26.07784431 | 102.7683663; | 76.69052194 |
| 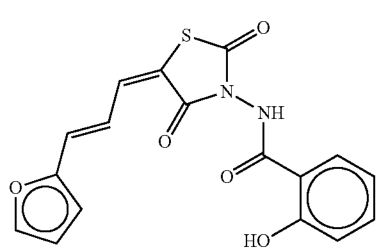 | 19.8 | 95.8 | 76.1 |

-continued
| | | | |
|---|---|---|---|
| 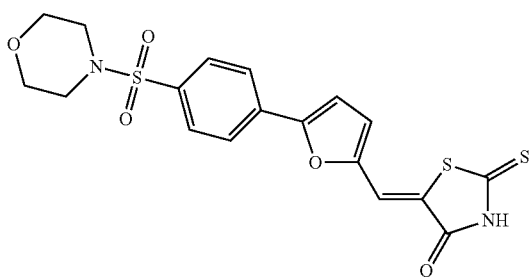 | 38.57217917 | 107.8998073 | 69.32762815 |
| 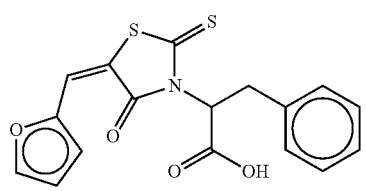 | 21.28742515 | 90.20742087 | 68.91999572 |
| 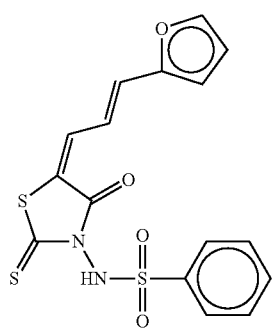 | 23.0 | 89.9 | 66.9 |
| 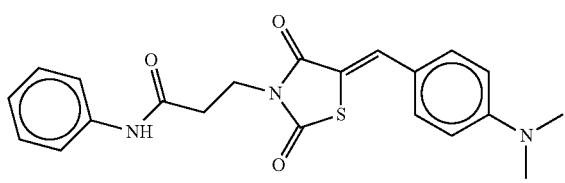 | 29.45492662 | 92.21556886 | 62.76064224 |
| 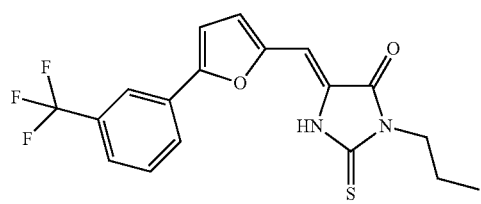 [SMILES: CCCN1C(=O)/C(=C/c2ccc(-c3cccc(C(F)(F)F)c3)o2)NC1=S] | 27.92957859 | 85.64814815 | 57.71856956 |
| 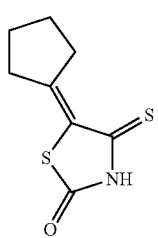 [SMILES: O=C1NC(=S)C(=C2CCCC2)S1] | 38.04746419 | 93.34466638 | 55.29720219 |

-continued
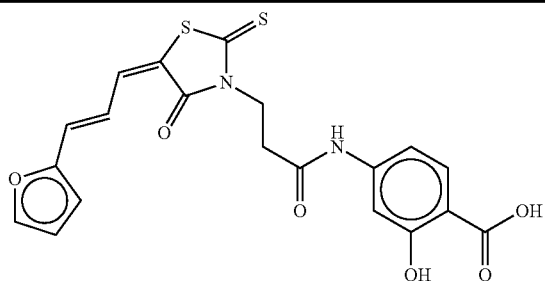 | 21.54074074 | 76.08572124 | 54.54498051
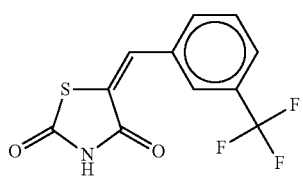 | 42.5929832 | 94.16497422 | 51.57199103
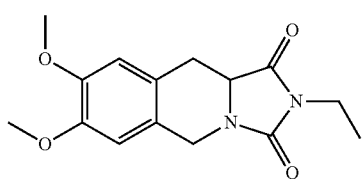 [SMILES: CCN1C(=O)C2Cc3cc(OC)c(OC)cc3CN2C1=O] | 39.83535868 | 91.73339804 | 51.89803936
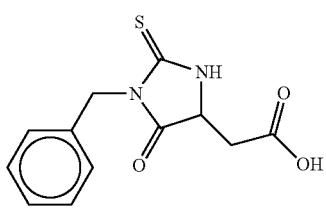 | 48.7076967' | 98.89474361 | 50.1870469
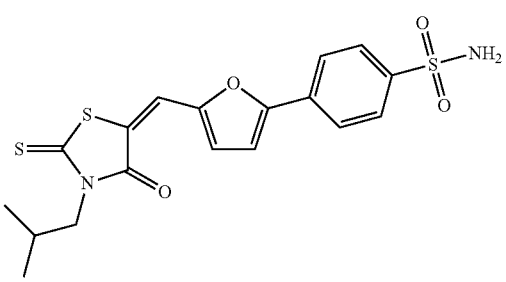 [SMILES: CC(C)CN1C(=O)/C(=C\c2ccc(-c3ccc(S(N)(=O)=O)cc3)o2)SC1=S] | 58.50862999 | 105.8574397 | 47.34880968

TABLE 1-M
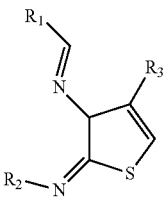
where R1 = aromatic or heterocycle
| Structure | MCL-1% Bound | BCL-XL % Bound | Spec Values |
|---|---|---|---|
| (structure) | −23.10049446 | 101.7468716 | 124.8473661 |
| (structure) | −16.27483907 | 89.94614004 | 106.2209791 |
TABLE 1-N
| Structure | MCL-1% Bound | BCL-XL % Bound | Spec Values |
|---|---|---|---|
| (structure) | −65.83063646 | 102.6892674 | 168.5199038 |
| (structure) | −6.59173964 | 129.3090909 | 135.9008305 |

| | | | |
|---|---|---|---|
| 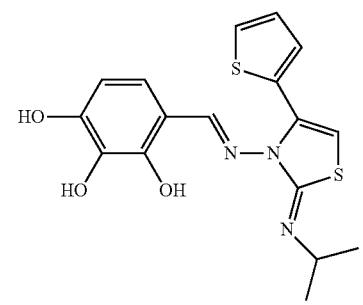 [SMILES: CC(C)/N=c1\scc(-c2cccs2)n1/N=C/c1ccc(O)c(O)c1O] | −23.10049446 | 101.7468716 | 124.8473661 |
| 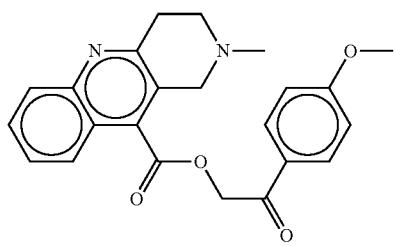 | −30.96202705 | 88.78573776 | 119.7477648 |
| 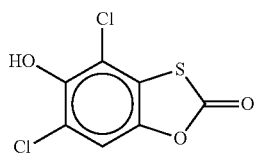 | −5.219264716 | 104.6841563 | 109.903421 |
| 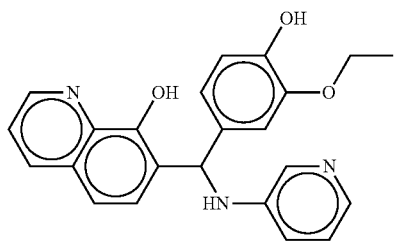 | −0.3 | 108.4 | 108.7 |
| 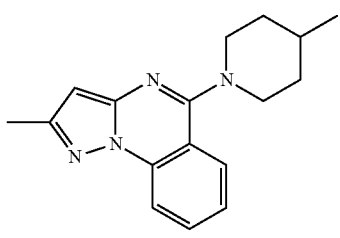 | −1.785938876 | 106.6729323 | 108.4588712 |
| 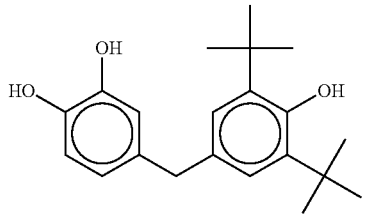 | −11.55743971 | 96.56812237 | 108.1255621 |

-continued
| | | | |
|---|---|---|---|
| 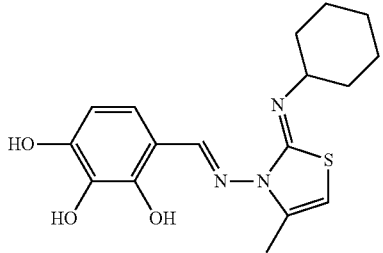 [SMILES: Cc1cs/c(=N\C2CCCCC2)n1/N=C/c1ccc(O)c(O)c1O] | −16.27483907 | 89.94614004 | 106.2209791 |
| 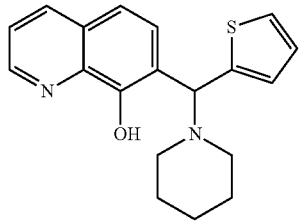 [SMILES: Oc1c(C(c2cccs2)N2CCCCC2)ccc2cccnc12] | 9.463295931 | 115.1848233 | 105.7215274 |
| 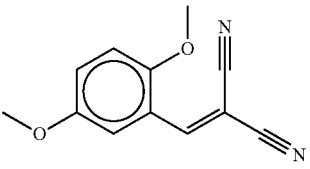 | −7.035327937 | 98.55501099 | 105.5903389 |
| 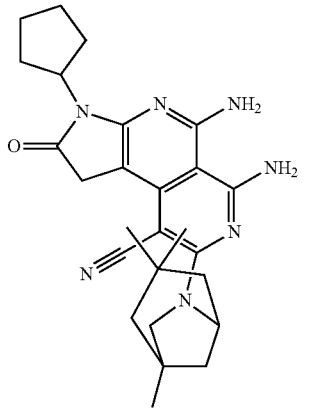 | 10.7155014 | 114.7223418 | 104.0068404 |
| 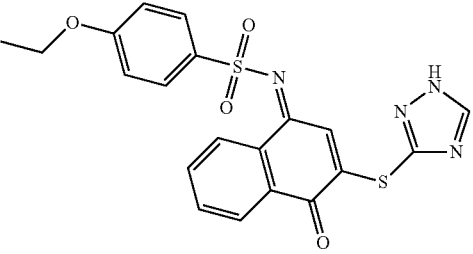 [SMILES: CCOc1ccc(S(=O)(=O)/N=C2/C=C(Sc3nc[nH]n3)C(=O)c3ccccc32)cc1] | 2.332623997' | 103.4341651 | 101.1015411 |
| 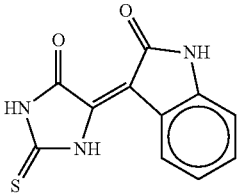 | 14.04124001 | 112.8657315 | 98.82449146 |

-continued
| | | | |
|---|---|---|---|
| 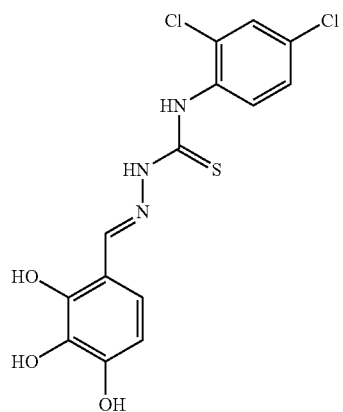 [SMILES: Oc1ccc(/C=N/NC(=S)Nc2ccc(Cl)cc2Cl)c(O)c1O] | −10.8685997 | 87.36357022 | 98.23216992 |
| 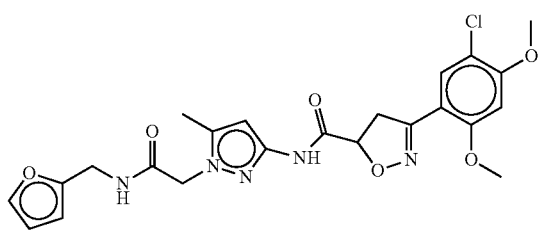 | −14.50299142 | 83.61559031 | 98.11858173 |
| 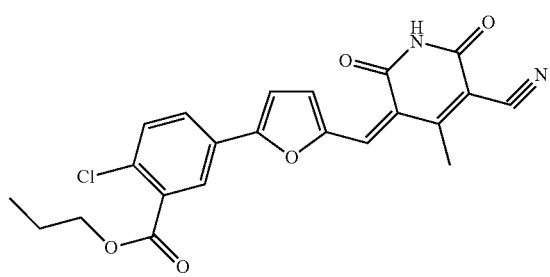 [SMILES: CCCOC(=O)c1cc(-c2ccc(/C=C3\C(=O)NC(=O)C(C#N)=C3C)o2)ccc1Cl] | −10.5954323 | 87.16205145 | 97.75748375 |
| 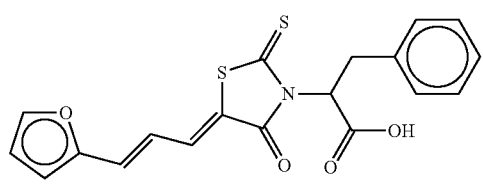 | −9.610778443 | 87.82745228 | 97.43823072 |
| 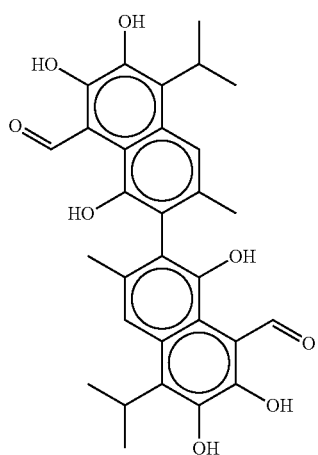 | 3.955080904 | 101.0243434 | 97.0692625 |

-continued
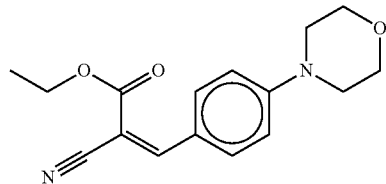 | −18.5 | 78.1! | 96.6
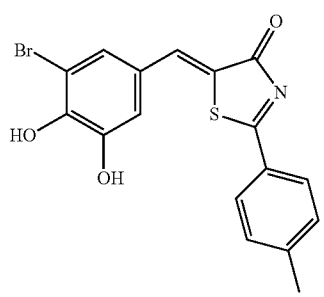 [SMILES: Cc1ccc(C2=NC(=O)/C(=C/c3cc(O)c(O)c(Br)c3)S2)cc1] | 2.606828112 | 96/58770003 | 93.98087192
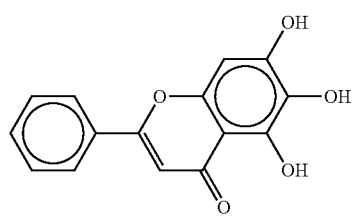 | 10.32290702 | 104.1661092 | 93.84320213
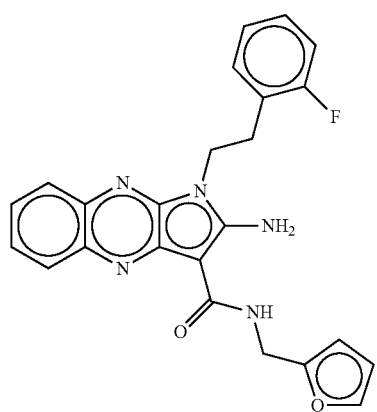 | 6.6 | 99.9 | 93.2
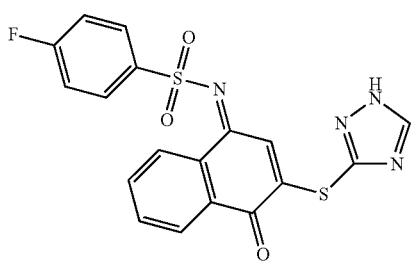 [SMILES: O=C1C(Sc2nc[nH]n2)=C/C(=N/S(=O)(=O)c2ccc(F)cc2)c2ccccc21] | 4.951710591 | 96.11650485 | 91.16479426

| | | | |
|---|---|---|---|
| 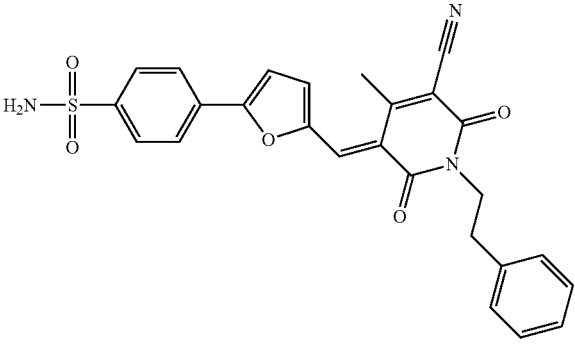 [SMILES: CC1=C(C#N)C(=O)N(CCc2ccccc2)C(=O)/C1=C/c1ccc(-c2ccc(S(N)(=O)=O)cc2)o1] | 7.037265168 | 97.35012677 | 90.3128616 |
| 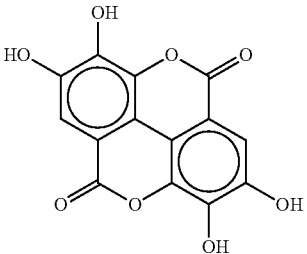 | 1.259544221 | 90.57802572 | 89.3184815 |
| 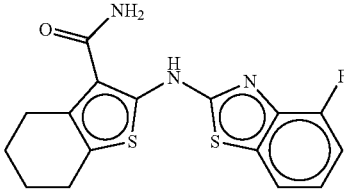 | 14.82516366 | 103.9217319 | 89.09656823 |
| 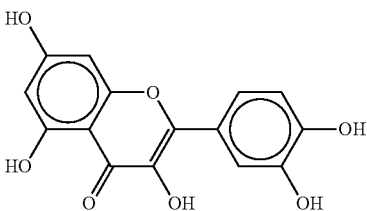 | 16.68871081 | 105.3416001 | 88.65288929 |
| 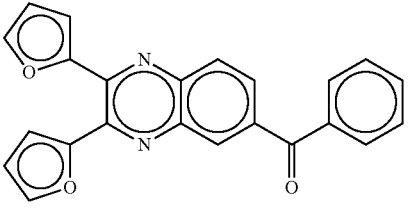 | 14.6 | 101.3 | 86.7 |
| 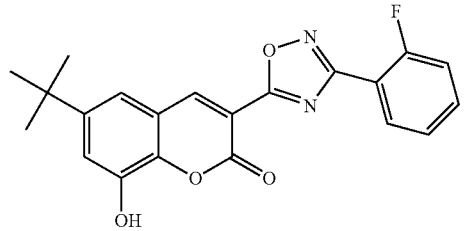 [SMILES: CC(C)(C)c1cc(O)c2oc(=O)c(-c3nc(-c4ccccc4F)no3)cc2c1] | −13.00667806 | 71.10363607 | 84.11031413 |

-continued
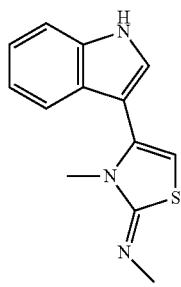 [SMILES: C/N=c1\scc(-c2c[nH]c3ccccc23)n1C]  30.17353579  114.1379598  83.964424
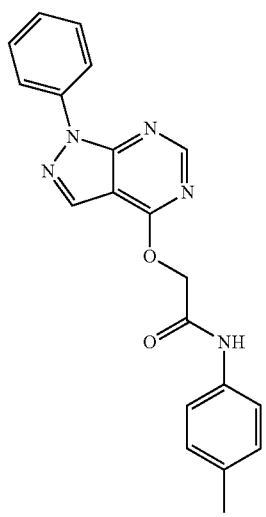 [SMILES: Cc1ccc(NC(=O)COc2ncnc3c2cnn3-c2ccccc2)cc1]  16.19966207  99.90532748  83.70566541
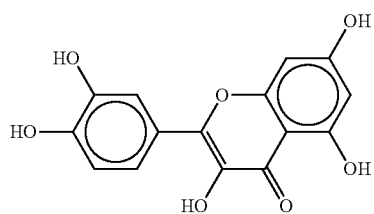  9.240186268  92.49338093  83.25319466
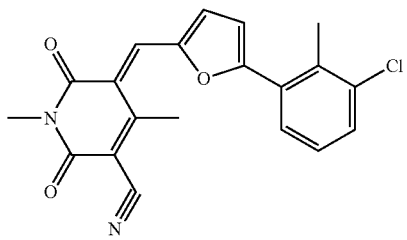 [SMILES: CC1=C(C#N)C(=O)N(C)C(=O)/C1=C/c1ccc(-c2cccc(Cl)c2C)o1]  3.36867863  86.24446993  82.8757913
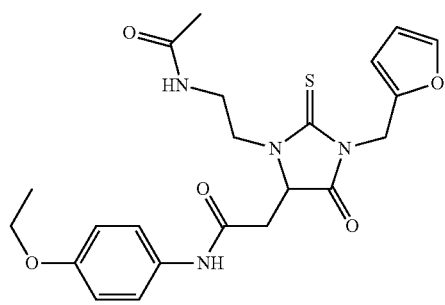 [SMILES: CCOc1ccc(NC(=O)CC2C(=O)N(Cc3ccco3)C(=S)N2CCNC(C)=O)cc1]  19.68883273  102.4094424  82.72060968

-continued
| | | | |
|---|---|---|---|
| 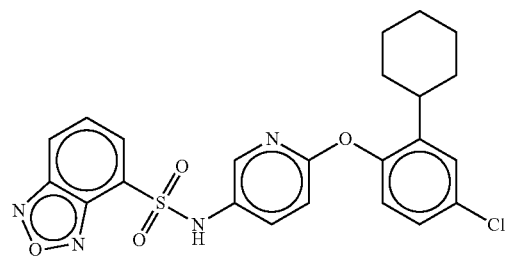 | 20.72333282 | 103.4206261 | 82.69729329 |
| 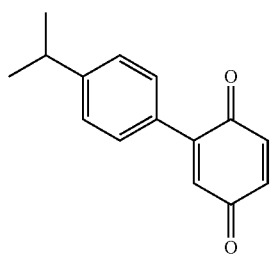 [SMILES: CC(C)c1ccc(C2=CC(=O)C=CC2=O)cc1] | 6.516370589 | 89.09642401 | 82.58005342 |
| 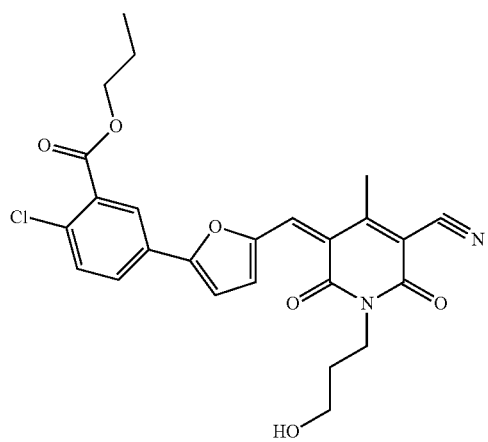 [SMILES: CCCOC(=O)c1cc(-c2ccc(/C=C3\C(=O)N(CCCO)C(=O)C(C#N)=C3C)o2)ccc1Cl] | −7.07177814 | 75.49565787 | 82.56743601 |
| 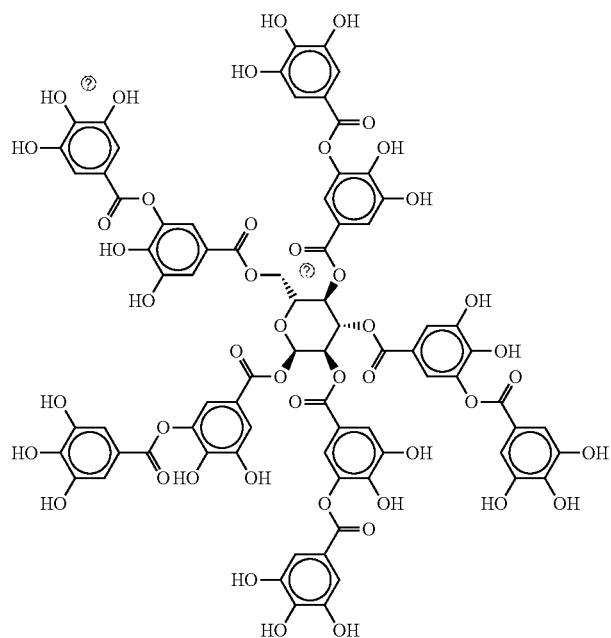 | 15.93536133 | 98.2573418 | 82.32198048 |

-continued
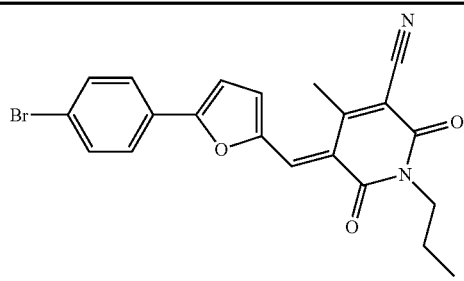
| | | |
|---|---|---|
| 20.58823529 | 102.1918705 | 81.60363516 |
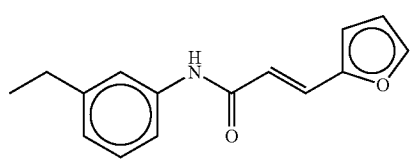
| | | |
|---|---|---|
| −0.733372059 | 80.39676939 | 81.13014145 |
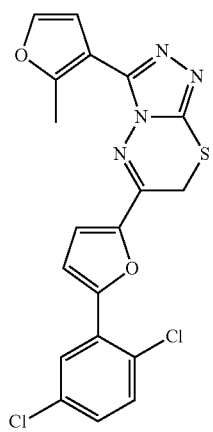 [SMILES: Cc1occc1-c1nnc2n1N=C(c1ccc(-c3cc(Cl)ccc3Cl)o1)CS2]
| | | |
|---|---|---|
| 22.9770388 | 104.006981 | 81.02905928 |
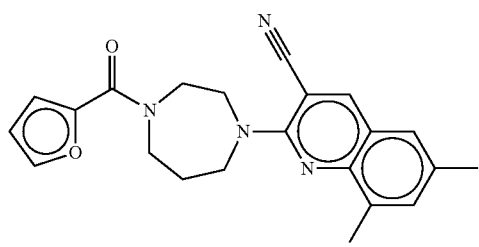
| | | |
|---|---|---|
| 11.4 | 92.2 | 80.8 |
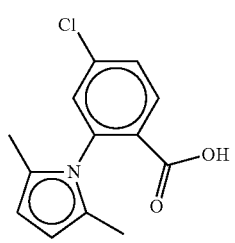
| | | |
|---|---|---|
| −3.913592369 | 75.92785571 | 79.841448081 |

-continued
| Structure | | | |
|---|---|---|---|
| 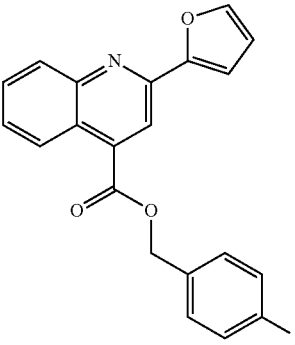 | 21.93834459 | 101.5900478 | 79.65170319 |
| 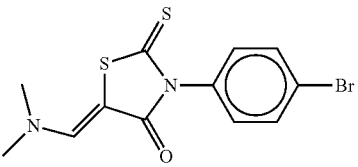 | 33.27029276 | 112.3457833 | 79.07549058 |
| 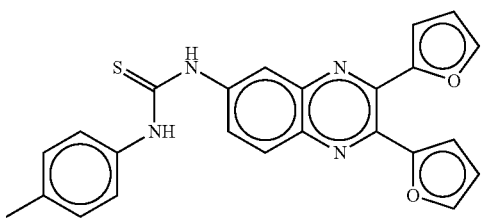 | −2.04714193 | 75.96629122 | 78.01343315 |
| 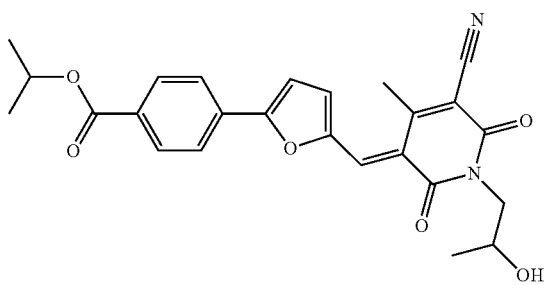 [SMILES: CC1=C(C#N)C(=O)N(CC(C)O)C(=O)/C1=C/c1ccc(-c2ccc(C(=O)OC(C)C)cc2)o1] | 30.19710502 | 107.6879038 | 77.4907988 |
| 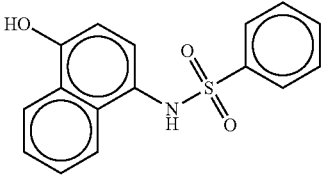 | 19.67020024 | 96.38730675 | 76.71710652 |
| 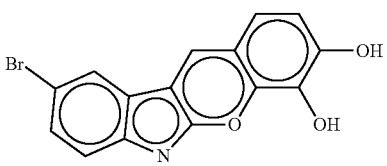 | 13.3744856 | 90.06707122 | 76.69258563 |
| 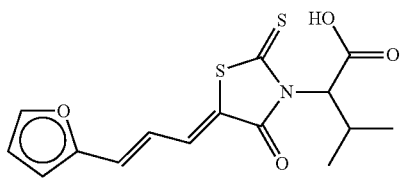 | 26.07784431 | 102.7683663 | 76.69052194 |

-continued
| | | | |
|---|---|---|---|
| 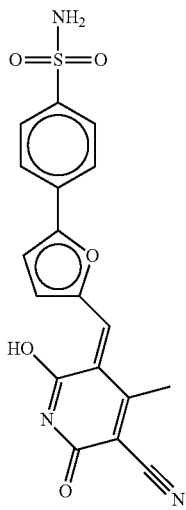 | 21.8 | 98.2 | 76.4 |
| 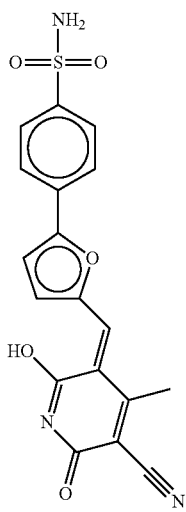 | 17.4 | 93.7 | 76.4 |
| 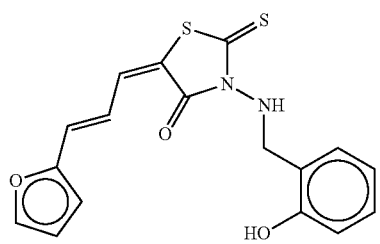 | 19.8 | 95.8 | 76.1 |
| 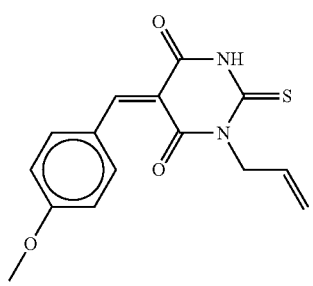 | 19.08127208 | 95.08543531 | 76.00416323 |

-continued
| | | | |
|---|---|---|---|
| 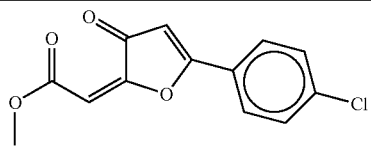 | 21.79034158 | 97.16842962 | 75.37808804 |
| 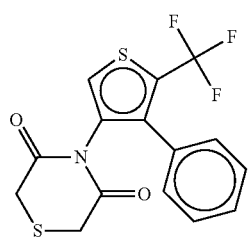 | 21.55274889 | 96.34785598 | 74.79510709 |
| 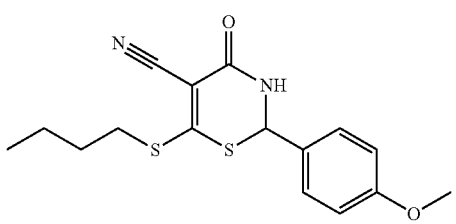 [SMILES: CCCCSC1=C(C#N)C(=O)NC(c2ccc(OC)cc2)S1] | 24.59486004 | 99.32600497 | 74.73114493 |
| 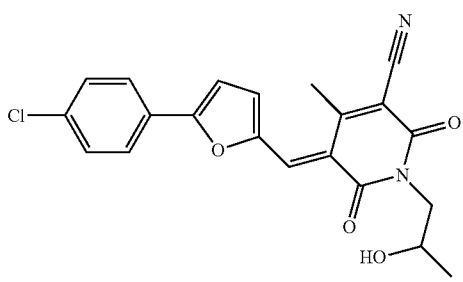 [SMILES: CC1=C(C#N)C(=O)N(CC(C)O)C(=O)/C1=C/c1ccc(-c2ccc(Cl)cc2)o1] | 15.04465661 | 89.36779259 | 74.32313598 |
| 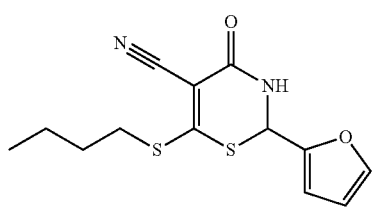 [SMILES: CCCCSC1=C(C#N)C(=O)NC(c2ccco2)S1] | 18.96382387 | 92.90700473 | 73.94318087 |
| 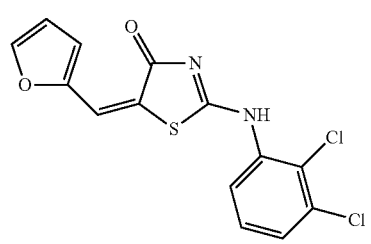 [SMILES: O=C1N=C(Nc2cccc(Cl)c2Cl)S/C1=C/c1ccco1] | 15.57226143 | 89.4401828 | 73.86792137 |

| | | | |
|---|---|---|---|
| 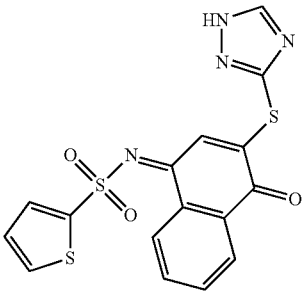 [SMILES: O=C1C(Sc2nc[nH]n2)=C/C(=N/S(=O)(=O)c2cccs2)c2ccccc21] | 19.74954984 | 93.6376474 | 73.4142149 |
| 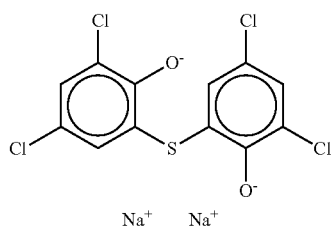 | 27.20036677 | 100.4228001 | 73.22243335 |
| 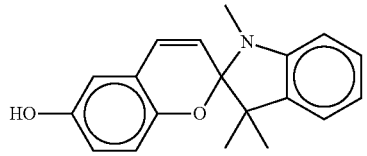 | 37.92480367 | 111.0248078 | 73.10000413 |
| 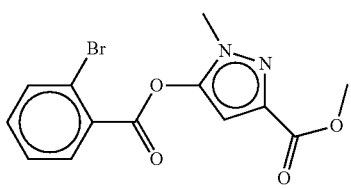 | 30.22510381 | 103.1419548 | 72.916851 |
| 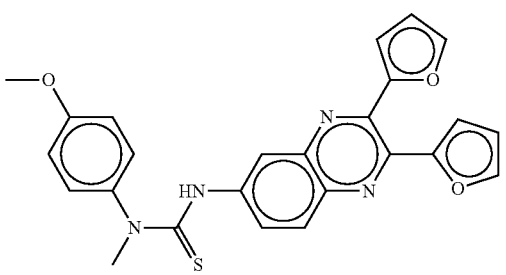 | 8.322108744 | 81.17127433 | 72.83916559 |
| 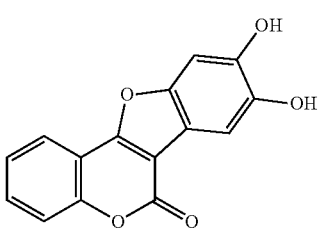 [SMILES: O=c1oc2ccccc2c2oc3cc(O)c(O)cc3c12] | 12.58907363 | 84.89878885 | 72.30971522 |

-continued
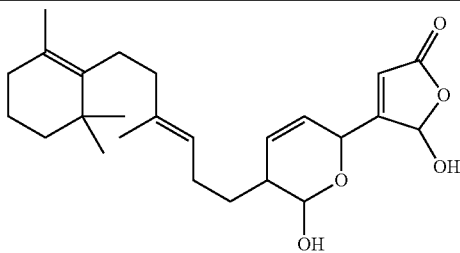
| | | |
|---|---|---|
| 35.01128141 | 106.8345939 | 71.8233125 |
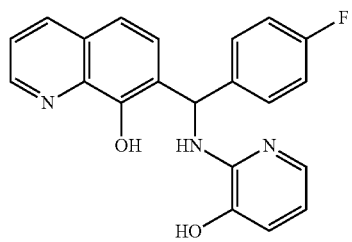 [SMILES: Oc1cccnc1NC(c1ccc(F)cc1)c1ccc2cccnc2c1O]
| | | |
|---|---|---|
| 42.48636709 | 113.7228826 | 71.236515471 |
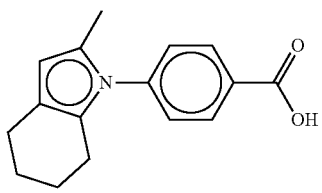
| | | |
|---|---|---|
| −5.849688118 | 65.32554791 | 71.17523603 |
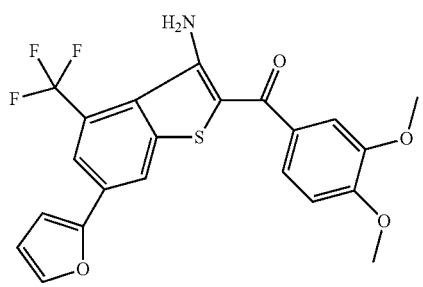 [SMILES: COc1ccc(C(=O)c2sc3cc(-c4ccco4)cc(C(F)(F)F)c3c2N)cc1OC]
| | | |
|---|---|---|
| 14.29140445 | 85.26500639 | 70.97360194 |
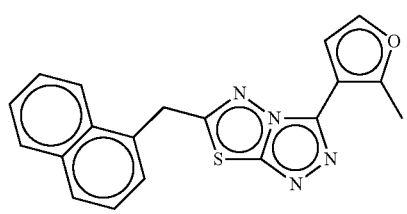
| | | |
|---|---|---|
| 58.7 | 129.5 | 70.8 |
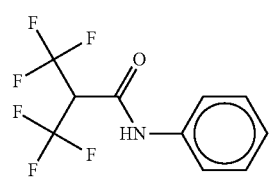
| | | |
|---|---|---|
| 11.97648788 | 82.61082938 | 70.6343415, |

-continued
| | | | |
|---|---|---|---|
| 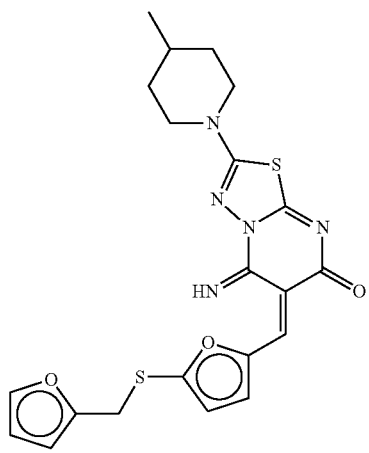 | 14.30073607 | 84.68236855 | 70.381632481 |
| 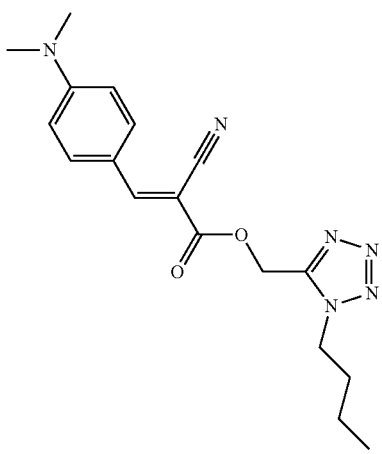 [SMILES: CCCCn1nnnc1COC(=O)/C(C#N)=C/c1ccc(N(C)C)cc1] | −7.305502846 | 62.96737927 | 70.27288212 |
| 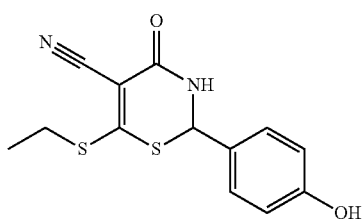 [SMILES: CCSC1=C(C#N)C(=O)NC(c2ccc(O)cc2)S1] | 15.16614831 | 84.8190644 | 69.65291612 |
| 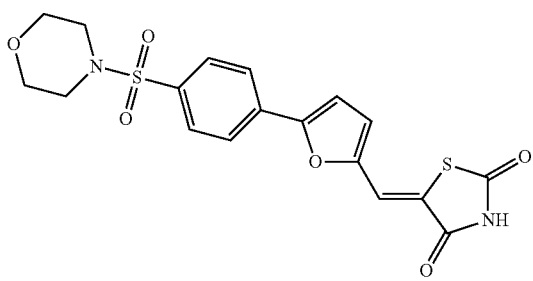 [SMILES: O=C1NC(=O)/C(=C/c2ccc(-c3ccc(S(=O)(=O)N4CCOCC4)cc3)o2)S1] | 38.57217917 | 107.8998073 | 69.32762815 |
| 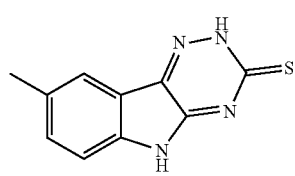 | 38.64682418 | 107.8504978 | 69.20367362 |

-continued
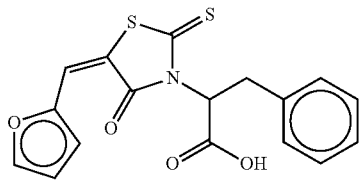
| | | |
|---|---|---|
| 21.28742515 | 90.20742087 | 68.91999572 |
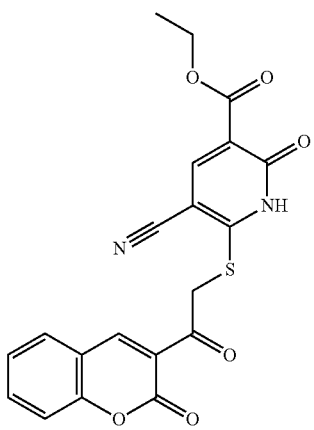 [SMILES: CCOC(=O)c1cc(C#N)c(SCC(=O)c2cc3ccccc3oc2=O)[nH]c1=O]
| | | |
|---|---|---|
| 31.28187691 | 100.1843318 | 68.90245488 |
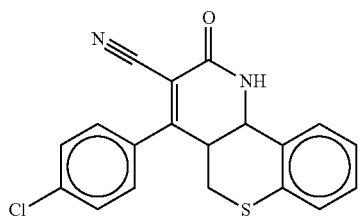
| | | |
|---|---|---|
| 19.37221111 | 87.66541823 | 68.29320712 |
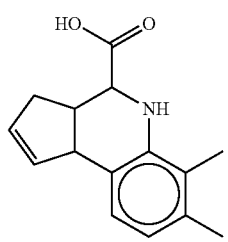
| | | |
|---|---|---|
| 14.5 | 82.8 | 68.3 |
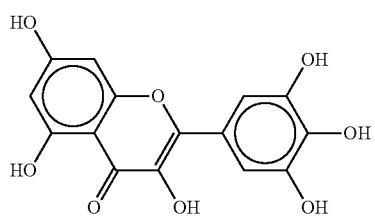
| | | |
|---|---|---|
| 34.13126397 | 102.3629331 | 68.23166909 |

-continued
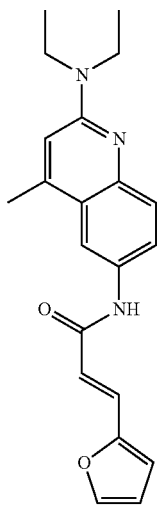 [SMILES: CCN(CC)c1cc(C)c2cc(NC(=O)/C=C/c3ccco3)ccc2n1]
| | | |
|---|---|---|
| 11.72800505 | 79.87789988 | 68.14989482 |
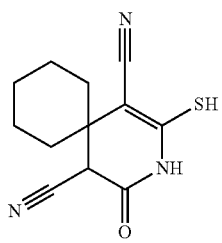 [SMILES: N#CC1=C(S)NC(=O)C(C#N)C12CCCCC2]
| | | |
|---|---|---|
| 39.1 | 107.0 | 67.9 |
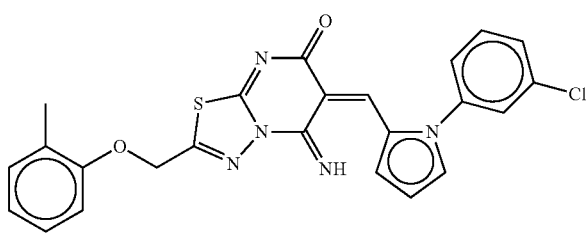
| | | |
|---|---|---|
| 25.28012412 | 92.88964225 | 67.60951814 |
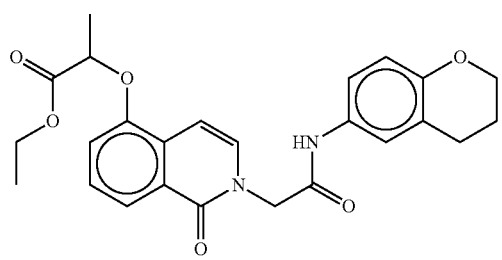
| | | |
|---|---|---|
| 34.53258845 | 102.0162884 | 67.48369999 |
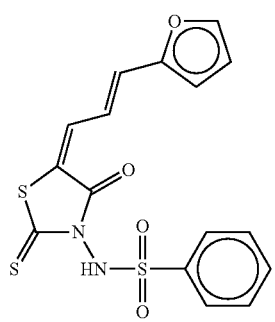
| | | |
|---|---|---|
| 23.0 | 89.9 | 66.9 |

-continued
| | | | |
|---|---|---|---|
| 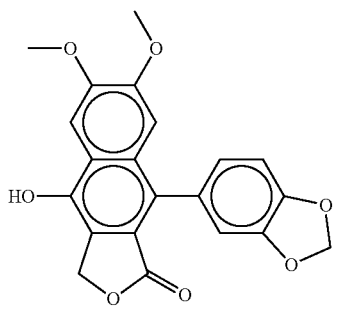 | 37.92480367 | 104.5573433 | 66.6325396 |
| 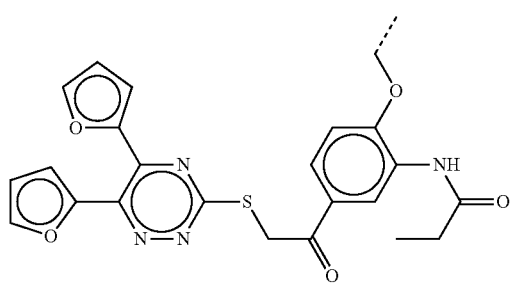 | 43.2 | 109.5 | 66.3 |
| 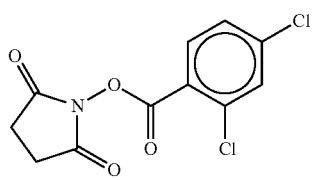 | 30.47645315 | 96.72727273 | 66.25081958 |
| 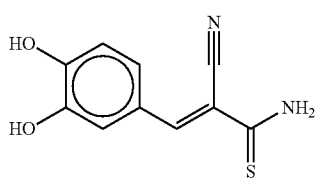 | 34.54623163 | 100.760843 | 66.2146114 |
| 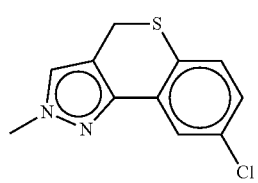 | 23.45468053 | 89.61072441 | 66.15604388 |
| 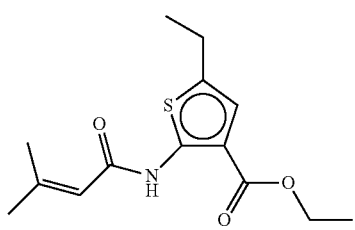 | 24.12504492 | 90.1231625 | 65.99811758 |

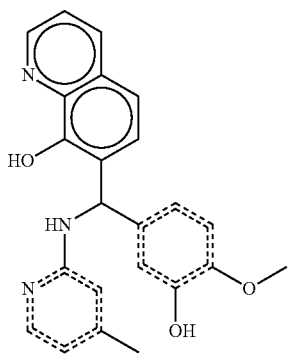 27.16644285 93.0177803 65.85133746
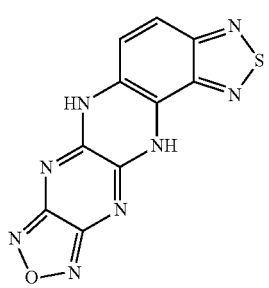 [SMILES: c1cc2nsnc2c2c1Nc1nc3nonc3nc1N2] −8.097006083 57.6845011 65.78150718
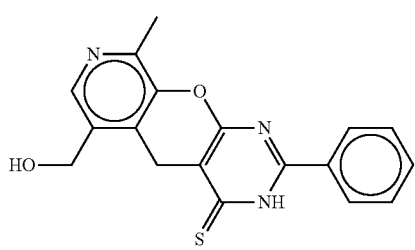 66'13604597 131.2029473 65.06690133
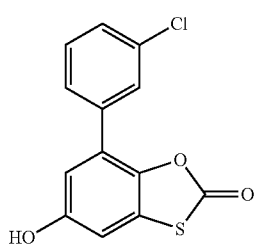 1119902121 76.15107324 6495205204
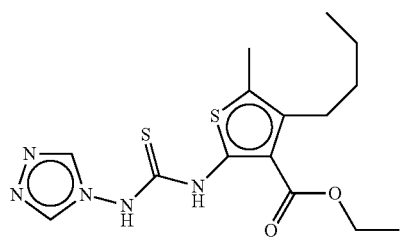 4.577793748 69.52721494 64.94942119
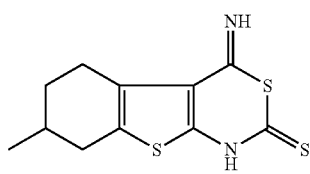 [SMILES: CC1CCc2c(sc3[nH]c(=S)sc(=N)c23)C1] 18.95094399 83.66485345 64.71390946

-continued
| | | | |
|---|---|---|---|
| 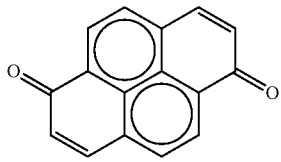 | 26.7 | 91.4 | 64.7 |
| 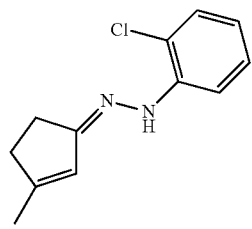 | 34.3965106 | 99.00834642 | 64.61183582 |
| 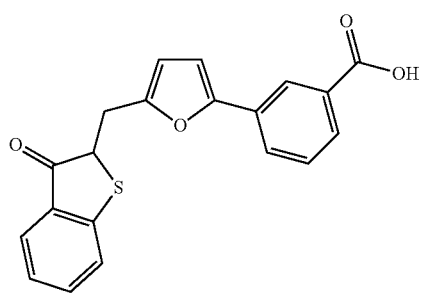 [SMILES: O=C(O)c1cccc(-c2ccc(CC3Sc4ccccc4C3=O)o2)c1] | 31.16639478 | 95.42028511 | 64.25389033 |
| 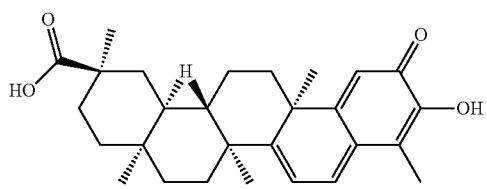 | 32.90443509 | 97.09434568 | 64.18991059 |
| 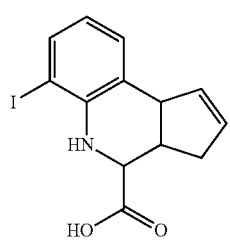 [SMILES: O=C(O)C1Nc2c(I)cccc2C2C=CCC12] | 36.11902501 | 100.2785294 | 64.15950436 |

-continued
| | | | |
|---|---|---|---|
| 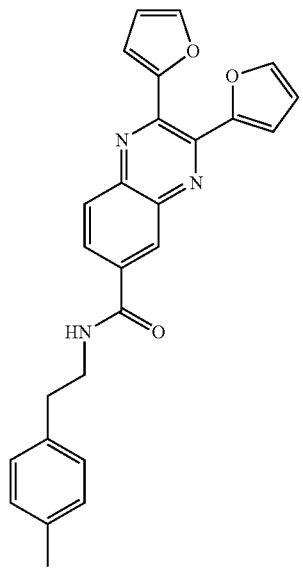 [SMILES: Cc1ccc(CCNC(=O)c2ccc3nc(-c4ccco4)c(-c4ccco4)nc3c2)cc1] | 35.72624681 | 99.74101397 | 64.01476715 |
| 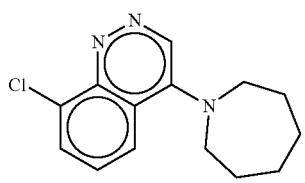 | 21.78361457 | 85.37461774 | 63.59100317 |
| 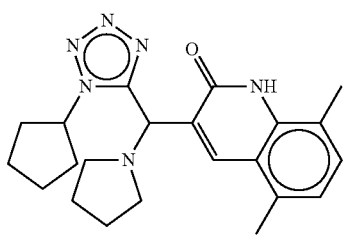 | 39.7488359 | 103.3154122 | 63.56657629 |
| 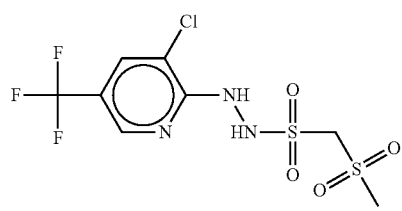 | 41.28528975 | 104.7348973 | 63.44960756 |
| 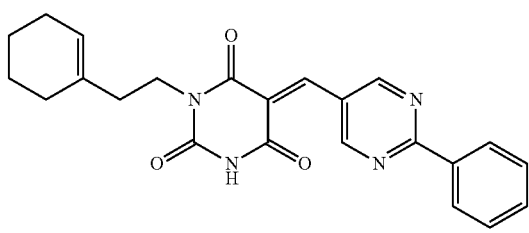 [SMILES: O=C1NC(=O)N(CCC2=CCCCC2)C(=O)/C1=C/c1cnc(-c2ccccc2)nc1] | 43.51306119 | 106.9095962 | 63.39653504 |

-continued

| Structure | | | |
|---|---|---|---|
| (bromo-phenyl-thiadiazole-spiro-indolinone) | 18.57176712 | 81.71632703 | 63.14455991 |
| (cyclopentylidene hydrazide benzamide thiophene sulfonamide) | 29.27084059 | 92.34063996 | 63.06979937 |
| (chlorobenzyl pyrazolopyrimidine carboxamide) | 31.39551493 | 94.41842001 | 63.02290508 |
| (chlorophenyl amino furyl thiophene ester) | 48.21516581 | 111.214653 | 62.99948715 |
| (chlorophenyl piperazine hydroxybenzoyl) | 27.71898883 | 90.70584478 | 62.98685595 |
| (chlorophenyl furyl methylisoxazolone) | 38.47471452 | 101.4501065 | 62.97539199 |

-continued
| | | | |
|---|---|---|---|
| 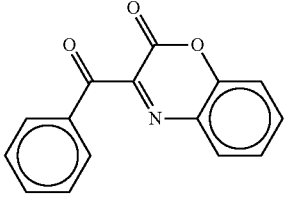 | −19.61126884 | 43.27239348 | 62.88366232 |
| 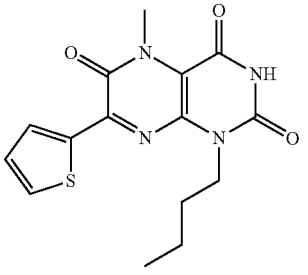 [SMILES: CCCCn1c(=O)[nH]c(=O)c2c1nc(-c1cccs1)c(=O)n2C] | 6.012957705 | 68.85183202 | 62.83887431 |
| 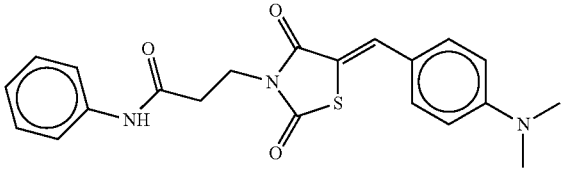 | 29.45492662 | 92.21556886 | 62.76064224 |
| 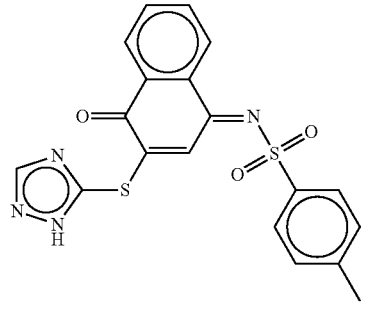 | 35.6 | 98.3 | 62.7 |
| 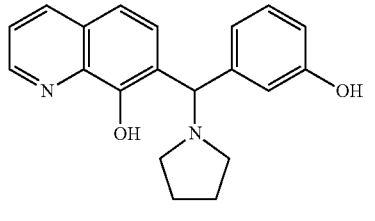 [SMILES: Oc1cccc(C(c2ccc3cccnc3c2O)N2CCCC2)c1] | 43.7012494 | 106.4084449 | 62.70719545 |
| 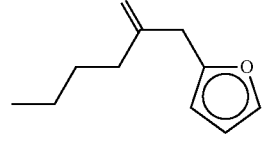 | 40.93873164 | 103.0201067 | 62.08137505 |
| 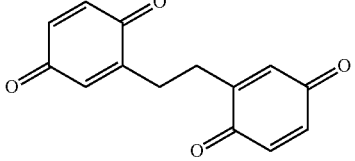 | 31.21264846 | 93.01166131 | 61.79901285 |

| | | | |
|---|---|---|---|
| 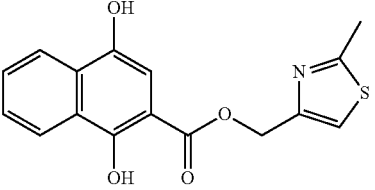 [SMILES: Cc1nc(COC(=O)c2cc(O)c3ccccc3c2O)cs1] | 39.52157023 | 101.2560945 | 61.73452431 |
| 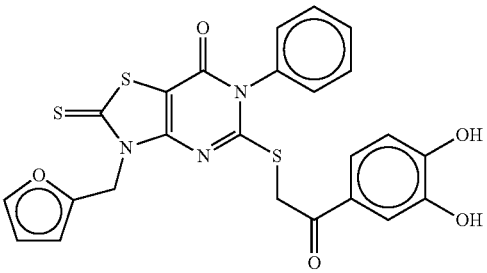 | 59.441744 | 120.9256794 | 61.48393538 |
| 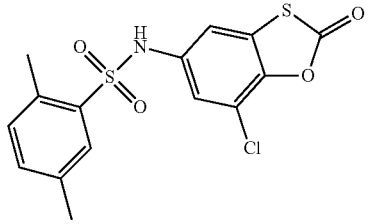 [SMILES: Cc1ccc(C)c(S(=O)(=O)Nc2cc(Cl)c3oc(=O)sc3c2)c1] | 25.38058602 | 86.7447645 | 61.36417848 |
| 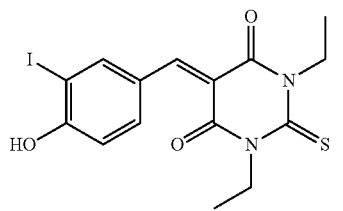 [SMILES: CCN1C(=O)C(=Cc2ccc(O)c(I)c2)C(=O)N(CC)C1=S] | 39.32183657 | 100.3628503 | 61.04101373 |
| 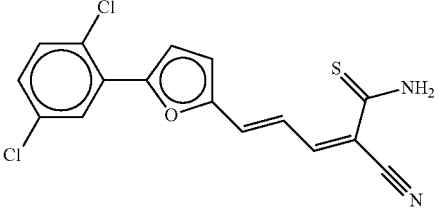 | 18.43595701 | 79.39308398 | 60.95712697 |
| 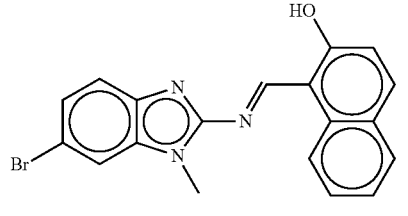 | −2964270278 | 31.23996145 | 60.88266423 |
| 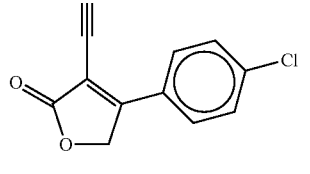 | 27.27621091 | 88.11755764 | 60.84134673 |

-continued
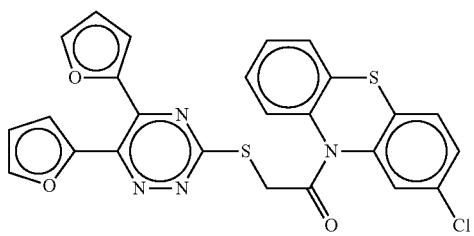 37.6 98.3 60.7
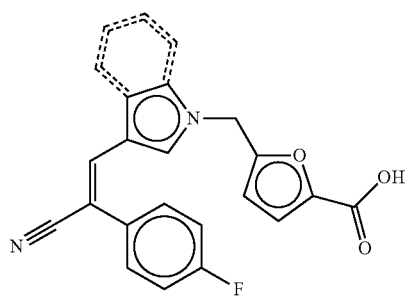 4.673280876 65.02894576 60.35566489
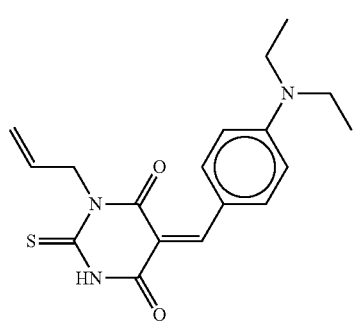 41.8167411 102.1683264 60.35158527
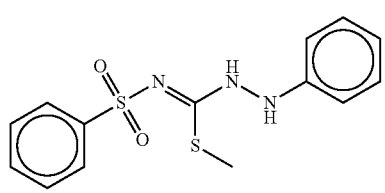 39.93161377 99.39343581 59.46182205
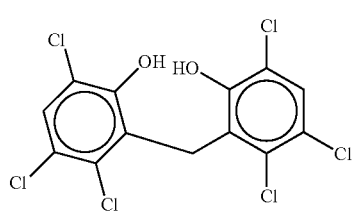 41.01271009 100.3606236 59.34791354
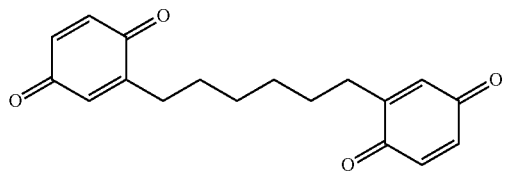 [SMILES: O=C1C=CC(=O)C(CCCCCCC2=CC(=O)C=CC2=O)=C1] 47.18965126 106.5320264 59.34237511

| | | | |
|---|---|---|---|
| 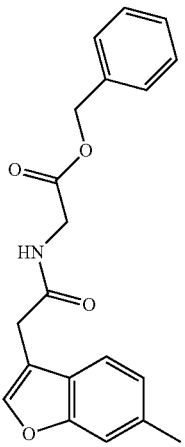 [SMILES: Cc1ccc2c(CC(=O)NCC(=O)OCc3ccccc3)coc2c1] | 36.55154869 | 95.64034877 | 59.08880009 |
| 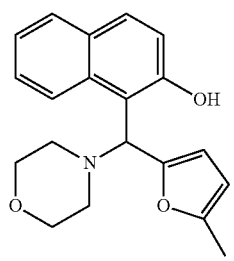 [SMILES: Cc1ccc(C(c2c(O)ccc3ccccc23)N2CCOCC2)o1] | 41.78912826 | 100.8274721 | 59.03834381 |
| 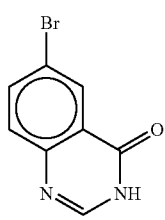 | 34.66750489 | 93.68924174 | 59.02173685 |
| 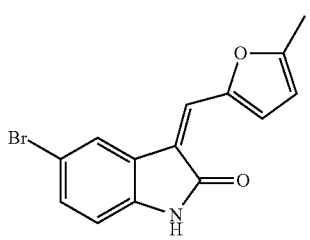 [SMILES: Cc1ccc(/C=C2\C(=O)Nc3ccc(Br)cc32)o1] | 18.74037573 | 77.59057823 | 58.85020251 |
| 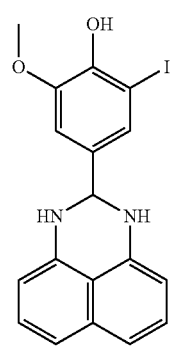 [SMILES: COc1cc(C2Nc3cccc4cccc(c34)N2)cc(I)c1O] | 22.81374655 | 81.47543659 | 58.66169004 |

-continued
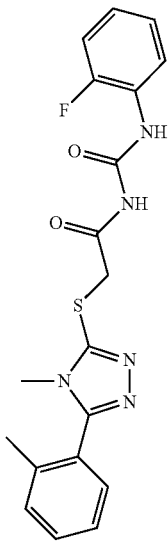 [SMILES: Cc1ccccc1-c1nnc(SCC(=O)NC(=O)Nc2ccccc2F)n1C]
39.52194519  98.09873249  58.5767873
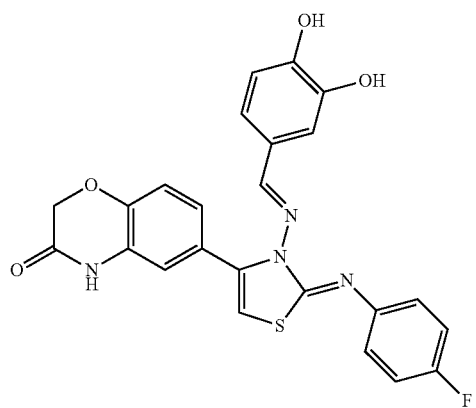 [SMILES: O=C1COc2ccc(-c3cs/c(=N\c4ccc(F)cc4)n3/N=C/c3ccc(O)c(O)c3)cc2N1]
39.11594696  97.6372151  58.52125455
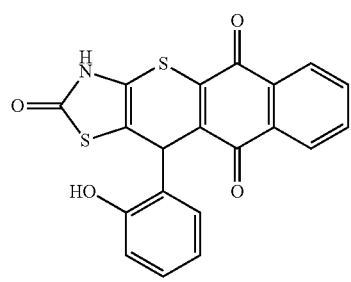 [SMILES: O=C1C2=C(C(=O)c3ccccc31)C(c1ccccc1O)c1sc(=O)[nH]c1S2]
30.40891164  88.85677858  58.44786694
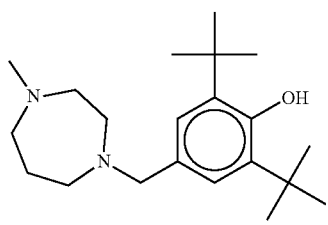
25.2061285  83.4987795  58.29265464

-continued
| | | |
|---|---|---|
| 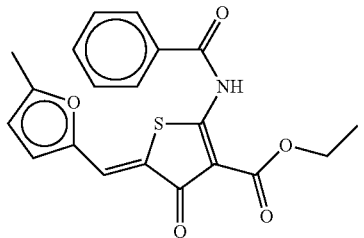 | 43.16379248 | 101.2275149 | 58.06372239 |
| 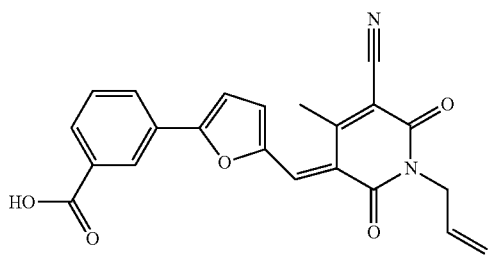 [SMILES: C=CCN1C(=O)C(C#N)=C(C)/C(=C\c2ccc(-c3cccc(C(=O)O)c3)o2)C1=O] | 31.4290114 | 89.23693465 | 57.80792326 |
| 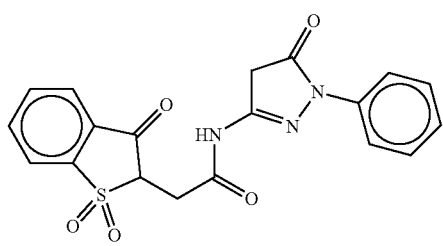 | 7.609675481 | 65.35257732 | 57.74290184 |
| 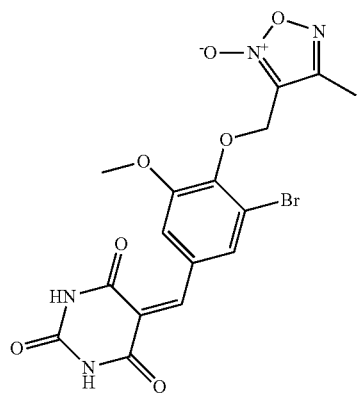 | 38.17542436 | 95.91685226 | 57.74142791 |
| 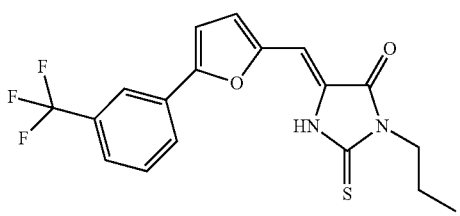 [SMILES: CCCN1C(=O)/C(=C/c2ccc(-c3cccc(C(F)(F)F)c3)o2)NC1=S] | 27.92957859 | 85.64814815 | 57.71856956 |
| 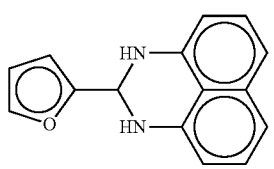 | 48.94267421 | 106.2615101 | 57.31883592 |

-continued
| | | | |
|---|---|---|---|
| 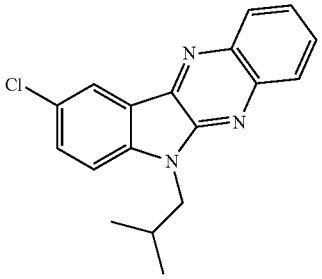 [SMILES: CC(C)Cn1c2ccc(Cl)cc2c2nc3ccccc3nc21] | 32.32116549 | 89.4407446 | 57.11957911 |
| 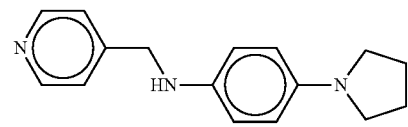 | 38.73289121 | 95.62561095 | 56.89271974 |
| 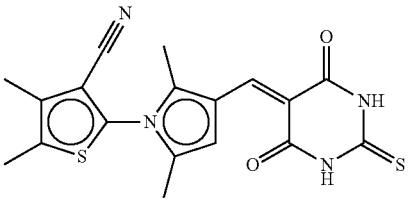 | 45.19897498 | 102.0166733 | 56.81769831 |
| 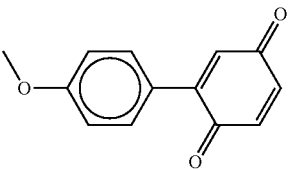 | 35.39582849 | 92.03372469 | 56.6378962 |
| 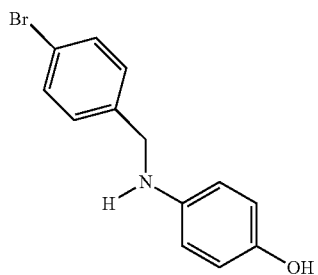 [SMILES: Oc1ccc(NCc2ccc(Br)cc2)cc1] | 34.63356974 | 90.94954311 | 56.31597337 |
| 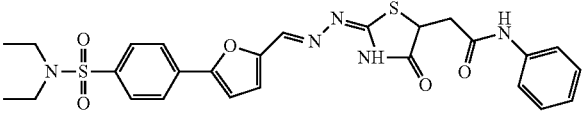 [SMILES: CCN(CC)S(=O)(=O)c1ccc(-c2ccc(/C=N/N=C3\NC(=O)C(CC(=O)Nc4ccccc4)S3)o2)cc1] | 44.3733406 | 100.6715454 | 56.29820482 |
| 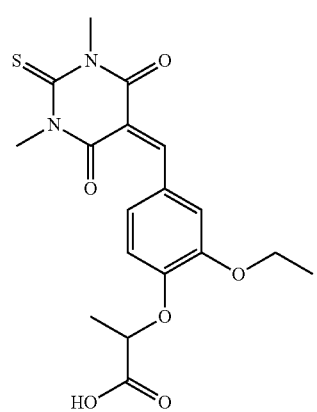 [SMILES: CCOc1cc(C=C2C(=O)N(C)C(=S)N(C)C2=O)ccc1OC(C)C(=O)O] | 41.985733 | 98.20470972 | 56.21897672 |

-continued
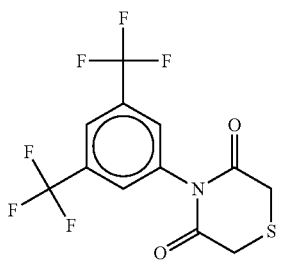 45.61615856 101.6646949 56.04853639
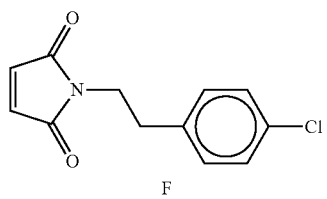 41.13775626 97.06777083 55.93001457
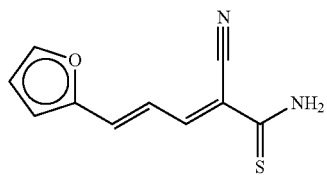 7.821811681 63.5443038 55.72249212
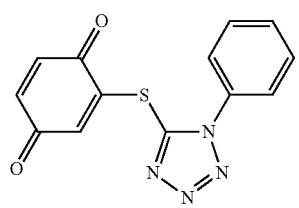 [SMILES: O=C1C=CC(=O)C(Sc2nnnn2-c2ccccc2)=C1] 45.56074766 101.2544661 55.69371839
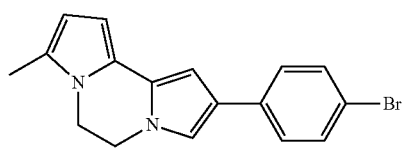 [SMILES: Cc1ccc2n1CCn1cc(-c3ccc(Br)cc3)cc1-2] 43.76933274 99.37348265 55.60414991
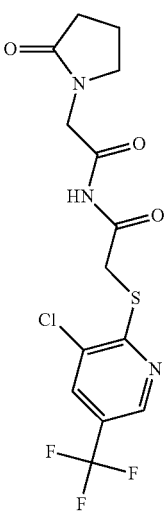 [SMILES: O=C(CSc1ncc(C(F)(F)F)cc1Cl)NC(=O)CN1CCCC1=O] 43.36958596 98.96808255 55.5984966

-continued
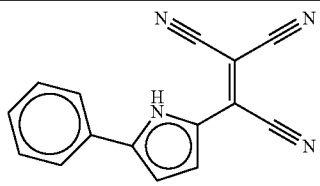
| | | |
|---|---|---|
| 35.11114267 | 90.69859962 | 55.58745694 |
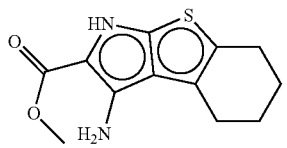
| | | |
|---|---|---|
| 29.48940031 | 85.03813193 | 55.54873162 |
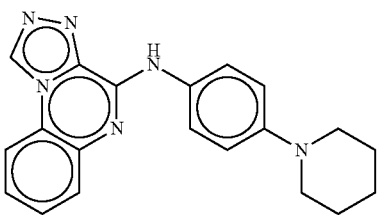
| | | |
|---|---|---|
| 35.03258269 | 90.44736221 | 55.41477952 |
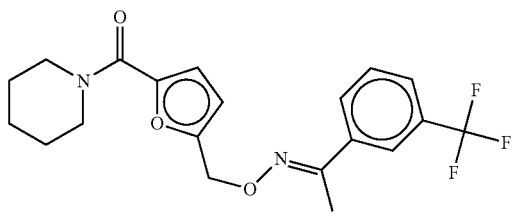
| | | |
|---|---|---|
| 55.47976701 | 110.818343 | 55.3385760 |
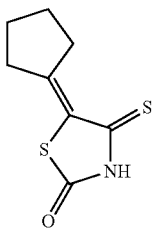 [SMILES: O=C1NC(=S)C(=C2CCCC2)S1]
| | | |
|---|---|---|
| 38.04746419 | 93.34466638 | 55.29720219 |
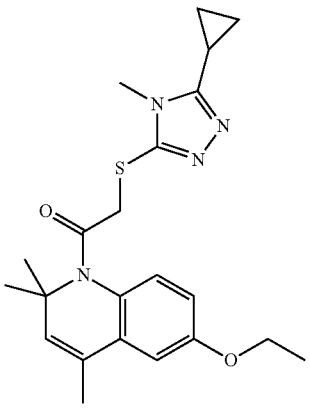 [SMILES: CCOc1ccc2c(c1)C(C)=CC(C)(C)N2C(=O)CSc1nnc(C2CC2)n1C]
| | | |
|---|---|---|
| 40.13238539 | 95.37388609 | 55.2415007 |
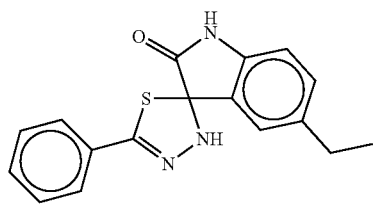
| | | |
|---|---|---|
| 44.19099554: | 99.42563929 | 55.23464375 |

-continued
| | | | |
|---|---|---|---|
| 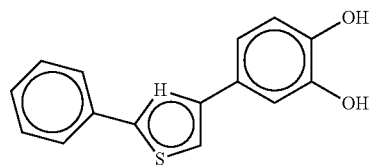 | 33.24656324 | 87.76949553 | 54.52293229 |
| 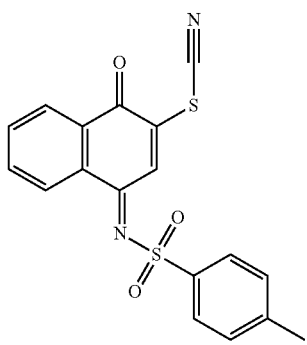 [SMILES: Cc1ccc(S(=O)(=O)/N=C2\C=C(SC#N)C(=O)c3ccccc32)cc1] | 36.15465782 | 91.34577213 | 55.19111431 |
| 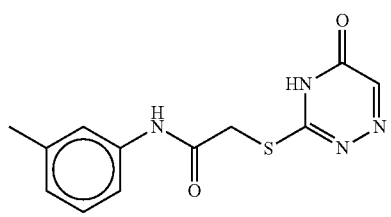 | 27.2754491 | 82.27419222 | 54.99874311 |
| 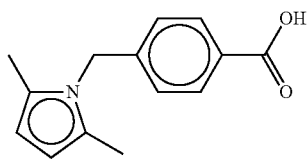 | 36.59699818 | 91.44689379 | 54.84989561 |
| 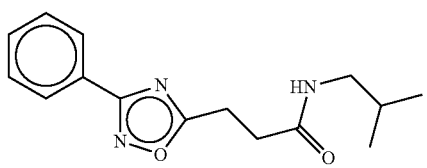 | 37.48100881 | 92.20830691 | 54.7272981 |
| 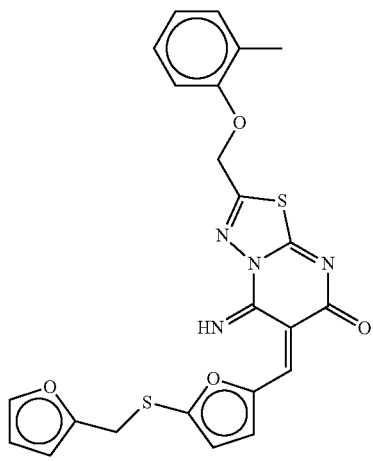 | 19.17808219 | 73.82692962 | 54.64884742 |

-continued
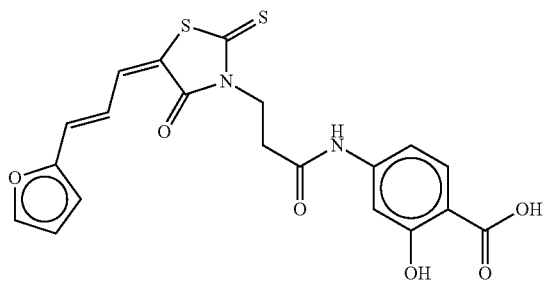 21.54074074 76.08572124 54.5449805
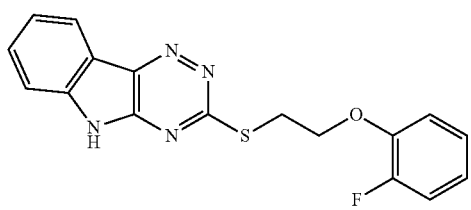 [SMILES: Fc1ccccc1OCCSc1nnc2c(n1)[nH]c1ccccc12] 45.20486556 99.55872914 54.35386358
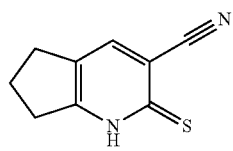 [SMILES: N#Cc1cc2c([nH]c1=S)CCC2] 32.60195759 86.63771915 54.03576157
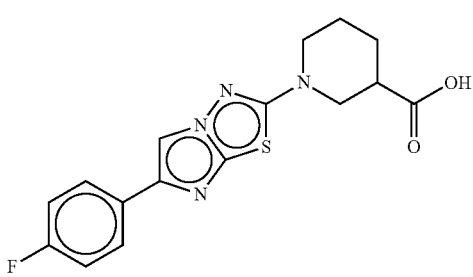 28.03761445 82.01902665 53.9814122
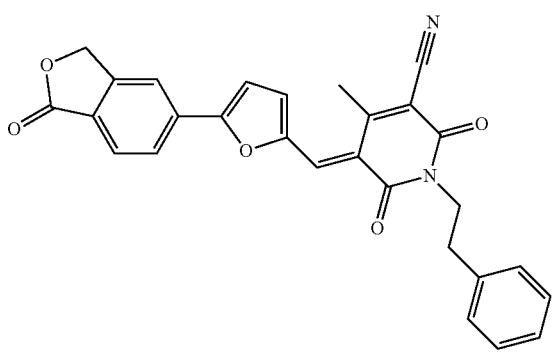 [SMILES: CC1=C(C#N)C(=O)N(CCc2ccccc2)C(=O)/C1=C/c1ccc(-c2ccc3c(c2)COC3=O)o1] 30.81305821 84.78776478 53.97470658
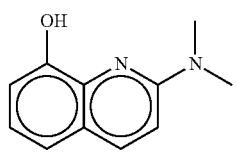 41.22497055 95.08543531 53.86046476

| | | | |
|---|---|---|---|
| 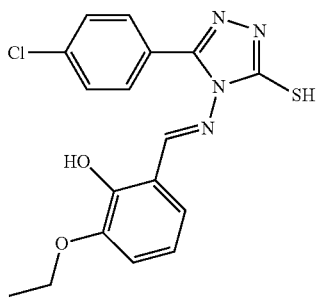 [SMILES: CCOc1cccc(/C=N/n2c(S)nnc2-c2ccc(Cl)cc2)c1O] | 42.82815987 | 96.57675493 | 53.74859506 |
| 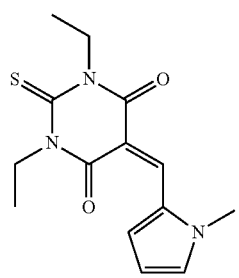 [SMILES: CCN1C(=O)C(=Cc2cccn2C)C(=O)N(CC)C1=S] | 52.01193335 | 105.6743612 | 53.6624278 |
| 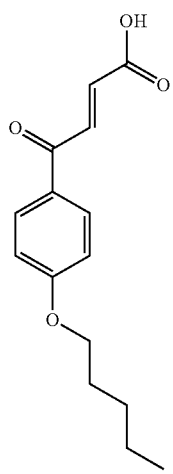 [SMILES: CCCCCOc1ccc(C(=O)/C=C/C(=O)O)cc1] | 43.85063378 | 97.46473998 | 53.61410621 |
| 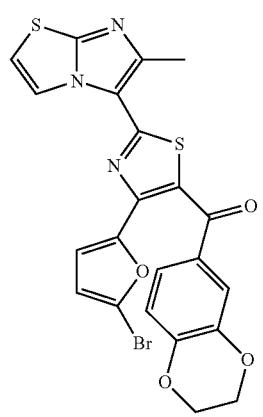 [SMILES: Cc1nc2sccn2c1-c1nc(-c2ccc(Br)o2)c(C(=O)c2ccc3c(c2)OCCO3)s1] | 39.74584291 | 93.29913695 | 53.55329404 |

-continued
| | | | |
|---|---|---|---|
| 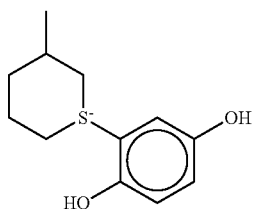 | 41.15745598 | 94.72268477 | 53.56522879 |
| 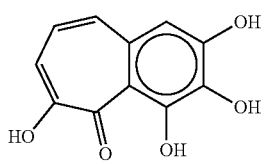 | −19.8129509 | 33.73781755 | 53.55076845 |
| 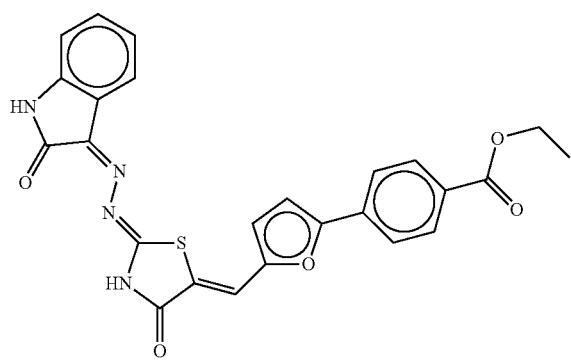 | 13.28219273 | 66.62503346 | 53.34284073 |
| 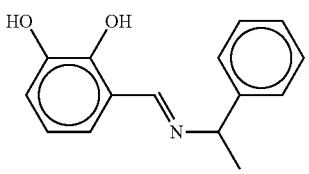 | 40.42061339 | 93.71157747 | 53.29096408 |
| 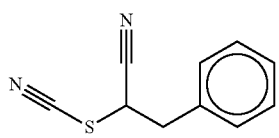 | 50.38587118 | 103.6178964 | 53.23202524 |
| 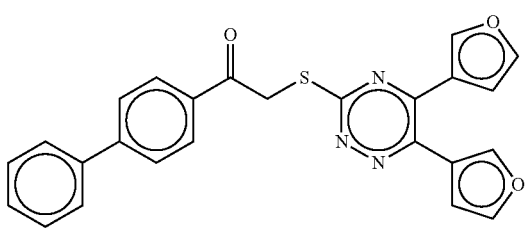 | 45.37762426 | 98.52069172 | 53.14306746 |
| 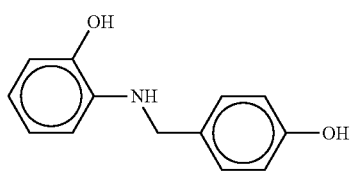 | 36.25704957 | 89.38134811 | 53.12429854 |

-continued
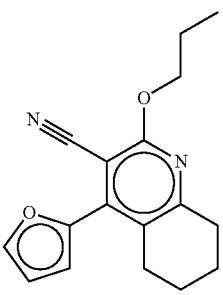
30.70619785 83.66680278 52.96060492
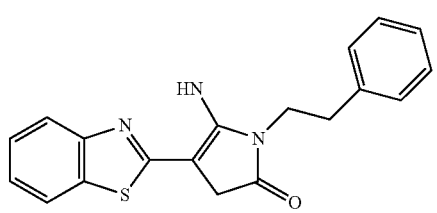 [SMILES: NC1=C(c2nc3ccccc3s2)CC(=O)N1CCc1ccccc1]
55.56846133 108.4823958 52.91393446
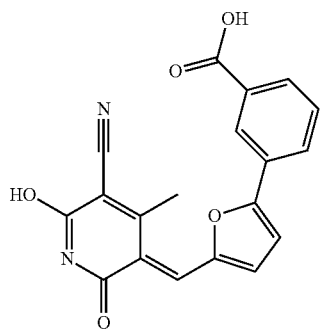 [SMILES: CC1=C(C#N)C(O)=NC(=O)/C1=C/c1ccc(-c2cccc(C(=O)O)c2)o1]
36.80576864 89.70132202 52.89555338
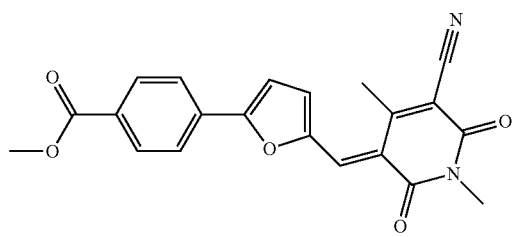
38.82044965 91.59237753 52.77192788
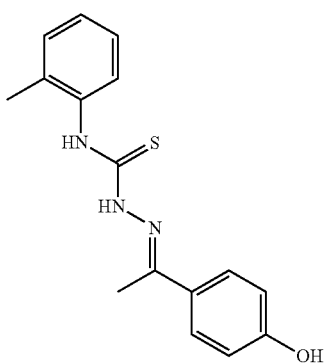 [SMILES: C/C(=N\NC(=S)Nc1ccccc1C)c1ccc(O)cc1]
50.81668419 103.4121817 52.59549746

-continued
| | | | |
|---|---|---|---|
| 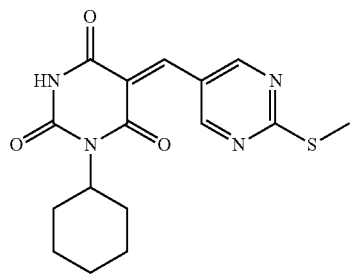 [SMILES: CSc1ncc(/C=C2/C(=O)NC(=O)N(C3CCCCC3)C2=O)cn1] | 46.42363385 | 99.00409172 | 52.58045787 |
| 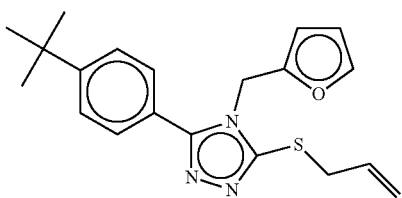 | 69.98574323! | 122.2854715 | 52.29972831 |
| 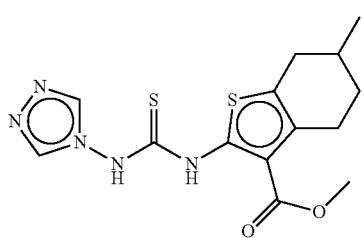 | 25.26217665 | 77.54573418 | 52.28355753 |
| 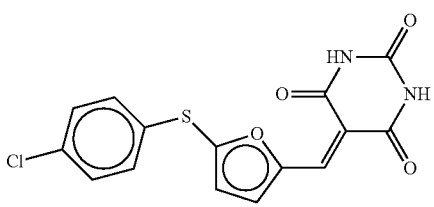 | 39.96352925 | 92.21643287 | 52.25290362 |
| 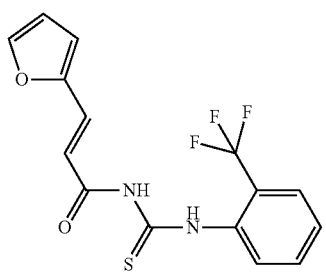 [SMILES: O=C(/C=C/c1ccco1)NC(=S)Nc1ccccc1C(F)(F)F] | 47.00574838 | 99.25113873 | 52.24539035 |

-continued
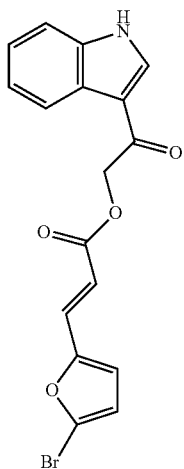 [SMILES: O=C(/C=C/c1ccc(Br)o1)OCC(=O)c1c[nH]c2ccccc12]  53.4905597  105.6295695  52.13900976
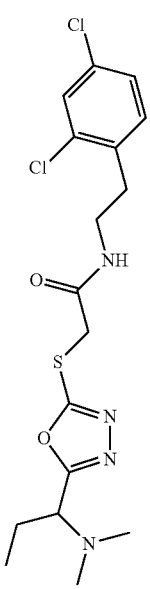 [SMILES: CCC(c1nnc(SCC(=O)NCCc2ccc(Cl)cc2Cl)o1)N(C)C]  49.44050318  101.5763783  52.13587515
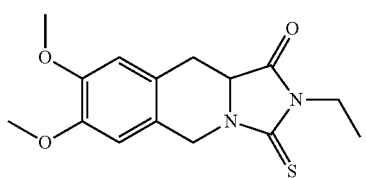  39.83535868  91.73339804  51.89803936
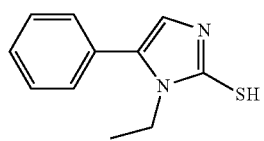  54.02808574  105.7595451  51.73145935

-continued
| | | | |
|---|---|---|---|
| 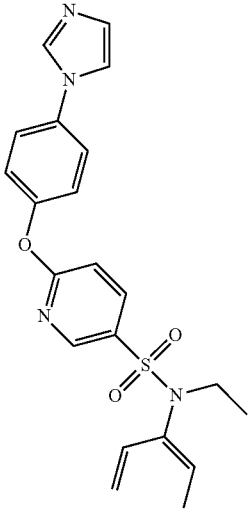 [SMILES: C=C/C(=C\C)N(CC)S(=O)(=O)c1ccc(Oc2ccc(-n3ccnc3)cc2)nc1] | 51.20524073 | 102.9357651 | 51.73052441 |
| 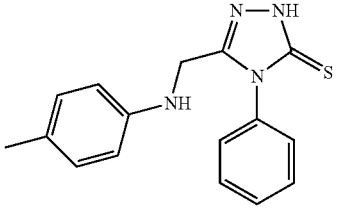 [SMILES: Cc1ccc(NCc2n[nH]c(=S)n2-c2ccccc2)cc1] | 43.22472716 | 94.84355045 | 51.61882329 |
| 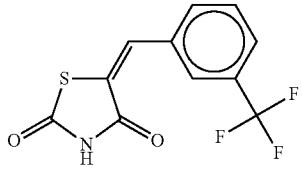 | 42.5929832 | 94.16497422 | 51.57199103 |
| 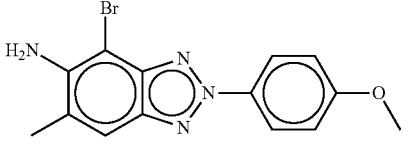 | 32.55627595 | 83.96631306 | 51.41003711 |
| 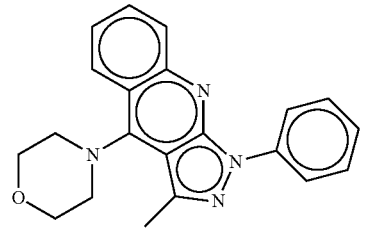 | 47.31068916 | 98.28460368 | 50.97391452 |
| 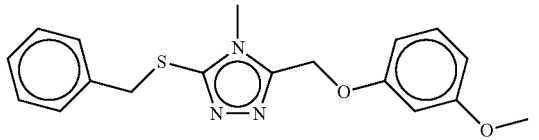 | 46.55678968 | 97.50512926 | 50.94833958 |

| | | | |
|---|---|---|---|
| 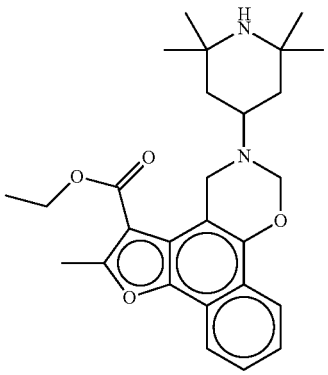 | 34.10555385 | 85.00081606 | 50.89526221 |
| 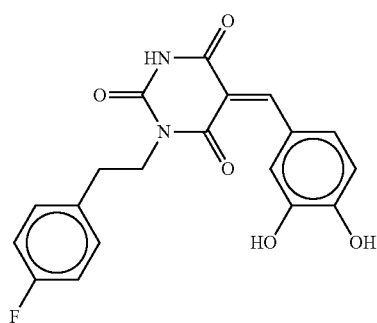 | 30.59011861 | 81.34023006 | 50.75011146 |
| 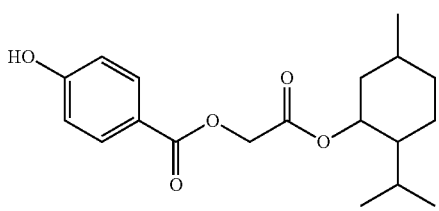 [SMILES: CC1CCC(C(C)C)C(OC(=O)COC(=O)c2ccc(O)cc2)C1] | 55.74433657 | 106.4705403 | 50.72620373 |
| 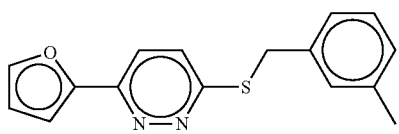 | 44.76047904 | 95.3640195 | 50.60354046 |
| 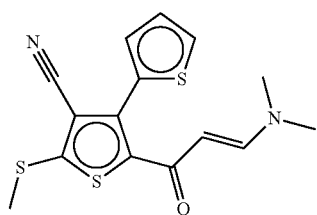 | −20.05671367 | 30.41972806 | 50.47644174 |
| 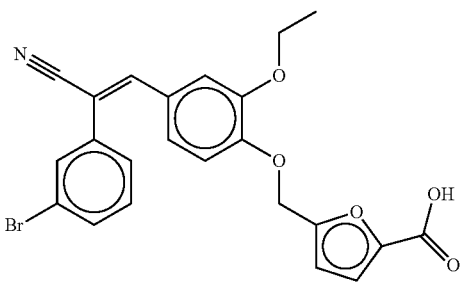 | 35.60617193 | 85.8825454 | 50.27637346 |

| | | | |
|---|---|---|---|
| 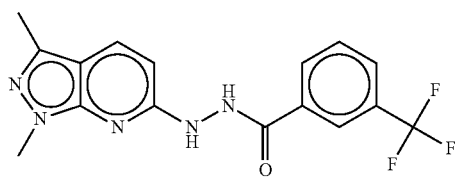 | 57.07388105 | 107.3051263 | 50.2312452 |
| 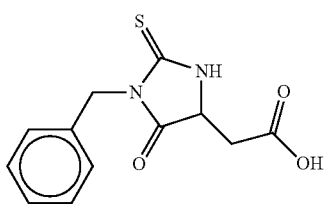 | 48.7076967 | 98.89474361 | 50.1870469 |
| 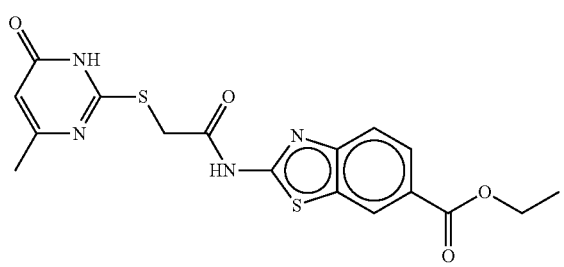 | 56.5514328 | 106.3303342 | 49.77890139 |
| 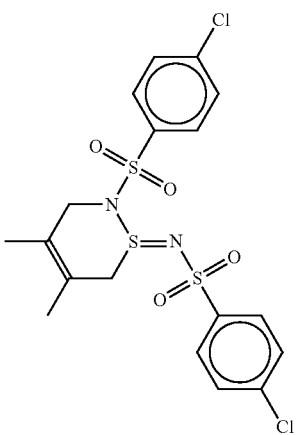 | 50.4177415' | 100.1803601 | 49.76261858 |
| 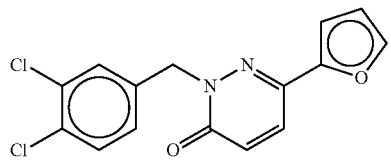 | 46.79236779 | 96.49484536 | 49.70247757 |
| 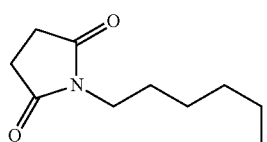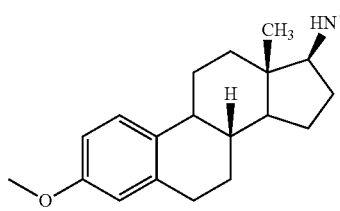 | 56.60157162 | 106.2747212 | 49.67314961 |

-continued
| | | | |
|---|---|---|---|
| 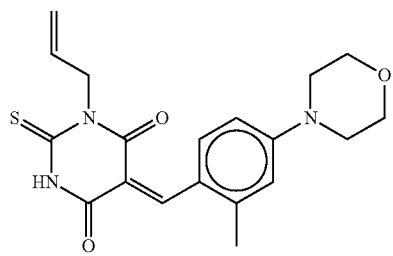 | 33.00999412 | 82.65729799 | 49.64730387 |
| 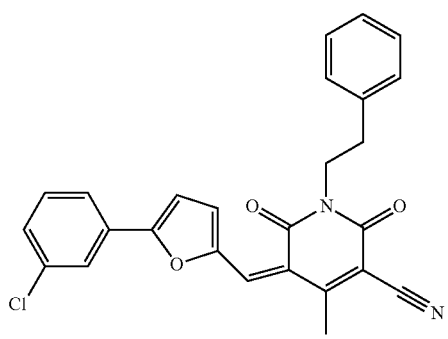 [SMILES: CC1=C(C#N)C(=O)N(CCc2ccccc2)C(=O)/C1=C\c1ccc(-c2cccc(Cl)c2)o1] | 29.33477056 | 78.76829966 | 49.43352911 |
| 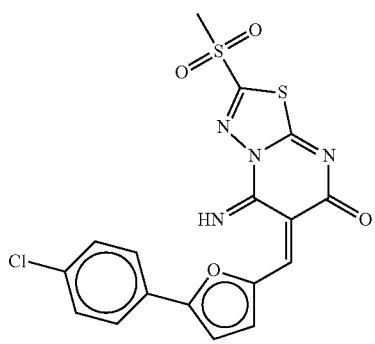 | 33.27874504 | 82.61218664 | 49.33344159 |
| 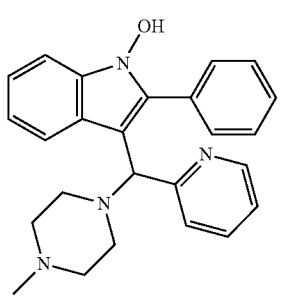 [SMILES: CN1CCN(C(c2ccccn2)c2c(-c3ccccc3)n(O)c3ccccc23)CC1] | 50.5499649 | 99.82531364 | 49.275348751 |
| 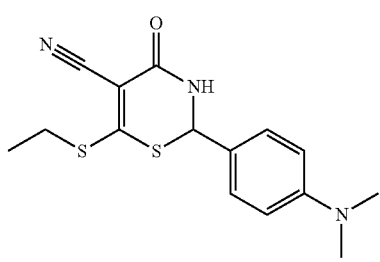 [SMILES: CCSC1=C(C#N)C(=O)NC(c2ccc(N(C)C)cc2)S1] | 30.48780488 | 79.68386424 | 49.19605936! |

-continued

| Structure | | | |
|---|---|---|---|
| (4-bromophenyl furan acrylamide) | 47.95352324 | 96.90361633 | 48.95009309 |
| (chloro-methylphenyl pyrrolidinedione tetrahydroquinoline) | 35.81991695 | 84.74370394 | 48.923786139 |
| (tert-butylphenyl triazole-thiol) | 47.9673093 | 96.80006481 | 48.8327555 |
| (trifluoromethylphenyl methylfuran carboxylic acid) | 33.22160149 | 81.90084605 | 48.67924456 |
| (furan-propenylidene thiazolidinone phenylimine) | 48.95344507 | 97.58836088 | 48.63491581 |
| (tetrahydroisoquinoline cyclohexyl tetrazole methoxyphenol) | 57.44228744 | 105.7704113 | 48.32812389 |
| (benzothiazole aminothiophene methylamino thienyl ketone) | 44.25172198 | 92.47479302 | 48.22307104 |

-continued
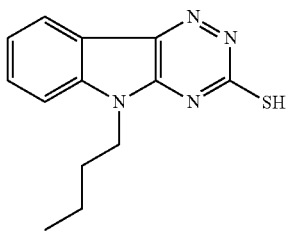 [SMILES: CCCCn1c2ccccc2c2nnc(S)nc21]
| | | |
|---|---|---|
| 44.23800949 | 92.39348471 | 48.15547522 |
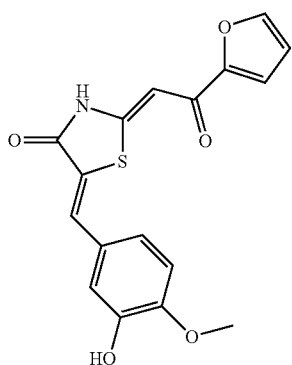 [SMILES: COc1ccc(/C=c2\s/c(=C\C(=O)c3ccco3)[nH]c2=O)cc1O]
| | | |
|---|---|---|
| 215.6015433 | 263.7374061 | 48.13586273 |
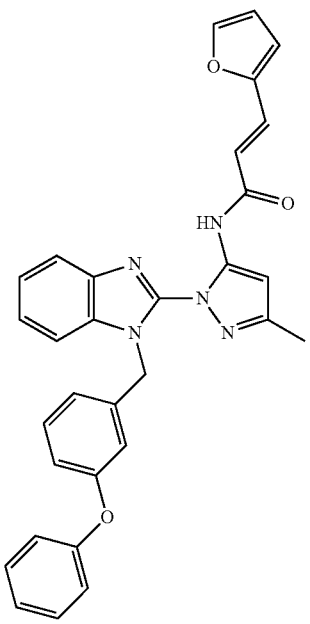 [SMILES: Cc1cc(NC(=O)/C=C/c2ccco2)n(-c2nc3ccccc3n2Cc2cccc(Oc3ccccc3)c2)n1]
| | | |
|---|---|---|
| 56.33127545 | 104.4315992 | 48.10032378 |
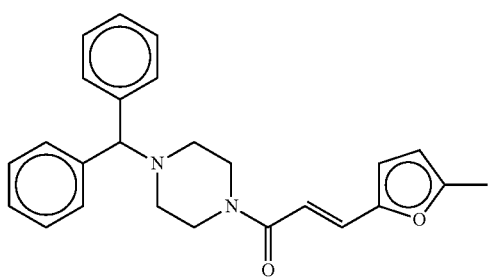
| | | |
|---|---|---|
| 55.14812663 | 103.2306124 | 48.08248577 |

-continued
| | | | |
|---|---|---|---|
| 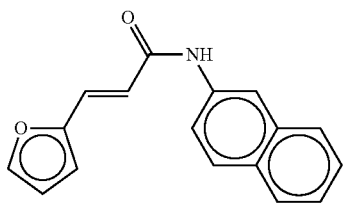 | 64.63766028 | 112.7047864 | 48.0671261 |
| 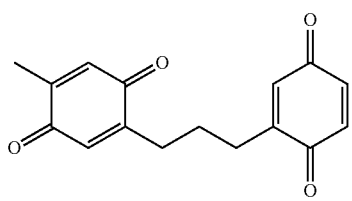 [SMILES: CC1=CC(=O)C(CCCC2=CC(=O)C=CC2=O)=CC1=O] | 44.40577956 | 92.47084671 | 48.06506715 |
| 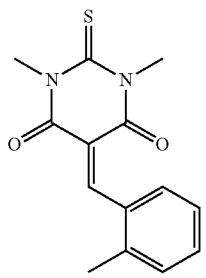 [SMILES: Cc1ccccc1C=C1C(=O)N(C)C(=S)N(C)C1=O] | 51.18862475 | 99.22340759 | 48.03478284 |
| 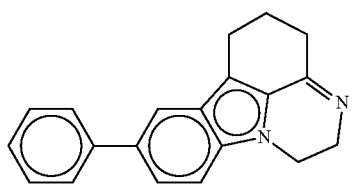 | 20.34336068 | 68.23874445 | 47.89538377 |
| 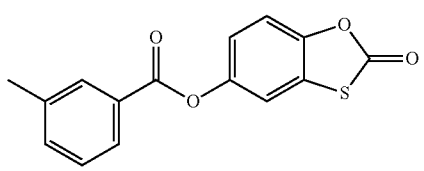 [SMILES: Cc1cccc(C(=O)Oc2ccc3oc(=O)sc3c2)c1] | 44.3557943 | 92.23836973 | 47.88257544 |
| 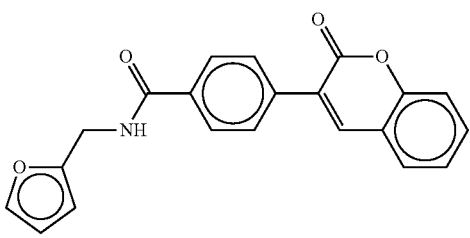 | 67.95159426 | 115.7456877 | 47.79409342 |
| 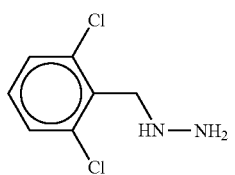 | 55.76098501 | 103.5302403 | 47.76925533 |

| | | | |
|---|---|---|---|
| 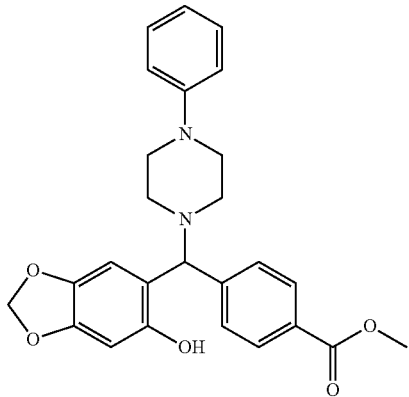 [SMILES: COC(=O)c1ccc(C(c2cc3c(cc2O)OCO3)N2CCN(c3ccccc3)CC2)cc1] | 48.75160508 | 96.45841953 | 47.70681445 |
| 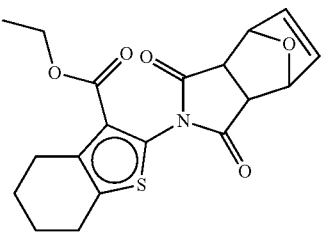 | 48.26958106 | 95.97238934 | 47.70280828 |
| 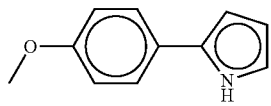 | 69.86140798 | 117.5434343 | 47.68202636 |
| 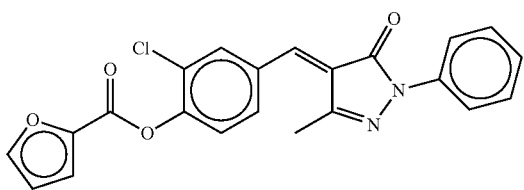 | 48.52722404 | 96.19903793 | 47.67181389 |
| 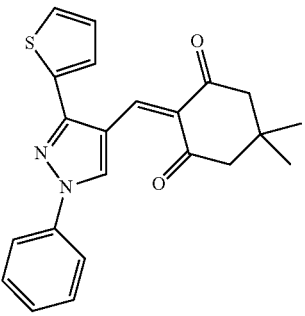 [SMILES: CC1(C)CC(=O)C(=Cc2cn(-c3ccccc3)nc2-c2cccs2)C(=O)C1] | 40.64114251 | 88.27679138 | 47.63564887 |
| | 43.06535747 | 90.61530929 | 47.54995182 |
| 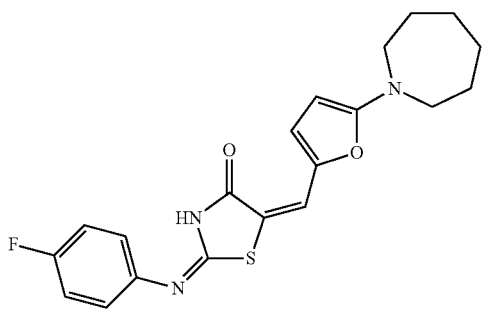 [SMILES: O=C1N/C(=N\c2ccc(F)cc2)S/C1=C/c1ccc(N2CCCCCC2)o1] | 40.42192793 | 87.79749734 | 47.37556941 |

| | | | |
|---|---|---|---|
| [structure: 1-phenyl-3-((5-methylfuran-2-yl)methylene)indolin-2-one] | 62.7184466 | 110.0825659 | 47.36411929 |
| [structure: 5-((5-(4-sulfamoylphenyl)furan-2-yl)methylene)-3-isobutyl-2-thioxothiazolidin-4-one] | 58.50862999 | 105.8574397 | 47.34880968 |
| [structure: N-(3-ethoxybenzyl)-4-(pyrrolidin-1-yl)aniline] | 34.93352497 | 82.24076281 | 47.30723784 |
| [structure: methyl 2-(cyclopropanecarboxamido)-4,5-dimethylthiophene-3-carboxylate] | 53.71064468 | 101.0010865 | 47.29044177 |
| [structure: 4-(((3-(trifluoromethyl)phenyl)imino)methyl)benzene-1,3-diol] | 28.42089641 | 75.68202804 | 47.26113163 |
| [structure: methyl 4-(2-chlorophenyl)-5-cyano-6-mercapto-2-oxo-1,2,3,4-tetrahydropyridine-3-carboxylate] | 47.02449336 | 94.14723747 | 47.12274411 |
| [structure: 5-mercapto-4-methyl-N-(3-(trifluoromethyl)phenyl)-4H-1,2,4-triazole-3-methanamine] | 55.0937101 | 102.2099448 | 47.11623465 |

-continued
| | | | |
|---|---|---|---|
| 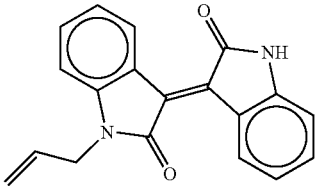 | 30.48240503 | 77.54573418 | 47.06332914 |
| 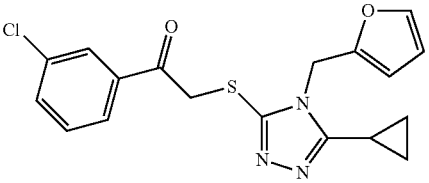 [SMILES: O=C(CSc1nnc(C2CC2)n1Cc1ccco1)c1cccc(Cl)c1] | 51.13822161 | 98.19719754 | 47.05897593 |
| 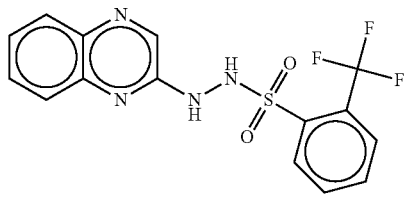 | 65.41604755 | 112.4344762 | 47.01842869 |
| 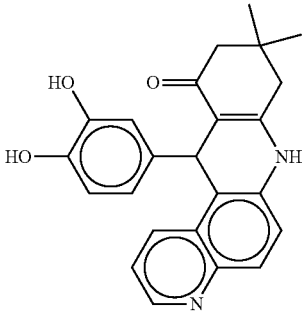 | 48.322054 | 95.33022533 | 47.00817133 |
| 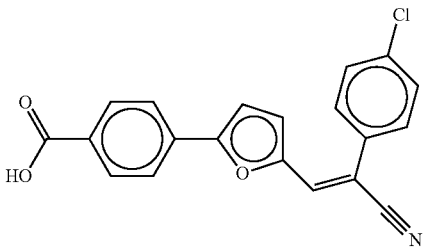 | 35.82692457 | 82.4672171 | 46.64029252 |
| 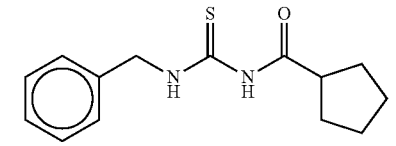 | 45.64428312 | 92.1013059 | 46.45702277 |
| 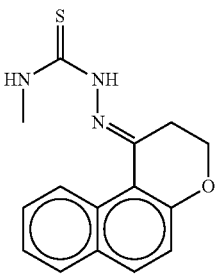 | 49.68408533 | 96.06979643 | 46.38571109 |

| | | | |
|---|---|---|---|
| (structure: tetrahydro-thieno-triazolo-quinazoline with SH) | 48.65415987 | 95.02703588 | 46.37287601 |
| 4,4'-dihydroxydiphenyl disulfide | 58.11789038 | 104.3981674 | 46.28027705 |
| (furan-acrylamide-ethyl-triazole-methoxyphenyl structure) | 40.50995892 | 86.74650699 | 46.23654806 |
| (2-mercapto-5-phenyl-penta-2,4-dienoic acid) | 44.35757282 | 90.48873778 | 46.13116496 |
| (dithiolo-quinoline-thione with thiocyanatoacetyl) | 47.01730419 | 93.0593376 | 46.04203341 |
| (3,5-di-tert-butyl-4-hydroxybenzyl-N-methyl-1-methylpiperidin-4-yl amine) | 63.36025402 | 109.3342199 | 45.97396591 |

-continued
| | | | |
|---|---|---|---|
| 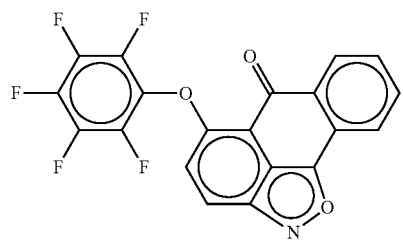 | 40.75591985 | 86.72661643 | 45.97068657 |
| 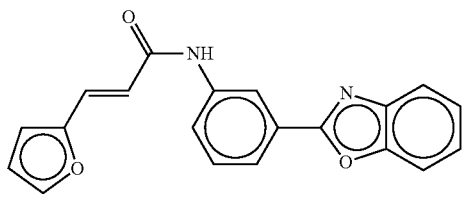 | 66.09053804 | 111.9999168 | 45.90937874 |
| 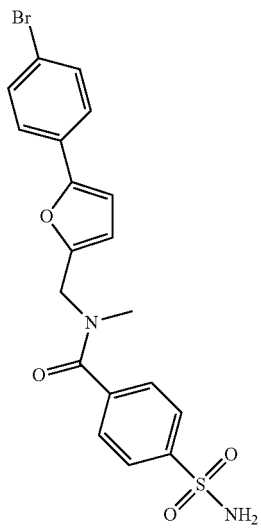 [SMILES: CN(Cc1ccc(-c2ccc(Br)cc2)o1)C(=O)c1ccc(S(N)(=O)=O)cc1] | 69.53461354 | 115.1985743 | 45.66396079 |
| 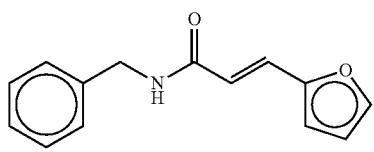 | 56.10428305 | 101.763264 | 45.65898096 |
| 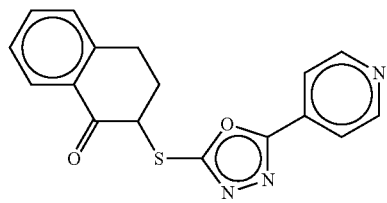 | 42.83942002 | 88.37759042 | 45.5381704 |
| 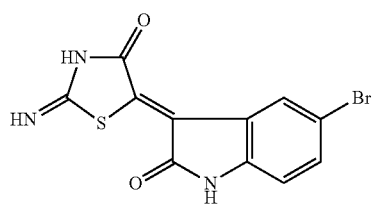 [SMILES: N=C1NC(=O)/C(=C2/C(=O)Nc3ccc(Br)cc32)S1] | 50.06136852 | 95.57695446 | 45.51558595 |

-continued
| | | | |
|---|---|---|---|
| 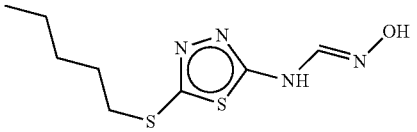 | 52.76268116 | 98.25183684 | 45.48915568 |
| 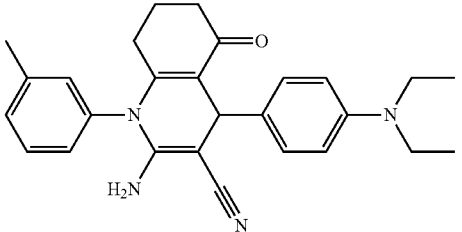 [SMILES: CCN(CC)c1ccc(C2C(C#N)=C(N)N(c3cccc(C)c3)C3=C2C(=O)CCC3)cc1] | 53.00666405 | 98.46315619 | 45.45649214 |
| 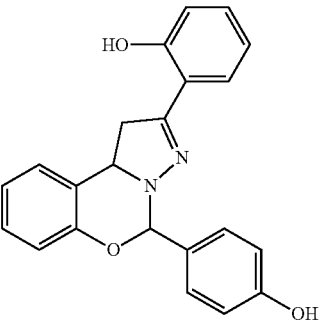 [SMILES: Oc1ccc(C2Oc3ccccc3C3CC(c4ccccc4O)=NN32)cc1] | 47.98902391 | 93.41583758 | 45.42681367 |
| 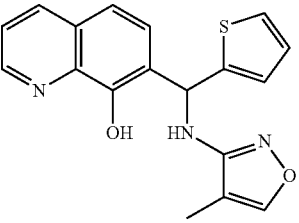 [SMILES: Cc1conc1NC(c1cccs1)c1ccc2cccnc2c1O] | 58.33277892 | 103.7511722 | 45.41839332 |
| 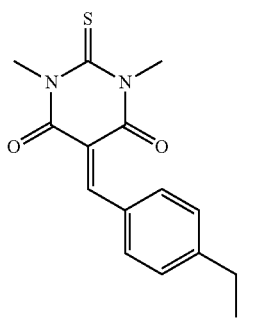 [SMILES: CCc1ccc(C=C2C(=O)N(C)C(=S)N(C)C2=O)cc1] | 55.45434348 | 100.8550361 | 45.4006926 |
| 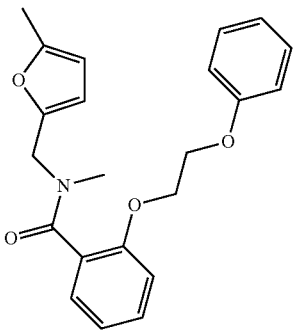 [SMILES: Cc1ccc(CN(C)C(=O)c2ccccc2OCCOc2ccccc2)o1] | 68.79611916 | 114.1804937 | 45.38437457 |

-continued
| | | |
|---|---|---|
| 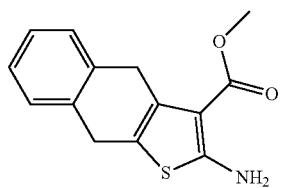 [SMILES: COC(=O)c1c(N)sc2c1Cc1ccccc1C2] | 47.68581216 | 92.92784163 | 45.24202948 |
| 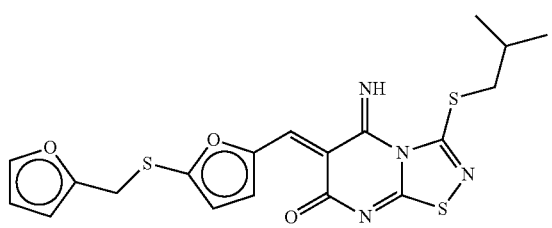 | 37.60579356 | 82.80346821 | 45.19767465 |
| 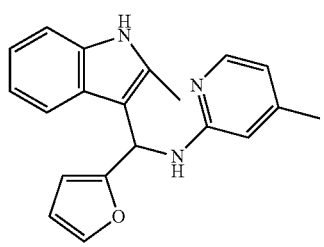 [SMILES: Cc1ccnc(NC(c2ccco2)c2c(C)[nH]c3ccccc23)c1] | 49.80397458 | 94.9926722 | 45.18869762 |
| 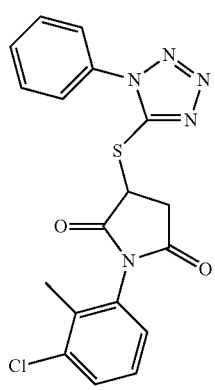 [SMILES: Cc1c(Cl)cccc1N1C(=O)CC(Sc2nnnn2-c2ccccc2)C1=O] | 52.42631325 | 97.49812983 | 45.07181658 |

TABLE 1-O

| Structure | Structure |
|---|---|
| (chemical structure) | (chemical structure) |
| (chemical structure) | (chemical structure) |

TABLE 1-P

| Bioactive | Structure | MCL-1% Bound | BCL-XL % Bound | Spec Values |
|---|---|---|---|---|
| Myricetin | (chemical structure) | 34.13126397 | 102.3629331 | 68.23166909 |
| Quercetin | (chemical structure) | 16.68871081 | 105.3416001 | 88.65288929 |

-continued
| | | | | |
|---|---|---|---|---|
| Tyrphostin 47 | 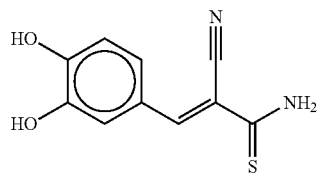 | 34.54623163 | 100.760843 | 66.2146114 |
| Manoalide | 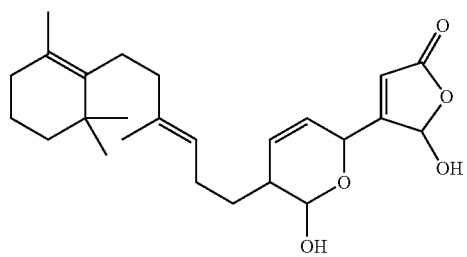 [SMILES: CC1=C(CC/C(C)=C/CCC2C=CC(C3=CC(=O)OC3O)OC2O)C(C)(C)CCC1] | 35.01128141 | 106.8345939 | 71.8233125 |
| U73122 | 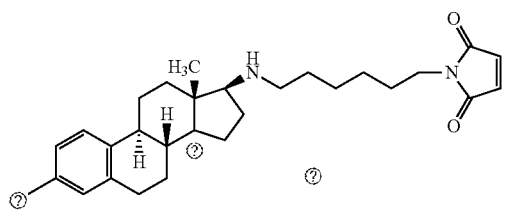 | 56.60157162 | 106.2747212 | 49.67314961 |
| Baicailen | 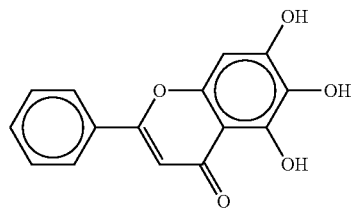 | 10.32290702 | 104.1661092 | 93.84320213 |
| Dyclonine | 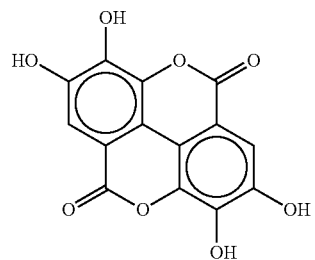 | 1.259544221 | 90.57802572 | 89.3184815 |
| Bithionol | 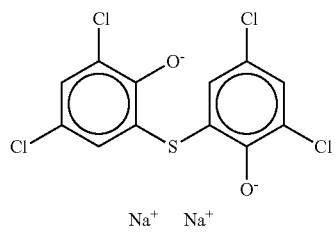 | 27.20036677 | 100.4228001 | 73.22243335 |

| | | | | |
|---|---|---|---|---|
| Gossypol | 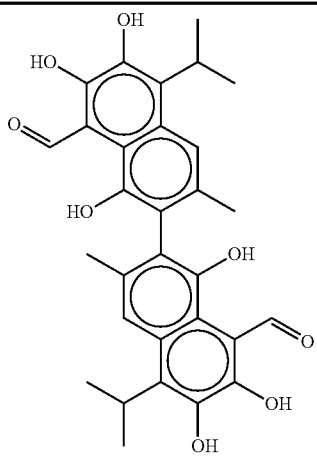 | 3.955080904 | 101.0243434 | 97.0692625 |
| Hexachlorophene | 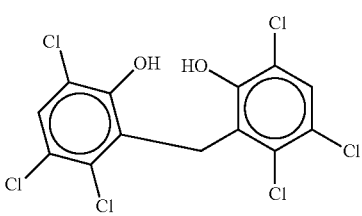 | 41.01271009 | 100.3606236 | 59.34791354 |
| Celastrol | 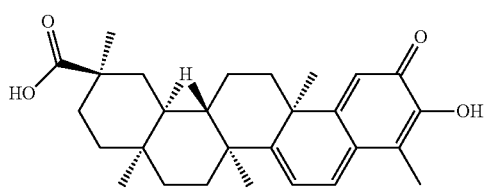 | 32.90443509 | 97.09434568 | 64.18991059 |
| Tannic Acid | 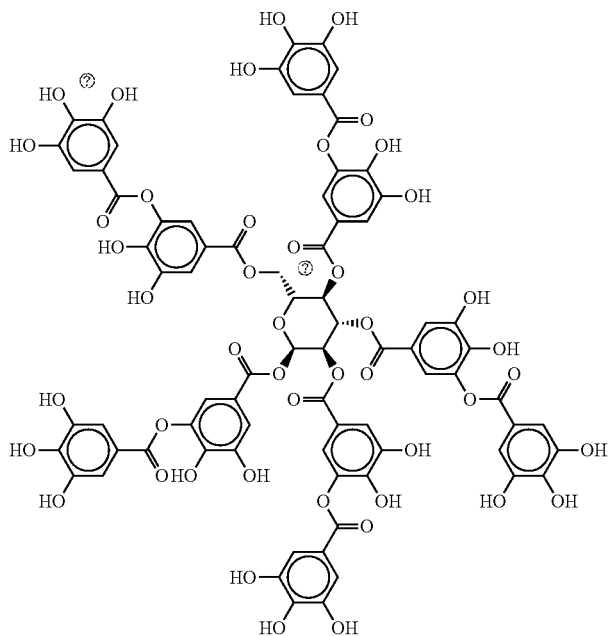 | 15.93536133 | 98.2573418 | 82.32198048 |

REFERENCES

1. Bakhshi, A., Jensen, J. P., Goldman, P., Wright, J. J., McBride, O. W., et al. (1985) Cloning the chromosomal breakpoint of t(14;18) human lymphomas: clustering around JH on chromosome 14 and near a transcriptional unit on 18 Cell 41(3), 899-906.

2. Cleary, M. L., and Sklar, J. (1985) Nucleotide sequence of a t(14;18) chromosomal breakpoint in follicular lymphoma and demonstration of a breakpoint-cluster region near a transcriptionally active locus on chromosome 18 *Proc Natl Acad Sci USA* 82(21), 7439-7443.
3. Tsujimoto, Y., Gorham, J., Cossman, J., Jaffe, E., and Croce, C. M. (1985) The t(14;18) chromosome translocations involved in B-cell neoplasms result from mistakes in VDJ joining *Science* 229(4720), 1390-1393.
4. Sattler, M., Liang, H., Nettesheim, D., Meadows, R. P., Harlan, J. E., et al. (1997) Structure of Bcl-xL-Bak peptide complex: recognition between regulators of apoptosis *Science* 275(5302), 983-986.
5. Muchmore, S. W., Sattler, M., Liang, H., Meadows, R. P., Harlan, J. E., et al. (1996) X-ray and NMR structure of human Bcl-xL, an inhibitor of programmed cell death *Nature* 381(6580), 335-341.
6. Chen, L., Willis, S. N., Wei, A., Smith, B. J., Fletcher, J. I., et al. (2005) Differential targeting of prosurvival Bcl-2 proteins by their BH3-only ligands allows complementary apoptotic function *Mol Cell* 17(3), 393-403.
7. Zhai, D., Jin, C., Huang, Z., Satterthwait, A. C., and Reed, J. C. (2008) Differential regulation of Bax and Bak by anti-apoptotic Bcl-2 family proteins Bcl-B and Mcl-1 *J Biol Chem* 283(15), 9580-9586.
8. Kitada, S., Leone, M., Sareth, S., Zhai, D., Reed, J. C., et al. (2003) Discovery, characterization, and structure-activity relationships studies of proapoptotic polyphenols targeting B-cell lymphocyte/leukemia-2 proteins *J Med Chem* 46(20), 4259-4264.
9. Nguyen, M., Marcellus, R. C., Roulston, A., Watson, M., Serfass, L., et al. (2007) Small molecule obatoclax (GX15-070) antagonizes MCL-1 and overcomes MCL-1-mediated resistance to apoptosis *Proc Natl Acad Sci USA* 104(49), 19512-19517.
10. Oltersdorf, T., Elmore, S. W., Shoemaker, A. R., Armstrong, R. C., Augeri, D. J., et al. (2005) An inhibitor of Bcl-2 family proteins induces regression of solid tumours *Nature* 435(7042), 677-681.
11. Tse, C., Shoemaker, A. R., Adickes, J., Anderson, M. G., Chen, J., et al. (2008) ABT-263: a potent and orally bioavailable Bcl-2 family inhibitor *Cancer Res* 68(9), 3421-3428.
12. Wang, G., Nikolovska-Coleska, Z., Yang, C. Y., Wang, R., Tang, G., et al. (2006) Structure-based design of potent small-molecule inhibitors of anti-apoptotic Bcl-2 proteins *J Med Chem* 49(21), 6139-6142.
13. MacVicar, G. R., Kuzel, T. M., Curti, B. D., and al., e. (2008) An open-label, multicenter, phase 1/II study of AT-101 in combination with docetaxel (D) and prednisone (P) in men with hormone refractory prostate cancer. *J Clin Oncol* 26, 16048 (Abstract).
14. Kline, M. P., Rajkumar, S. V., Timm, M. M., Kimlinger, T. K., Haug, J. L., et al. (2007) ABT-737, an inhibitor of Bcl-2 family proteins, is a potent inducer of apoptosis in multiple myeloma cells *Leukemia* 21(7), 1549-1560.
15. van Delft, M. F., Wei, A. H., Mason, K. D., Vandenberg, C. J., Chen, L., et al. (2006) The BH3 mimetic ABT-737 targets selective Bcl-2 proteins and efficiently induces apoptosis via Bak/Bax if Mcl-1 is neutralized *Cancer Cell* 10(5), 389-399.
16. Konopleva, M., Contractor, R., Tsao, T., Samudio, I., Ruvolo, P. P., et al. (2006) Mechanisms of apoptosis sensitivity and resistance to the BH3 mimetic ABT-737 in acute myeloid leukemia *Cancer Cell* 10(5), 375-388.
17. Deng, J., Carlson, N., Takeyama, K., Dal Cin, P., Shipp, M., et al. (2007) BH3 profiling identifies three distinct classes of apoptotic blocks to predict response to ABT-737 and conventional chemotherapeutic agents *Cancer Cell* 12(2), 171-185.
18. Derenne, S., Monia, B., Dean, N. M., Taylor, J. K., Rapp, M. J., et al. (2002) Antisense strategy shows that Mcl-1 rather than Bcl-2 or Bcl-x(L) is an essential survival protein of human myeloma cells *Blood* 100(1), 194-199.
19. Zhang, B., Gojo, I., and Fenton, R. G. (2002) Myeloid cell factor-1 is a critical survival factor for multiple myeloma *Blood* 99(6), 1885-1893.
20. Boisvert-Adamo, K., Longmate, W., Abel, E. V., and Aplin, A. E. (2009) Mcl-1 is required for melanoma cell resistance to anoikis *Mol Cancer Res* 7(4), 549-556.
21. Ding, Q., He, X., Xia, W., Hsu, J. M., Chen, C. T., et al. (2007) Myeloid Cell Leukemia-1 Inversely Correlates with Glycogen Synthase Kinase-3 {beta} Activity and Associates with Poor Prognosis in Human Breast Cancer *Cancer Res* 67(10), 4564-4571.
22. Lin, X., Morgan-Lappe, S., Huang, X., Li, L., Zakula, D. M., et al. (2007) 'Seed' analysis of off-target siRNAs reveals an essential role of Mcl-1 in resistance to the small-molecule Bcl-2/Bcl-XL inhibitor ABT-737 *Oncogene* 26(27), 3972-3979.
23. Taniai, M., Grambihler, A., Higuchi, H., Werneburg, N., Bronk, S. F., et al. (2004) Mcl-1 mediates tumor necrosis factor-related apoptosis-inducing ligand resistance in human cholangiocarcinoma cells *Cancer Res* 64(10), 3517-3524.
24. Bird, G. H., Bernal, F., Pitter, K., and Walensky, L. D. (2008) Chapter 22 Synthesis and Biophysical Characterization of Stabilized alpha-Helices of BCL-2 Domains *Methods Enzymol* 446, 369-386.
25. Schafmeister, C., Po, J., and Verdine, G. (2000) An all-hydrocarbon cross-linking system for enhancing the helicity and metabolic stability of peptides *J Am Chem Soc* 122, 5891-5892.
26. Danial, N. N., Walensky, L. D., Zhang, C. Y., Choi, C. S., Fisher, J. K., et al. (2008) Dual role of proapoptotic BAD in insulin secretion and beta cell survival *Nat Med* 14(2), 144-153.
27. Walensky, L. D., Kung, A. L., Escher, I., Malia, T. J., Barbuto, S., et al. (2004) Activation of apoptosis in vivo by a hydrocarbon-stapled BH3 helix *Science* 305(5689), 1466-1470.
28. Gavathiotis, E., Suzuki, M., Davis, M. L., Pitter, K., Bird, G. H., et al. (2008) BAX activation is initiated at a novel interaction site *Nature* 455(7216), 1076-1081.
29. Walensky, L. D., Pitter, K., Morash, J., Oh, K. J., Barbuto, S., et al. (2006) A stapled BID BH3 helix directly binds and activates BAX *Mol Cell* 24(2), 199-210.
30. Walensky, L. D. (2006) BCL-2 in the crosshairs: tipping the balance of life and death *Cell Death Differ* 13(8), 1339-1350.
31. Pitter, K., Bernal, F., LaBelle, J. L., and Walensky, L. D. (2008) Chapter 23 Dissection of the BCL-2 Family Signaling Network with Stabilized alpha-Helices of BCL-2 Domains *Methods Enzymol* 446, 387-408.
32. Armstrong, S. A., Kung, A. L., Mabon, M. E., Silverman, L. B., Stam, R. W., et al. (2003) Inhibition of FLT3 in MLL. Validation of a therapeutic target identified by gene expression based classification *Cancer Cell* 3(2), 173-183.
33. Shuker, S. B., Hajduk, P. J., Meadows, R. P., and Fesik, S. W. (1996) Discovering high-affinity ligands for proteins: SAR by NMR *Science* 274(5292), 1531-1534.
34. Ficarro S B, Zhang Y, Lu Y, Moghimi A R, Askenazi M, Hyatt E, Smith E D, Boyer L, Schlaeger T M, Luckey C J, Marto J A. Improved electrospray ionization efficiency compensates for diminished chromatographic resolution and enables proteomics analysis of tyrosine signaling in embryonic stem cells. *Anal Chem.* 2009 May 1;81(9): 3440-7.

What is claimed is:

1. A pharmaceutical composition comprising:
   a pharmaceutically acceptable diluent or carrier; and
   a compound of formula (J) or a pharmaceutically acceptable salt, solvate, hydrate or stereoisomer thereof:

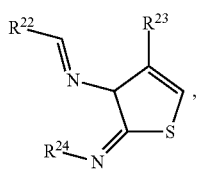

(J)

wherein
   $R^{22}$ is substituted or unsubstituted aryl, wherein $R^{22}$, when substituted, is substituted by hydroxyl or halogen;
   $R^{23}$ is $C_1$-$C_8$ alkyl, $C_2$-$C_8$ alkenyl, $C_2$-$C_8$ alkynyl, $C_1$-$C_6$ alkoxy, substituted or unsubstituted aryl, substituted or unsubstituted heteroaryl, substituted or unsubstituted cycloalkyl, or substituted or unsubstituted heterocycloalkyl, wherein $R^{23}$, when substituted, is substituted by Z;
   $R^{24}$ is $C_1$-$C_8$ alkyl, $C_2$-$C_8$ alkynyl, $C_1$-$C_6$ alkoxy, substituted or unsubstituted aryl, substituted or unsubstituted heteroaryl, substituted or unsubstituted cycloalkyl, or substituted or unsubstituted heterocycloalkyl, wherein $R^{24}$, when substituted, is substituted by Z; and
   each Z, independently, is halogen, hydroxyl, $C_1$-$C_8$ alkyl, $C_2$-$C_8$ alkenyl, $C_2$-$C_8$ alkynyl, $C_1$-$C_6$ alkoxy, substituted or unsubstituted aryl, substituted or unsubstituted heteroaryl, substituted or unsubstituted cycloalkyl, or substituted or unsubstituted heterocycloalkyl;
   provided that the compound is not

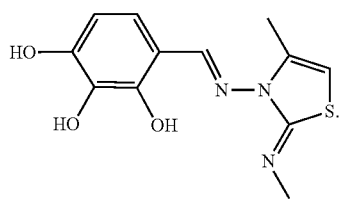 [SMILES: C/N=c1\scc(C)n1/N=C/c1ccc(O)c(O)c1O]

2. The composition of claim 1, wherein $R^{22}$ is hydroxylphenyl, dihydroxylphenyl, trihydroxylphenyl or iodophenyl.

3. The composition of claim 1, wherein $R^{23}$ is $C_1$-$C_8$ alkyl, aryl, heteroaryl or heterocycloalkyl, in which each of $C_1$-$C_8$ alkyl, aryl, heteroaryl and heterocycloalkyl is unsubstituted or substituted by Z.

4. The composition of claim 3, wherein $R^{23}$ is $C_1$-$C_8$ alkyl; unsubstituted heteroaryl; benzoxazinonyl; or aryl substituted by halogen, $C_1$-$C_8$ alkyl or $C_1$-$C_6$ alkoxy.

5. The composition of claim 4, wherein $R^{23}$ is methyl, thienyl, furyl, fluorophenyl, dichlorophenyl, dimethylphenyl, difluoromethoxyphenyl, or benzoxazinonyl.

6. The composition of claim 1, wherein $R^{24}$ is $C_1$-$C_8$ alkyl, aryl, or cycloalkyl, in which each of $C_1$-$C_8$ alkyl, aryl, and cycloalkyl is unsubstituted or substituted by Z.

7. The composition of claim 6, wherein $R^{24}$ is $C_1$-$C_8$ alkyl, $C_1$-$C_8$ alkyl substituted by phenyl, aryl substituted by halogen, or cycloalkyl.

8. The composition of claim 7, wherein $R^{24}$ is methyl, ethyl, isopropyl, benzyl, cyclohexyl or fluorophenyl.

9. A pharmaceutical composition, comprising:

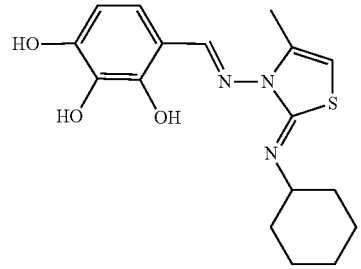 [SMILES: Cc1cs/c(=N\C2CCCCC2)n1/N=C/c1ccc(O)c(O)c1O]

or a physiologically acceptable salt, solvate, hydrate or stereoisomer thereof; and
a pharmaceutically acceptable diluent or carrier.

10. A method for modulating apoptotic cell death in a cell, comprising contacting the cell with the composition of claim 9, thereby regulating apoptotic cell death in said cell.

11. A method for modulating metabolism in a cell, comprising contacting the cell with the composition of claim 9, thereby regulating energy production and consumption to effect cell viability in said cell.

12. A method of treating the hyperproliferative disorder in a mammal, comprising administering to a mammal in need thereof, a therapeutically effective amount of the composition of claim 9.

13. The method of claim 12, wherein the hyperproliferative disorder is cancer.

14. A method for modulating apoptotic cell death in a cell, comprising contacting the cell with the composition of claim 1, thereby regulating apoptotic cell death in said cell.

15. A method for modulating metabolism in a cell, comprising contacting the cell with the composition of claim 1, thereby regulating energy production and consumption to effect cell viability in said cell.

16. A method of treating a hyperproliferative disorder in a mammal, comprising administering to the mammal in need thereof, a therapeutically effective amount of the composition of claim 1.

17. The method of claim 16, wherein the hyperproliferative disorder is cancer.

* * * * *

UNITED STATES PATENT AND TRADEMARK OFFICE
CERTIFICATE OF CORRECTION

PATENT NO. : 10,000,511 B2
APPLICATION NO. : 14/705764
DATED : June 19, 2018
INVENTOR(S) : Walensky et al.

It is certified that error appears in the above-identified patent and that said Letters Patent is hereby corrected as shown below:

On the Title Page

Column 1, Notice, Line 3:
After "0 days." delete "days.".

In the Claims

Column 199, Lines 26-31:

In Claim 1, delete " 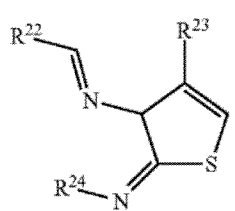 ", insert -- 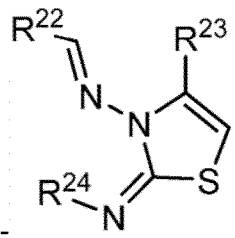 -- therefor.

Column 199, Line 26:
In Claim 1, delete "J)" and insert -- (J) -- therefor.

Column 200, Line 62:
In Claim 12, delete "the hyperproliferative disorder" and insert -- a hyperproliferative disorder -- therefor.

Column 200, Line 63:
In Claim 12, delete "administering to a mammal" and insert -- administering to the mammal -- therefor.

Signed and Sealed this
Second Day of October, 2018

Andrei Iancu
*Director of the United States Patent and Trademark Office*

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Portion of Human MCL-1

<400> SEQUENCE: 1

```
Thr Ile Asn Gln Glu Ser Cys Ile Glu Pro Leu Ala Glu Ser Ile Thr
1               5                   10                  15

Asp Val Leu Val Arg
            20
```